(12) United States Patent
Tumey et al.

(10) Patent No.: US 11,614,170 B2
(45) Date of Patent: Mar. 28, 2023

(54) WOUND THERAPY DEVICE PRESSURE MONITORING AND CONTROL SYSTEM

(71) Applicant: Innovative Therapies, LLC, Dublin, OH (US)

(72) Inventors: David Malcolm Tumey, Coral Springs, FL (US); Tianning Xu, Duluth, GA (US); Alan John Martin, Pompano Beach, FL (US); Brent Lee Burchfield, Powell, OH (US); Raymond Reade Harpham, Columbus, OH (US)

(73) Assignee: Innovative Therapies, LLC, Dublin, OH (US)

(*) Notice: Subject to any disclaimer, the term of this patent is extended or adjusted under 35 U.S.C. 154(b) by 302 days.

(21) Appl. No.: 16/870,595

(22) Filed: May 8, 2020

(65) Prior Publication Data

US 2021/0121608 A1    Apr. 29, 2021

Related U.S. Application Data

(63) Continuation of application No. 15/223,158, filed on Jul. 29, 2016, now abandoned.

(Continued)

(51) Int. Cl.
*A61M 1/00* (2006.01)
*F16K 1/02* (2006.01)
(Continued)

(52) U.S. Cl.
CPC .............. *F16K 1/02* (2013.01); *A61M 1/73* (2021.05); *A61M 1/74* (2021.05); *A61M 1/81* (2021.05); *A61M 1/82* (2021.05); *A61M 1/96* (2021.05); *A61M 39/08* (2013.01); *A61M 1/915* (2021.05); *A61M 1/918* (2021.05); *A61M 1/964* (2021.05); *A61M 1/982* (2021.05);
(Continued)

(58) Field of Classification Search
CPC .......... A61M 1/00; A61M 27/00; A61M 1/81; A61M 1/82; A61M 1/918; A61M 1/915; A61M 1/982; A61F 13/00; A61F 13/02
See application file for complete search history.

(56) References Cited

U.S. PATENT DOCUMENTS

| 5,207,648 A | 5/1993 | Gross et al. |
| 5,346,471 A | 9/1994 | Raulerson |

(Continued)

FOREIGN PATENT DOCUMENTS

| CN | 102711901 A | 10/2012 |
| EP | 2623138 A2 | 8/2013 |

(Continued)

OTHER PUBLICATIONS

US 6,216,701 B1, 04/2001, Heaton et al. (withdrawn)
(Continued)

*Primary Examiner* — Tatyana Zalukaeva
*Assistant Examiner* — Ilya Y Treyger
(74) *Attorney, Agent, or Firm* — ArentFox Schiff LLP

(57) ABSTRACT

A new system for negative pressure wound therapy is described. The system includes a patient tube set connecting the wound dressing to the suction container. The patient tube set provides separate channels for applying suction to the wound site and sensing the therapeutic pressure at the wound site. A restrictor valve may also be included in order to introduce a small air leak into the system to prevent occlusions in the patient tube set.

31 Claims, 46 Drawing Sheets

Related U.S. Application Data

(60) Provisional application No. 62/296,679, filed on Feb. 18, 2016, provisional application No. 62/198,514, filed on Jul. 29, 2015.

(51) Int. Cl.
*A61M 39/08* (2006.01)
*A61M 27/00* (2006.01)
*A61F 13/00* (2006.01)
*A61F 13/02* (2006.01)

(52) U.S. Cl.
CPC .......... *A61M 2039/082* (2013.01); *A61M 2205/3331* (2013.01); *A61M 2205/3344* (2013.01)

(56) References Cited

U.S. PATENT DOCUMENTS

| | | |
|---|---|---|
| 5,380,276 A | 1/1995 | Miller et al. |
| 5,636,643 A | 6/1997 | Argenta et al. |
| 5,645,081 A | 7/1997 | Argenta et al. |
| 5,961,485 A | 10/1999 | Martin |
| 6,135,116 A | 10/2000 | Vogel et al. |
| 6,142,982 A | 11/2000 | Hunt et al. |
| 6,345,623 B1 | 2/2002 | Heaton et al. |
| 6,553,998 B2 | 4/2003 | Heaton et al. |
| 6,695,823 B1 | 2/2004 | Lina et al. |
| 6,814,079 B2 | 11/2004 | Heaton et al. |
| 6,856,821 B2 | 2/2005 | Johnson |
| 6,994,702 B1 | 2/2006 | Johnson |
| 7,117,869 B2 | 10/2006 | Heaton et al. |
| 7,144,390 B1 | 12/2006 | Hannigan et al. |
| 7,198,046 B1 | 4/2007 | Argenta et al. |
| 7,214,202 B1 | 5/2007 | Vogel et al. |
| 7,216,651 B2 | 5/2007 | Argenta et al. |
| 7,273,054 B2 | 9/2007 | Heaton et al. |
| 7,279,612 B1 | 10/2007 | Heaton et al. |
| 7,316,672 B1 | 1/2008 | Hunt et al. |
| 7,381,859 B2 | 6/2008 | Hunt et al. |
| 7,198,046 C1 | 12/2008 | Argenta et al. |
| 5,636,643 C1 | 3/2009 | Argenta et al. |
| 7,524,286 B2 | 4/2009 | Johnson |
| 7,534,240 B1 | 5/2009 | Johnson |
| 7,540,848 B2 | 6/2009 | Hannigan et al. |
| 7,553,306 B1 | 6/2009 | Hunt et al. |
| 7,608,066 B2 | 10/2009 | Vogel |
| 5,636,643 C2 | 11/2009 | Argenta et al. |
| 5,645,081 C1 | 11/2009 | Argenta et al. |
| 7,611,500 B1 | 11/2009 | Lina et al. |
| 7,618,382 B2 | 11/2009 | Vogel et al. |
| 7,670,323 B2 | 3/2010 | Hunt et al. |
| 7,678,102 B1 | 3/2010 | Heaton |
| 7,722,582 B2 | 5/2010 | Lina et al. |
| 7,754,936 B2 | 7/2010 | Heaton et al. |
| 7,758,554 B2 | 7/2010 | Lina et al. |
| 7,799,004 B2 | 9/2010 | Tumey |
| 7,886,746 B2 | 2/2011 | Heaton et al. |
| 7,947,033 B2 | 5/2011 | Ganapathy et al. |
| 7,951,100 B2 | 5/2011 | Hunt et al. |
| 8,096,979 B2 | 1/2012 | Lina et al. |
| 8,187,210 B2 | 5/2012 | Hunt et al. |
| 8,202,262 B2 | 6/2012 | Lina et al. |
| 8,323,265 B2 | 12/2012 | Heaton |
| 8,444,613 B2 | 5/2013 | Svedman et al. |
| 8,641,692 B2 | 2/2014 | Tout et al. |
| 8,641,693 B2 | 2/2014 | Locke et al. |
| 8,647,315 B2 | 2/2014 | Simmons et al. |
| 8,663,132 B2 | 3/2014 | Randolph |
| 8,679,079 B2 | 3/2014 | Heaton et al. |
| 8,680,359 B2 | 3/2014 | Robinson et al. |
| 8,690,845 B2 | 4/2014 | Long et al. |
| 8,702,665 B2 | 4/2014 | Locke et al. |
| 8,708,981 B2 | 4/2014 | Locke et al. |
| 8,708,984 B2 | 4/2014 | Robinson et al. |
| 8,715,253 B2 | 5/2014 | Cavanaugh, II et al. |
| 8,715,267 B2 | 5/2014 | Bengtson et al. |
| 8,721,629 B2 | 5/2014 | Hardman et al. |
| 8,725,528 B2 | 5/2014 | Locke et al. |
| 8,728,044 B2 | 5/2014 | Coulthard et al. |
| 8,728,045 B2 | 5/2014 | Hu et al. |
| 8,728,046 B2 | 5/2014 | Hu et al. |
| 8,734,409 B2 | 5/2014 | Swain et al. |
| 8,734,474 B2 | 5/2014 | Swain et al. |
| 8,735,644 B2 | 5/2014 | Johnson et al. |
| 8,740,878 B2 | 6/2014 | Heaton |
| 8,747,376 B2 | 6/2014 | Locke et al. |
| 8,753,322 B2 | 6/2014 | Hu et al. |
| 8,758,314 B2 | 6/2014 | Hall et al. |
| 8,758,315 B2 | 6/2014 | Chen et al. |
| 8,758,328 B2 | 6/2014 | Locke et al. |
| 8,771,240 B2 | 7/2014 | Tout et al. |
| 8,951,236 B2 | 2/2015 | Heaton et al. |
| 9,023,012 B2 | 5/2015 | Tout et al. |
| 2002/0017304 A1 | 2/2002 | Heaton et al. |
| 2002/0120185 A1 | 8/2002 | Johnson et al. |
| 2002/0143286 A1 | 10/2002 | Tumey et al. |
| 2003/0188754 A1 | 10/2003 | Heaton et al. |
| 2004/0006319 A1 | 1/2004 | Lina et al. |
| 2004/0030304 A1 | 2/2004 | Hunt et al. |
| 2004/0225208 A1 | 11/2004 | Johnson et al. |
| 2005/0028828 A1 | 2/2005 | Heaton et al. |
| 2005/0283105 A1 | 12/2005 | Heaton et al. |
| 2006/0029675 A1 | 2/2006 | Ginther |
| 2006/0149171 A1 | 7/2006 | Vogel et al. |
| 2006/0173253 A1 | 8/2006 | Ganapathy et al. |
| 2006/0213527 A1 | 9/2006 | Argenta et al. |
| 2007/0014837 A1 | 1/2007 | Johnson et al. |
| 2007/0021697 A1 | 1/2007 | Ginther et al. |
| 2007/0032778 A1 | 2/2007 | Heaton et al. |
| 2007/0073200 A1 | 3/2007 | Hannigan et al. |
| 2007/0167927 A1 | 7/2007 | Hunt et al. |
| 2007/0219513 A1 | 9/2007 | Lina et al. |
| 2008/0039761 A1 | 2/2008 | Heaton et al. |
| 2008/0208147 A1 | 8/2008 | Argenta et al. |
| 2008/0243044 A1 | 10/2008 | Hunt et al. |
| 2008/0312613 A1 | 12/2008 | Heaton et al. |
| 2009/0117087 A1 | 5/2009 | Carroll et al. |
| 2009/0240216 A1 | 9/2009 | Hannigan et al. |
| 2009/0253972 A1 | 10/2009 | Johnson |
| 2009/0270820 A1 | 10/2009 | Johnson et al. |
| 2009/0312727 A1 | 12/2009 | Heaton et al. |
| 2010/0022972 A1 | 1/2010 | Lina et al. |
| 2010/0112087 A1 | 5/2010 | Harrison et al. |
| 2010/0121230 A1 | 5/2010 | Vogel et al. |
| 2010/0145289 A1 | 6/2010 | Lina et al. |
| 2010/0160878 A1 | 6/2010 | Hunt et al. |
| 2010/0185121 A1 | 7/2010 | Carroll et al. |
| 2010/0262095 A1 | 10/2010 | Hall |
| 2011/0172611 A1 | 7/2011 | Yoo et al. |
| 2011/0196284 A1 | 8/2011 | Ganapathy et al. |
| 2011/0224635 A1 | 9/2011 | Hunt et al. |
| 2012/0083755 A1 | 4/2012 | Lina et al. |
| 2012/0220963 A1 | 8/2012 | Hunt et al. |
| 2013/0310809 A1 | 11/2013 | Armstrong et al. |
| 2014/0031774 A1 | 1/2014 | Bengtson |
| 2014/0039424 A1 | 2/2014 | Locke et al. |
| 2014/0039425 A1 | 2/2014 | McNeil |
| 2014/0039426 A1 | 2/2014 | Coulthard et al. |
| 2014/0039428 A1 | 2/2014 | Kagan |
| 2014/0046282 A1 | 2/2014 | Locke et al. |
| 2014/0058344 A1 | 2/2014 | Toth |
| 2014/0058345 A1 | 2/2014 | Robinson et al. |
| 2014/0066867 A1 | 3/2014 | Locke et al. |
| 2014/0068914 A1 | 3/2014 | Coward et al. |
| 2014/0081227 A1 | 3/2014 | Cornet et al. |
| 2014/0094928 A1 | 4/2014 | Swain et al. |
| 2014/0107597 A1 | 4/2014 | Hu et al. |
| 2014/0114264 A1 | 4/2014 | Tout et al. |
| 2014/0121614 A1 | 5/2014 | Tout et al. |
| 2014/0121615 A1 | 5/2014 | Locke et al. |
| 2014/0121616 A1 | 5/2014 | Sammons et al. |
| 2014/0121617 A1 | 5/2014 | Locke et al. |
| 2014/0134229 A1 | 5/2014 | Zimnitsky et al. |

(56) References Cited

U.S. PATENT DOCUMENTS

| | | |
|---|---|---|
| 2014/0155791 A1 | 6/2014 | Robinson et al. |
| 2014/0155849 A1 | 6/2014 | Heaton et al. |
| 2014/0163492 A1 | 6/2014 | Hunt et al. |
| 2014/0180226 A1 | 6/2014 | Long et al. |
| 2014/0180227 A1 | 6/2014 | Robinson et al. |
| 2014/0188061 A1 | 7/2014 | Locke et al. |
| 2015/0105741 A1 | 4/2015 | Heaton |
| 2015/0119826 A1 | 4/2015 | Perkins et al. |

FOREIGN PATENT DOCUMENTS

| | | |
|---|---|---|
| EP | 1212111 A1 | 4/2015 |
| JP | 2013517098 A | 4/2016 |
| JP | 2014533579 A | 7/2017 |
| WO | 2009068665 A1 | 6/2009 |
| WO | 2009071926 A1 | 6/2009 |
| WO | 2011087871 A2 | 7/2011 |

OTHER PUBLICATIONS

US 7,186,244 B1, 03/2007, Hunt et al. (withdrawn)
International Preliminary Report on Patentability and Written Opinion for Application No. PCT/US2016/044647, dated Jan. 30, 2018, 10 pages.
International Search Report and Written Opinion for Application No. PCT/US2016/044647, dated Jan. 4, 2017, 15 pages.

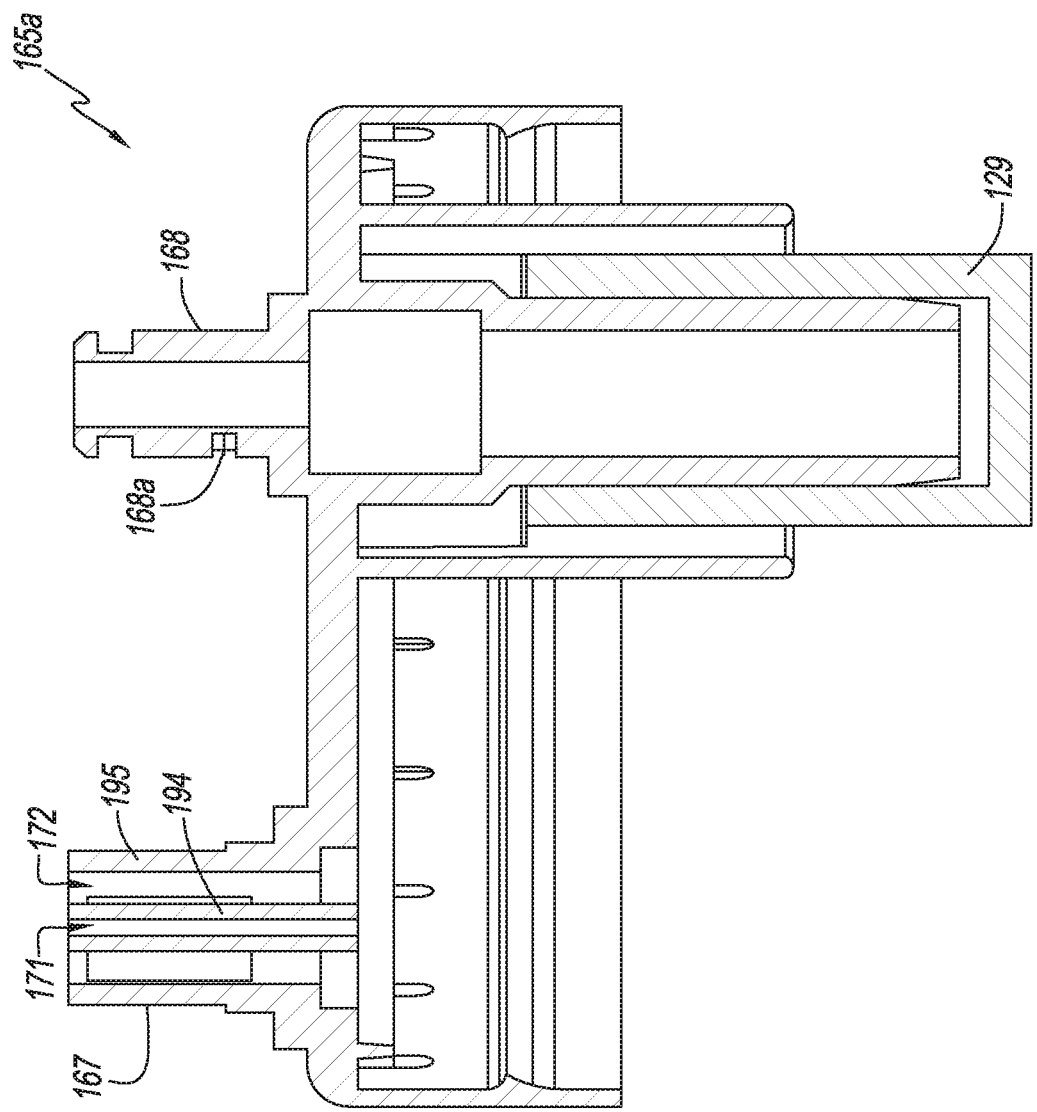

WOUND THERAPY DEVICE PRESSURE MONITORING AND CONTROL SYSTEM

CROSS-REFERENCE TO RELATED APPLICATIONS

This application is a Continuation of U.S. Non-Provisional application Ser. No. 15/223,158 filed on Jul. 29, 2016, titled, "WOUND THERAPY DEVICE PRESSURE MONITORING AND CONTROL SYSTEM" which claims priority to U.S. Provisional Patent Application No. 62/198,514, filed on Jul. 29, 2015, titled, "WOUND THERAPY DEVICE PRESSURE MONITORING AND CONTROL SYSTEM" and U.S. Provisional Patent Application No. 62/296,679, filed on Feb. 18, 2016, titled "WOUND THERAPY DEVICE PRESSURE MONITORING AND CONTROL SYSTEM". The entirety of each of these applications is hereby incorporated by reference.

BACKGROUND

Negative pressure wound therapy includes a vacuum source connected to a wound dressing. Various porous dressings comprising gauze, felts, foams, beads and/or fibers can be used in conjunction with a semi-permeable cover and a controlled vacuum source. A collection container may be used to collect wound exudate and fluid that drains from the wound.

In addition to using negative pressure wound therapy, many devices employ concomitant wound irrigation. For example, a known wound healing apparatus includes a porous dressing made of polyurethane foam placed adjacent a wound and covered by a semi-permeable and flexible plastic sheet. The dressing further includes fluid supply and fluid drainage connections in communication with the cavity formed by the cover and foam. The fluid supply is connected to a fluid source that can include an aqueous-based topical antibiotic solution or isotonic saline, for example, for use in providing therapy to the wound. The fluid drainage can be connected to a vacuum source where fluid can be removed from the cavity and subatmospheric pressures can be maintained inside the cavity.

Other devices use vacuum sealing of wound dressings including polyvinyl alcohol foam cut to size and stapled to the margins of the wound. The dressings are covered by a semi-permeable membrane while suction and fluid connections are provided by small plastic tubes introduced subcutaneously into the cavity formed by the foam and cover. Such devices alternate in time between vacuum drainage and the introduction of aqueous medicaments to the wound site.

However, such devices may fail to address the problems caused by standing fluid and occlusions in a tube connecting the wound dressing to the collection container.

SUMMARY

A wound therapy system is described, which comprises a wound dressing, a pressure sensor, a container having an internal chamber, a vacuum source pneumatically associated with the internal chamber of the container, and a tube set comprising a first tube and a second tube positioned inside a lumen of the first tube. A space between the first tube and the second tube forms a fluid channel, and a lumen of the second tube forms a sensor channel in the tube set. The wound dressing may be pneumatically associated with the internal chamber of the container by the fluid channel of the tube set. The wound dressing may be pneumatically associated with the pressure sensor by the sensor channel of the tube set. A crushing force required to occlude the fluid channel is greater than a crushing force required to occlude a fluid channel of a comparison tube set that does not include a second tube positioned inside a lumen of the first tube.

A method of wound therapy is also described, which comprises applying a dressing to a wound, wherein the dressing is coupled to a tube set comprising a fluid channel and a sensor channel; applying a vacuum to the fluid channel, wherein the vacuum draws exudate from the wound into the fluid channel; and providing a restrictor pneumatically associated with the wound dressing by the sensor channel, the restrictor having a hole through which air can leak into the sensor channel, wherein the air pushes exudate from the wound into the fluid channel of the tube set.

A device for creating an air leak is also described, the device comprising a body having a first port in communication with a second port; a cap coupled to the first port of the body, the cap having a hole; and a porous material positioned between the cap and the first port of the body. Air may be configured to enter the device through the hole in the cap and pass through the porous material before entering the body via the first port.

BRIEF DESCRIPTION OF THE FIGURES

FIG. 3E shows a cross-sectional view of the lid shown in FIGS. 3B-3C, taken along line 3e. For simplicity, the sensor tube connected to the patient port (shown in FIG. 3D) is not shown in FIG. 3E.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details.

Various aspects of a negative pressure wound therapy system may be illustrated by describing components that are coupled, attached, connected, pneumatically associated, and/or joined together. As used herein, the terms "coupled", "attached", "connected", "pneumatically associated", "in communication with", and/or "joined" are interchangeably used to indicate either a direct connection between two components or, where appropriate, an indirect connection to one another through intervening or intermediate components. In contrast, when a component is referred to as being "directly coupled", "directly attached", "directly connected" and/or "directly joined" to another component there are no intervening elements shown in said examples.

Figure 1A:
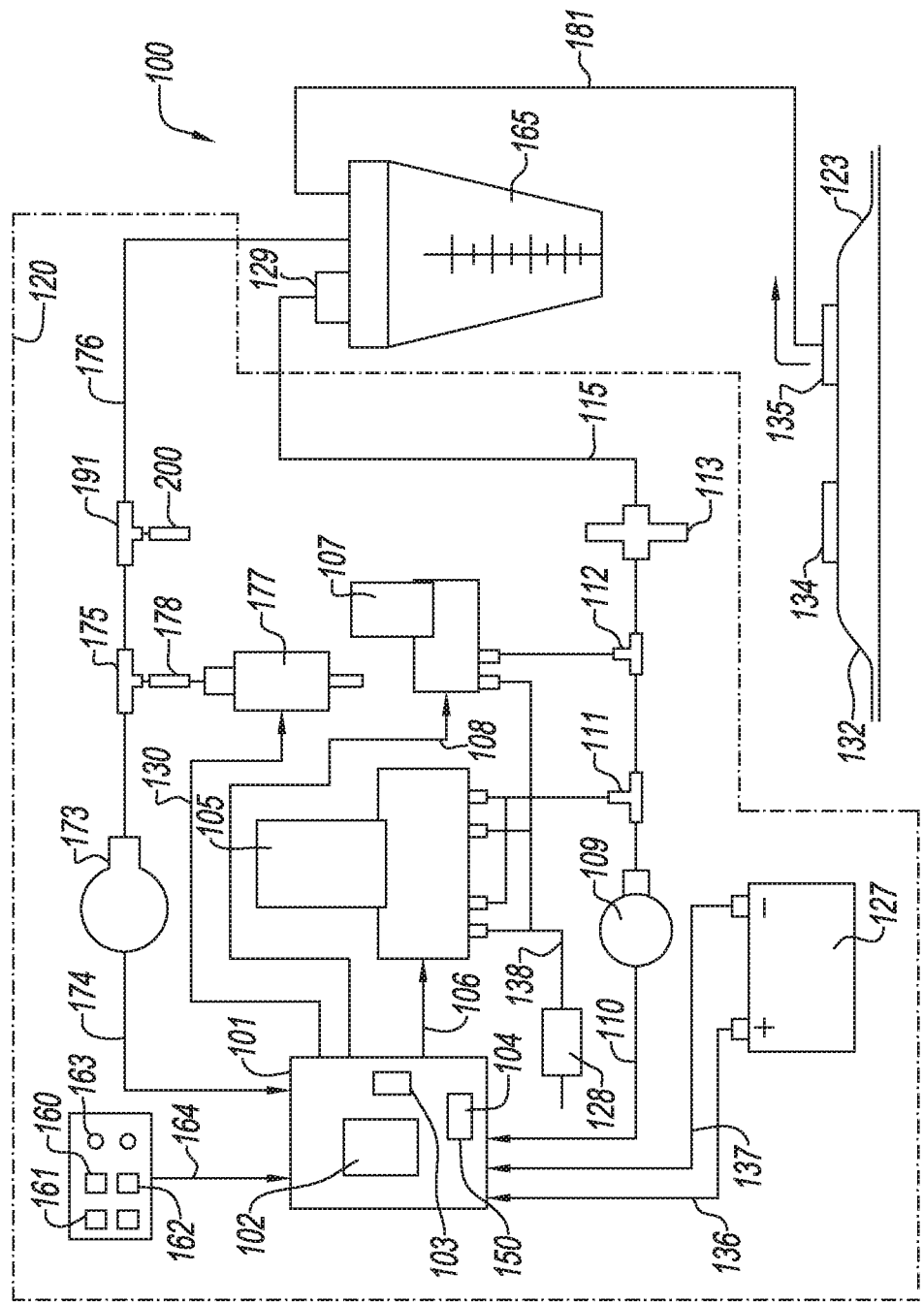
FIGS. 1A-1C show schematic depictions of various configurations of a negative pressure wound therapy system.
Figure 1B:
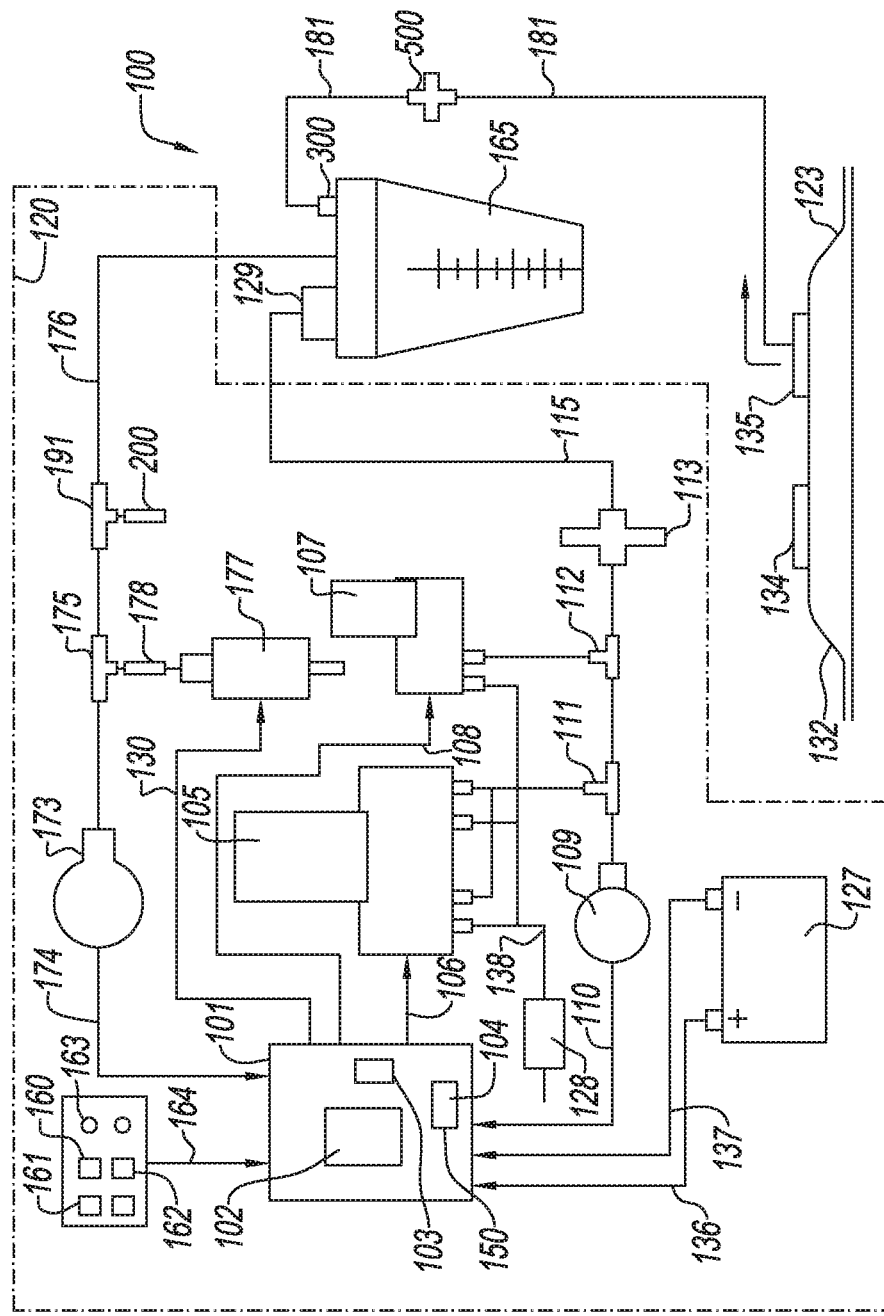
Figure 1C:
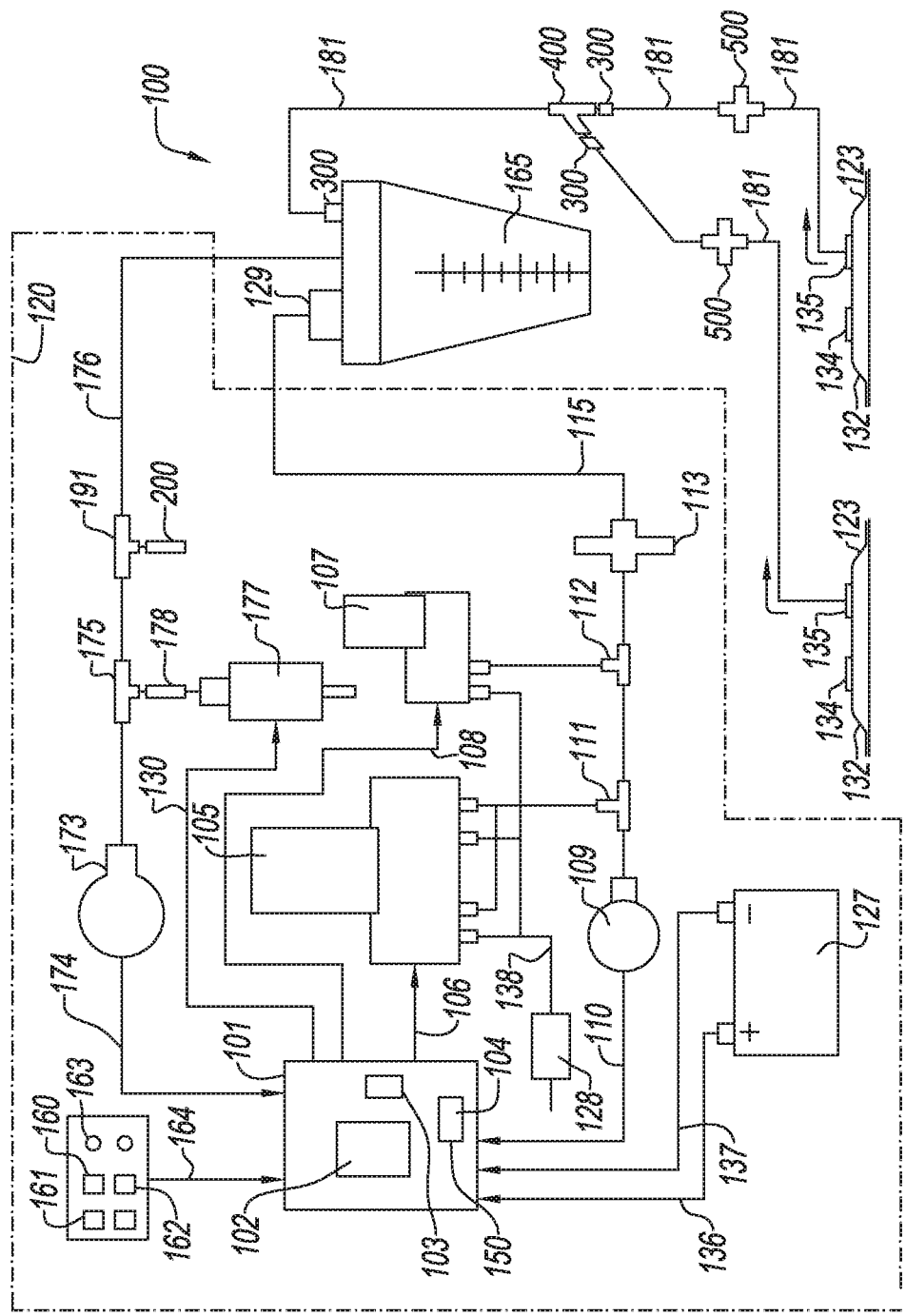

As illustrated in FIGS. 1A-1C, a negative pressure wound therapy system 100 may include a microcontroller 101, a membrane keypad and display 160, one or more vacuum pumps 105 and/or 107, a collection container 165, one or more fluid barriers 129 and/or 113, a wound dressing 123, a battery 127, a muffler 128, a patient tube set 181, an adjustable restrictor 200, a solenoid 177, an optional orifice restrictor 178, a pump pressure sensor 109, and a wound pressure sensor 173. These components may be connected through a series of adapters, connectors, pneumatic tubes and electrical cables. Various configurations of the system 100 are contemplated, and example configurations of the system 100 are shown in FIGS. 1B and 1C. The system 100 may also include a one or more valves 500, additional wound dressings 123, y-connector 400, and various adapters 300.

Many of the components may be provided as part of a pump unit 120, which may include one or more of the microcontroller 101, membrane keypad and display 160, vacuum pumps 105 and/or 107, fluid barrier 113, battery 127, muffler 128, adjustable restrictor 200, solenoid 177, orifice restrictor 178, pump pressure sensor 109, wound pressure sensor 173, and related pneumatic tubes and electrical cables. Pneumatic tubes 176 and 115 may be separate components used to connect the collection container 165 to the pump unit 120, or they may preferably be provided inside the pump unit 120. The pump unit 120 may have a vacuum port which connects to pneumatic tube 115, and a sensor port which connects to pneumatic tube 176. If pneumatic tubes 176 and 115 are provided inside the pump unit 120, the pump unit 120 may have a vacuum port at the end of pneumatic tube 115 that interfaces with the canister 165, and a sensor port at the end of pneumatic tube 176 that interfaces with the canister 165.

Controller

As illustrated in FIGS. 1A-1C, the negative pressure wound therapy system 100 generally includes a microcontroller 101 having an embedded microprocessor 102, Random Access Memory (RAM) 103 and Read Only Memory (ROM) 104. ROM 104 contains programming instructions for a control algorithm 150. ROM 104 may be non-volatile and may retain its programming when the power is terminated. RAM 103 is utilized by the control algorithm 150 for storing variables such as pressure measurements, alarm counts and the like, which the control algorithm 150 uses while generating and maintaining the vacuum.

Vacuum Sources

Microcontroller 101 is electrically associated with, and controls the operation of, a first vacuum pump 105 and an optional second vacuum pump 107 through electrical cables 106 and 108 respectively. To increase the airflow of the system, additional vacuum pumps may also be included. Electrical cables used with system 100 may be multi-conductor ribbon cables or flat flexible cables (FFC), or any cable that allows communication between two or more system components. First vacuum pump 105 and optional second vacuum pump 107 may be one of many types including, for example, the pumps sold under the trademarks Hargraves® and Thomas®. Vacuum pumps 105 and 107 may use, for example, a reciprocating diaphragm or piston to create vacuum and are typically powered by a D.C. motor that may also optionally use a brushless commutator for increased reliability and longevity. Vacuum pumps 105 and 107 may also be, for example, a rotary diaphragm pump which is a hybrid of a rotary pump and a diaphragm pump. Although some embodiments include one or more pumps as the vacuum source, the system 100 may use any type of vacuum source, including a squeeze bulb, a spring-loaded suction device, or hospital-supplied "wall suction" with pressure regulator/controller.

Vacuum pumps 105 and/or 107 may be capable of producing vacuum pressures, which are pressures that have lower absolute values compared to the atmospheric pressure of the surrounding environment. The vacuum pumps 105 and/or 107 may be able to produce vacuum pressures that range from about 70 mmHg below atmospheric pressure to about 150 mmHg below atmospheric pressure, where vacuum pressures of 150 mmHg below atmospheric pressure are stronger vacuums compared to vacuum pressures of 70 mmHg below atmospheric pressure. For example, at standard atmospheric pressure of 760 mmHg, vacuum pumps 105 and/or 107 may generate a vacuum pressure having an absolute value ranging from about 610 mmHg to about 690 mmHg, where vacuum pressures of 610 mmHg are stronger vacuums compared to vacuum pressures of 690 mmHg. In addition, vacuum pumps 105 and/or 107 may also be capable of producing vacuum pressures outside this range. For example, vacuum pumps 105 and/or 107 may be able to produce vacuum pressures that range from about 50 mmHg below atmospheric pressure to about 200 mmHg below atmospheric pressure.

An acoustic muffler 128 may be pneumatically associated with the exhaust ports of vacuum pumps 105 and/or 107 through pneumatic exhaust tubing 138 and is configured to reduce exhaust noise produced by the pumps during operation. An activated carbon odor trap may also be associated with the exhaust ports of vacuum pumps 105 and/or 107 through pneumatic exhaust tubing 138.

In normal operation of the negative pressure wound therapy system 100, first vacuum pump 105 (and optionally one or more additional vacuum pumps, such as a second vacuum pump 107) may be used to generate an initial or "draw-down" vacuum while the optional second vacuum pump 107 may be used to maintain a desired vacuum within the system 100, compensating for leaks or pressure fluctuations. The second vacuum pump 107 may be smaller and quieter than the first vacuum pump 105 providing a means to maintain the desired pressure without significantly disturbing the patient.

Display

A membrane keypad and display 160 may be electrically associated with microcontroller 101 through electrical cable 164. Membrane switches 161 provide power control, while membrane switches 162 may be used to preset the desired vacuum levels. Light emitting diodes (LEDs) 163 may be provided to indicate alarm conditions associated with collection container 165 fluid level and wound dressing 123 leaks. Preferably, an LCD display could be used in place of the LEDs 163 to indicate alarm conditions.

Power

The system 100 may be powered by an external source of power. A battery 127 is optionally provided to permit portable operation of the negative pressure wound therapy system 100. Battery 127, which may be Lithium Ion, Nickel-Metal-Hydride (NiMH), Nickel-Cadmium, (NiCd) or their equivalent, is electrically associated with microcontroller 101 through electrical cables 136 and 137. Battery 127 is charged by circuits related with microcontroller 101 while an external source of power is available such as would typically be supplied by a low-voltage A.C. adapter. When an external source of power is not available and the unit is to operate in a portable mode, battery 127 supplies power to the negative pressure wound therapy system 100.

Collection Container

Figure 2A:
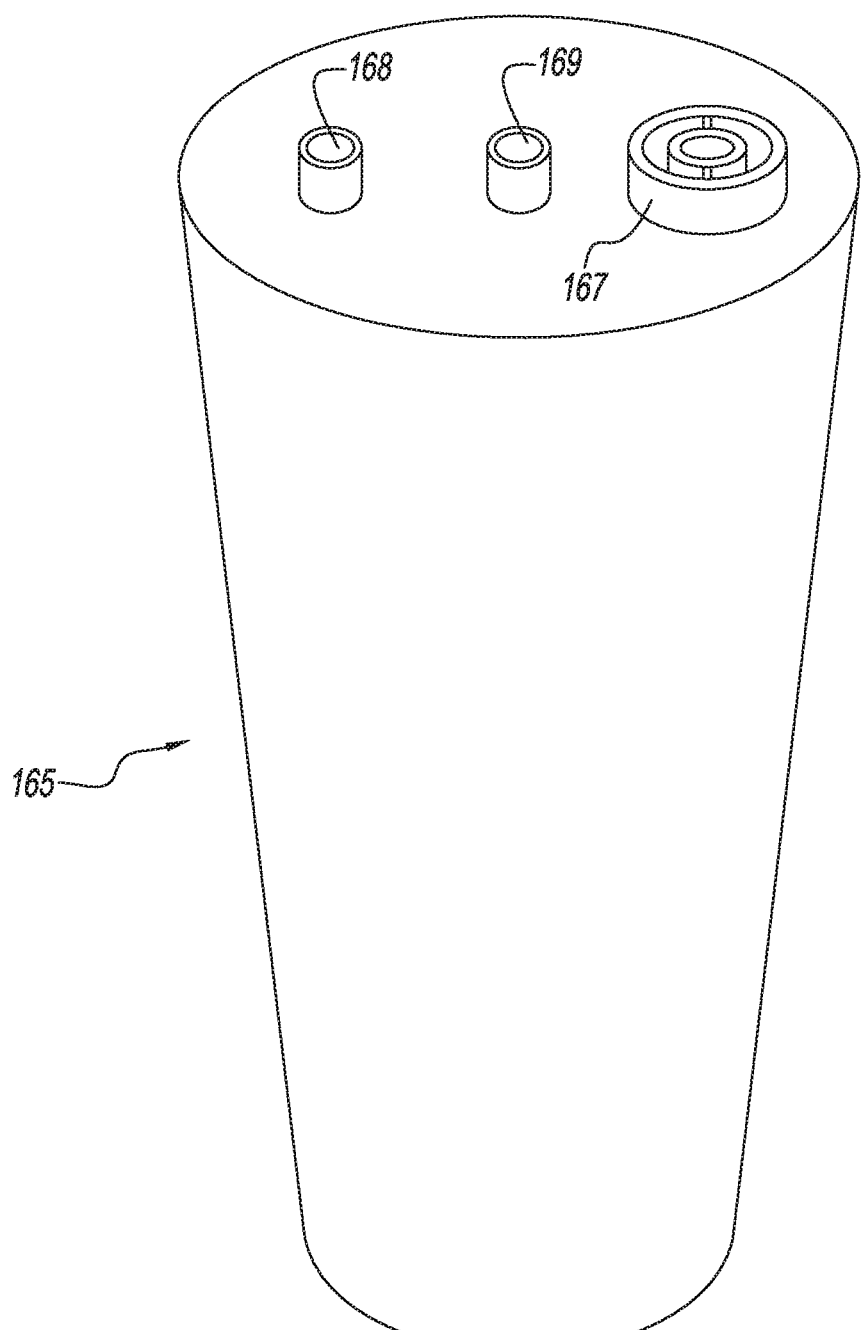
FIG. 2A shows a perspective view of a first embodiment of a collection container used in the negative pressure wound therapy system shown in FIGS. 1A-1C.
Figure 2B:
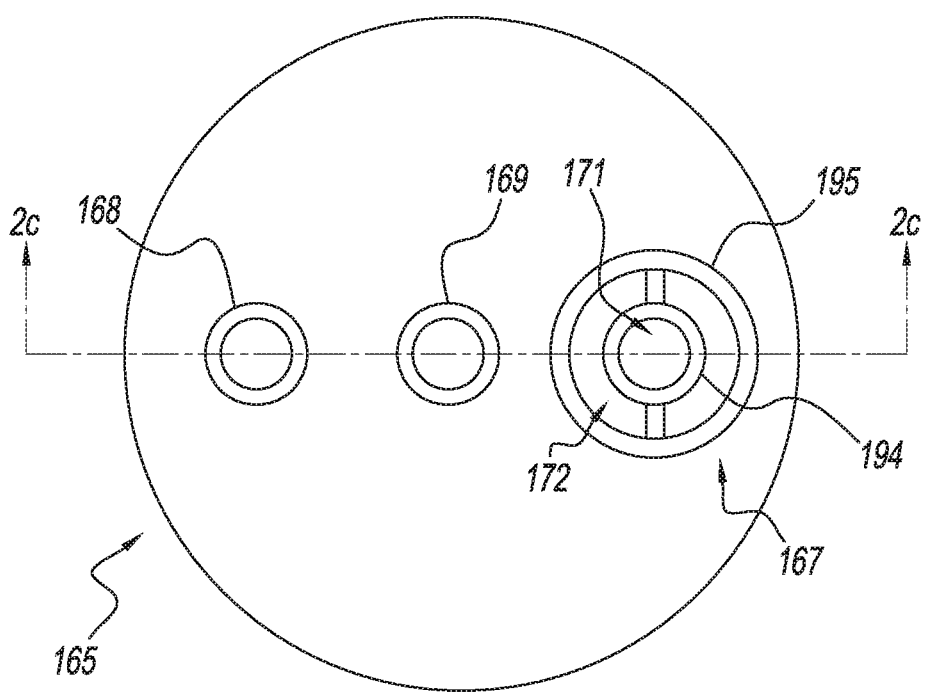
FIG. 2B shows a top view of the collection container shown in FIG. 2A.
Figure 2C:
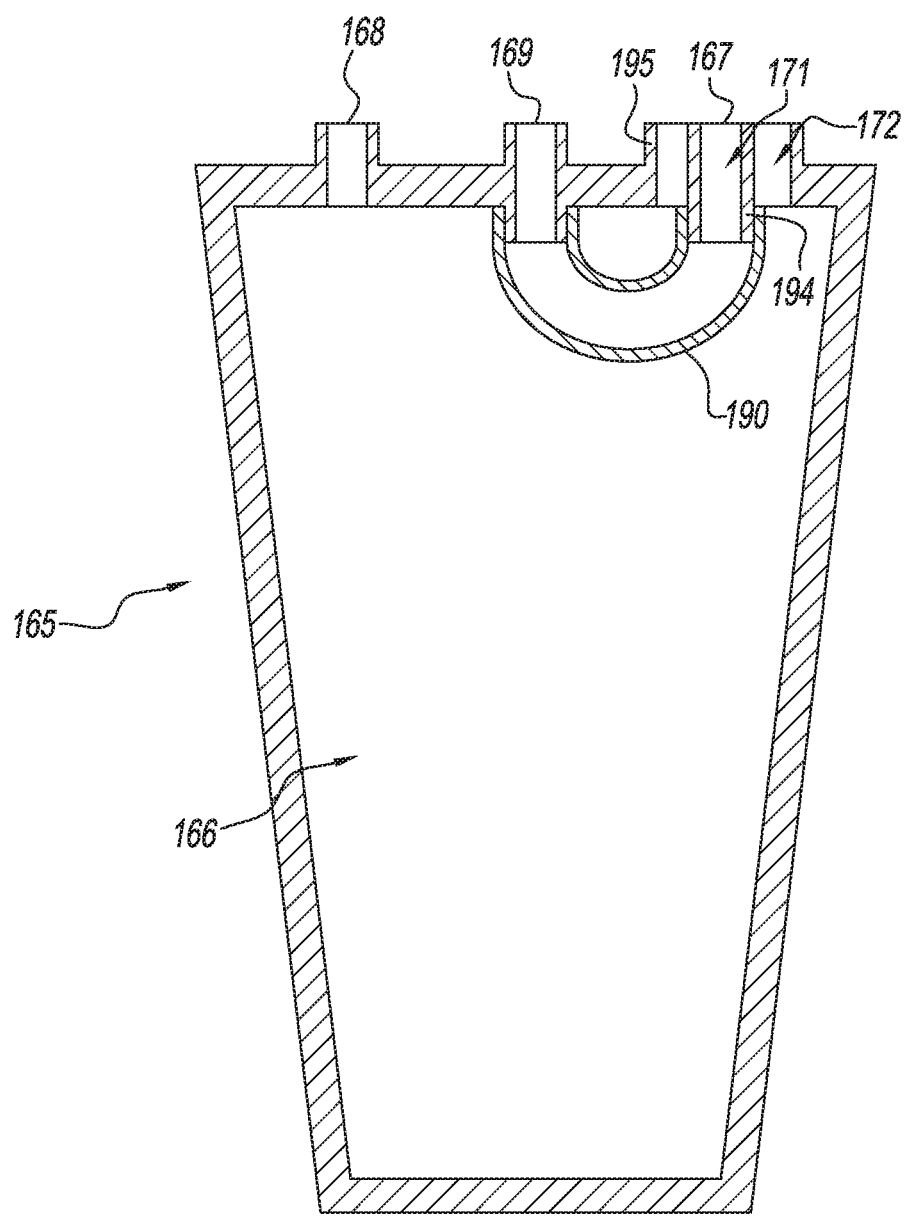
FIG. 2C shows a cross-sectional view of the collection container shown in FIGS. 2A-2B, taken along line 2C.
Figure 3A:
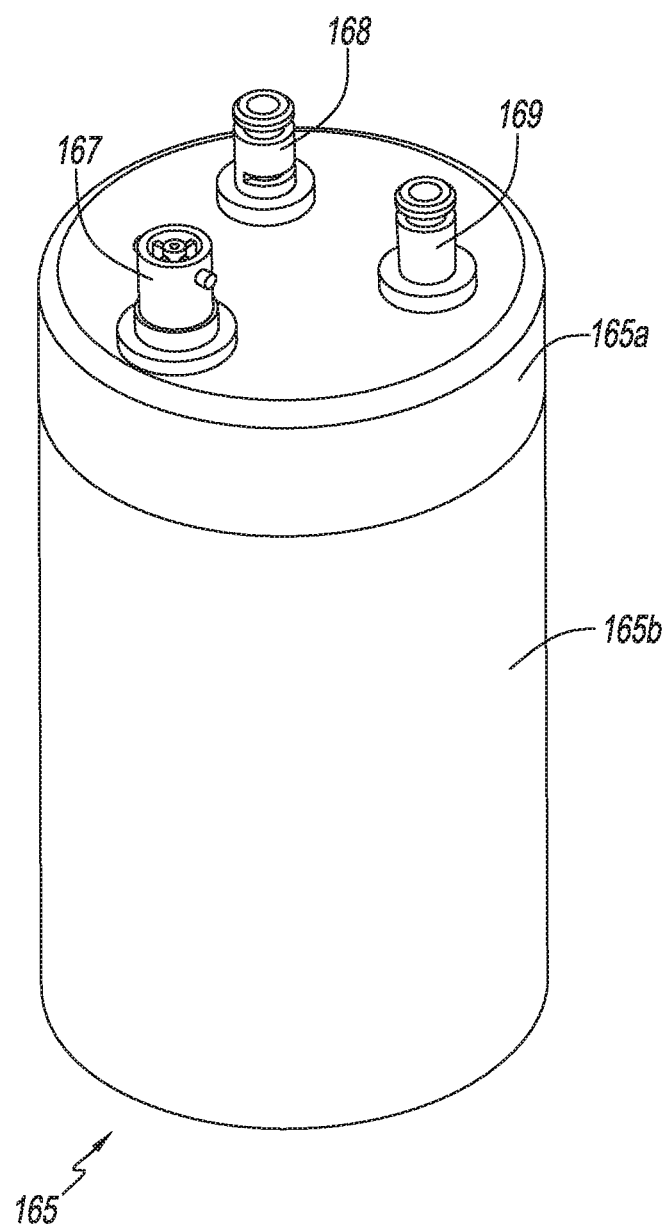
FIG. 3A shows a perspective view of a second embodiment of a collection container used in the negative pressure wound therapy system shown in FIGS. 1A-1C.
Figure 3B:
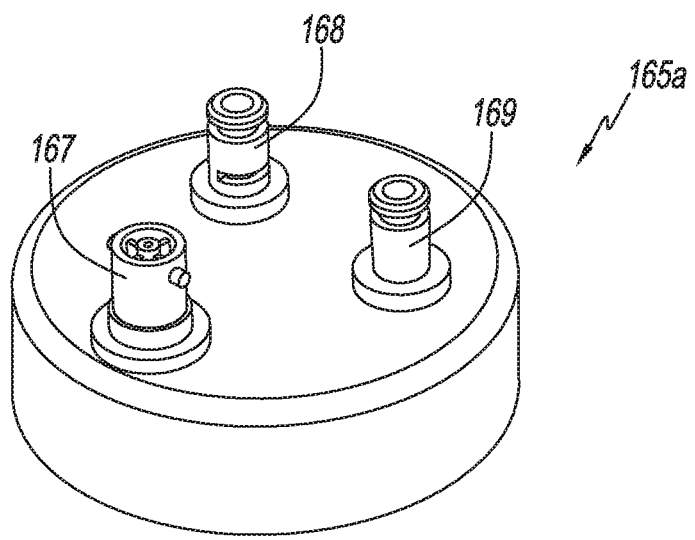
FIG. 3B shows a perspective view of a lid of the second embodiment of the collection container shown in FIG. 3A.
Figure 3C:
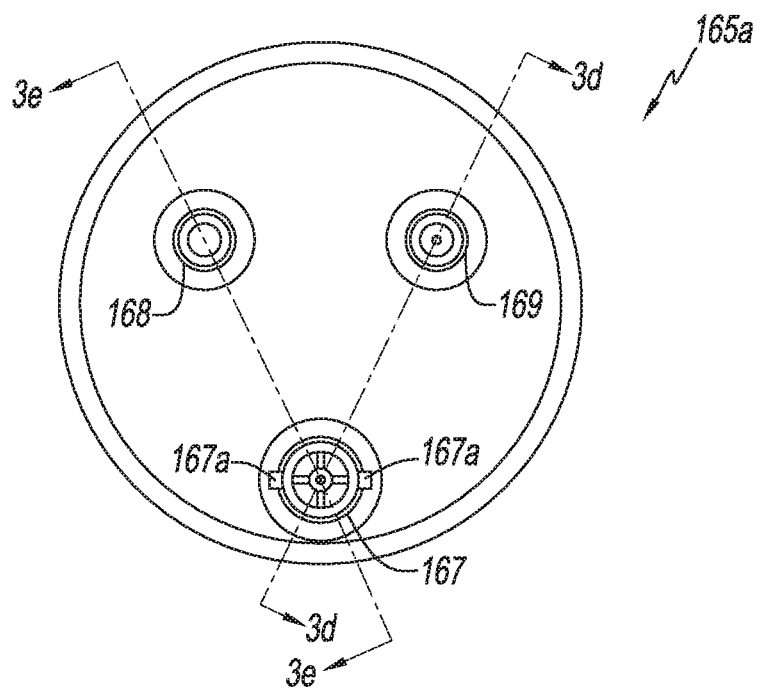
FIG. 3C shows a top view of the lid shown in FIG. 3B.
Figure 3D:
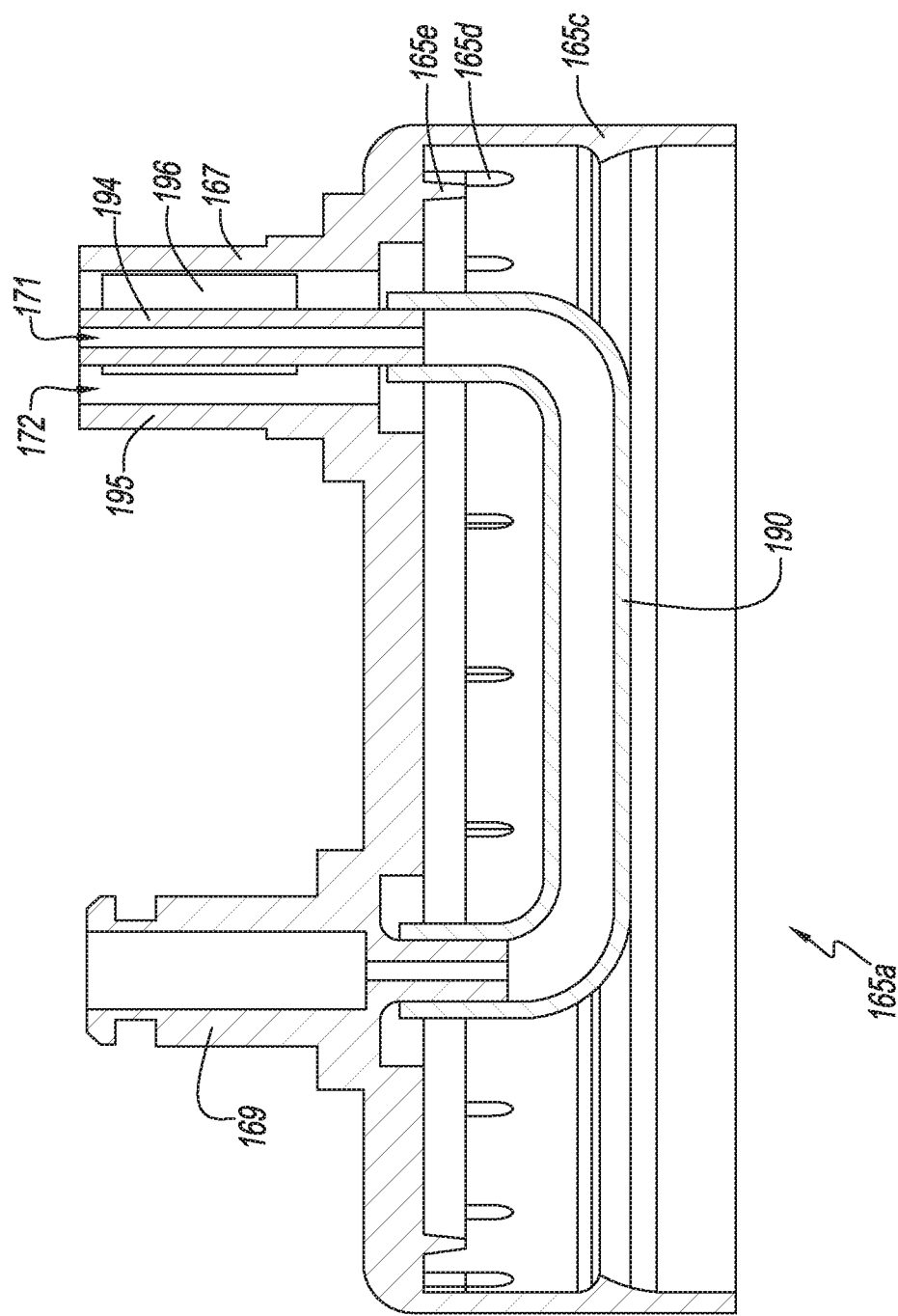
FIG. 3D shows a cross-sectional view of the lid shown in FIGS. 3B-3C, taken along line 3d.

The negative pressure wound therapy system 100 includes a collection container 165. A first embodiment of the collection container 165 is shown in FIGS. 2A-2C, and a second embodiment of a collection container 165 is shown in FIG. 3A. The collection container 165 encloses an internal chamber 166 into which fluid and exudate may drain. The collection container 165 may be a canister, an in-line vessel, or any container capable of collecting exudate. The volume of the collection container 165 may vary. The collection container 165 may be formed as a cylinder (as shown in FIG. 3A), an inverted truncated cone (as shown in FIG. 2A), or any number of other shapes. In a preferred embodiment, the collection container 165 may be substantially cylindrical. In some embodiments, the volume of the collection container 165 may be between about 300 mL and about 1200 mL. It may be preferable that collection container 165 has a volume which does not exceed about 1500 mL in order to prevent accidental exsanguination of a patient in the event hemostasis has not yet been achieved at the wound site.

The embodiments shown in FIGS. 2A-2C and 3A-3E have three openings in the collection container 165: a patient port 167, a vacuum port 168, and a sensor port 169. However, fewer or additional openings are possible. In FIGS. 2A-2C, 6, and 7, the patient port 167, vacuum port 168, and sensor port 169 are linearly arranged on the collection container 165. However, other port arrangements are also possible. For example, the patient port 167, vacuum port 168, and sensor port 169 may form a triangle on the collection container 165, as shown in FIGS. 3A-3E. Beneficially, the vacuum port 168 and sensor port 169 may be positioned on the collection container 165 such that they may be able to connect directly to ports on the pump unit 120 without the use of additional pneumatic tubing. The vacuum port 168 and/or sensor port 169 may include a locking feature 168a that allows the collection container to connect to the pump unit 120 (for example, a groove which may receive a latch on one of the ports on the pump unit 120). However, pneumatic tubing 176, 115 outside the pump unit 120 (as shown in FIGS. 1A-1C) may also be used to connect the vacuum port 168 and sensor port 169 on the collection container 165 to ports on the pump unit 120.

The internal chamber 166 of the collection container 165 may be pneumatically associated with vacuum pumps 105 and/or 107 through a tube 115 connected to the vacuum port 168 of the collection container 165. Tube 115 may connect to first vacuum pump 105 and optional second vacuum pump 107 through "T" connectors 111 and 112, respectively.

A fluid barrier 129 may be provided with the collection container 165. The fluid barrier 129 may be proximate to the vacuum port 168 and may be configured to prevent fluids collected in the collection container 165 from escaping through the vacuum port 168 into tube 115, which could potentially damage vacuum pumps 105 and 107. The fluid barrier 129 may be a porous polymer hydrophobic filter such as those available under the trademark Porex®. Alternatively, the fluid barrier 129 may have a mechanical float design or may have one or more membranes of hydrophobic material such as those available under the trademark Gore-Tex™. A secondary barrier 113 may include a hydrophobic membrane which may be provided in line with tube 115 to prevent fluid ingress into the system 100 in the event fluid barrier 129 fails to operate as intended. The fluid barrier 129 may be included on the outside of the collection container 165 as shown in FIGS. 1A-1C, or it may be positioned inside the internal chamber 166 of the collection container 165. Preferably, the fluid barrier 129 may be connected to a lid 165a of the collection container 165 as shown in FIG. 3E.

The patient port 167 of collection container 165 may include a first attachment 195 and a second attachment 194. As shown in the exemplary embodiments of FIGS. 2A-2C and 3A-3E, the second attachment 194 may be positioned inside the first attachment 195, with a web 196 connecting the first attachment 195 and the second attachment 194. The inner walls of the second attachment 194 form a sensor channel 171, and the space between the first attachment 195 and the second attachment 194 forms a fluid channel 172. A sensor tube 190, shown in FIG. 7, may be coupled to collection container 165 and connects the second attachment 194 of the patient port 167 to the sensor port 169 such that air flowing through the sensor channel 171 of the patient port 167 remains separate from the air in the internal chamber 166. Although sensor tube 190 is shown as a separate tube in FIG. 7, sensor tube 190 may be integrally formed with, or provided as part of, one or more of the collection container 165, tube 176, or second tube 182 of patient tube set 181.

The collection container 165 may be formed as a single component (as shown in the first embodiment, FIGS. 2A-2C), or preferably, the collection container 165 may be an assembly of a lid 165a and a base 165b (as shown in the second embodiment, FIG. 3A). If the collection container 165 is an assembly of a lid 165a and a base 165b, the lid 165a and the base 165b together may enclose the internal chamber 166. The lid 165a of the second embodiment of the collection container 165 is shown in FIGS. 3B-3E. A snap 165c may be included on the lid 165a (see FIG. 3E), which interlocks with a groove in the base 165b (or alternatively, a snap in the base 165b may interlock with a groove on the lid 165a) to prevent the lid 165a and base 165b from being separated during use. Additional ribs 165d or sealing rings 165e may be included on the lid 165a or the base 165b to provide a seal between the lid 165a and the base 165b. The patient port 167, vacuum port 168, and/or sensor port 169 may be provided on either the lid 165a or the base 165b of the collection container 165. Preferably, the patient port 167, vacuum port 168, sensor port 169, sensor tube 190, and fluid barrier 129 may all be provided on a lid 165a as shown in FIGS. 3A-3E.

The collection container 165 may be configured to allow the patient tube set 181 to be directly connected to the patient port 167 (as shown in the first embodiment, FIGS. 2A-2C), or preferably, the collection container 165 may be configured to allow the patient tube set 181 to connect to the patient port 167 via an adapter 300 (as shown in the second embodiment, FIGS. 3A-3E). If the patient port 167 is configured to connect to the patient tube set 181 via an adapter 300, one or more pins 167a may be included on an outer surface of the first attachment 195. The pins 167a may be able to interlock with one or more slots 329 on the adapter 300.

Wound Dressing

A wound dressing 123 may include a sterile porous substrate 131, a semipermeable adhesive cover 132, an optional inlet port 134, and a suction port 135. The porous substrate 131 may be polyurethane foam, polyvinyl alcohol foam, gauze, felt or any other suitable material. The semipermeable adhesive cover 132 may be made of a material sold under the trademark Avery Dennison® or an adhesive film product made by DermaMed®. There may be two openings in the semipermeable adhesive cover 132: an inlet port 134 and a suction port 135. Suction may be applied to the wound dressing 123 through suction port 135. Irrigation fluid may be applied to the wound dressing 123 through inlet port 134, as is further discussed in U.S. Pat. No. 7,608,066, the entirety of which is hereby incorporated by reference. If irrigation fluid is not desired, the inlet port 134 may be omitted from the wound dressing 123.

Figure 7:
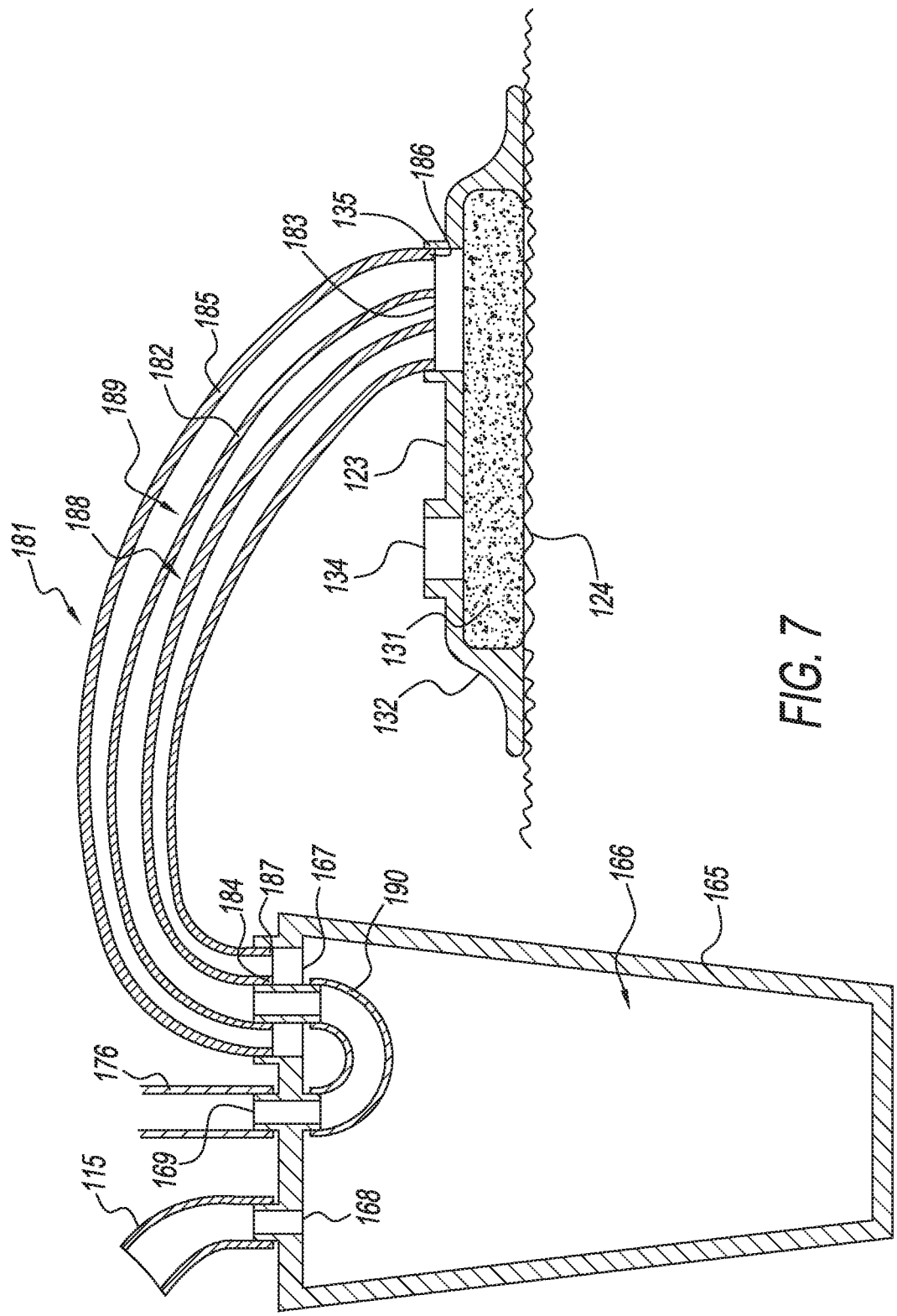
FIG. 7 shows a cross-sectional view of the collection container, wound dressing, and associated tubing shown in FIG. 6, taken along line 7.

As shown in FIG. 7, when wound dressing 123 is applied to the patient, the semipermeable adhesive cover 132 forms a seal with the patient's skin around the periphery of the wound dressing 123, thus creating a cavity enclosed by the semipermeable adhesive cover 132 and the wound 124. The periphery of the semipermeable adhesive cover 132 can be sealed to the patient's skin around the periphery of the wound. The porous substrate 131 is positioned between the wound 124 and the semipermeable adhesive cover 132. The porous substrate 131 may contact the wound 124, but because the surface of the wound 124 may be uneven, the porous substrate 131 may not contact the entire surface area of the wound 124.

When a vacuum is applied to the wound dressing 123 through the suction port 135, the vacuum is maintained in the cavity. The porous substrate 131 is provided within the cavity to distribute vacuum pressure evenly throughout the entire wound bed and prevent collapse of the cavity. The porous substrate 131 includes mechanical properties suitable for promoting the formation of granular tissue and approximating the wound margins. In addition, when vacuum is applied to wound dressing 123, porous substrate 131 creates micro- and macro-strain at the cellular level of the wound stimulating the production of various growth factors and other cytokines and promoting cell proliferation.

Patient Tube Set

Figure 6:
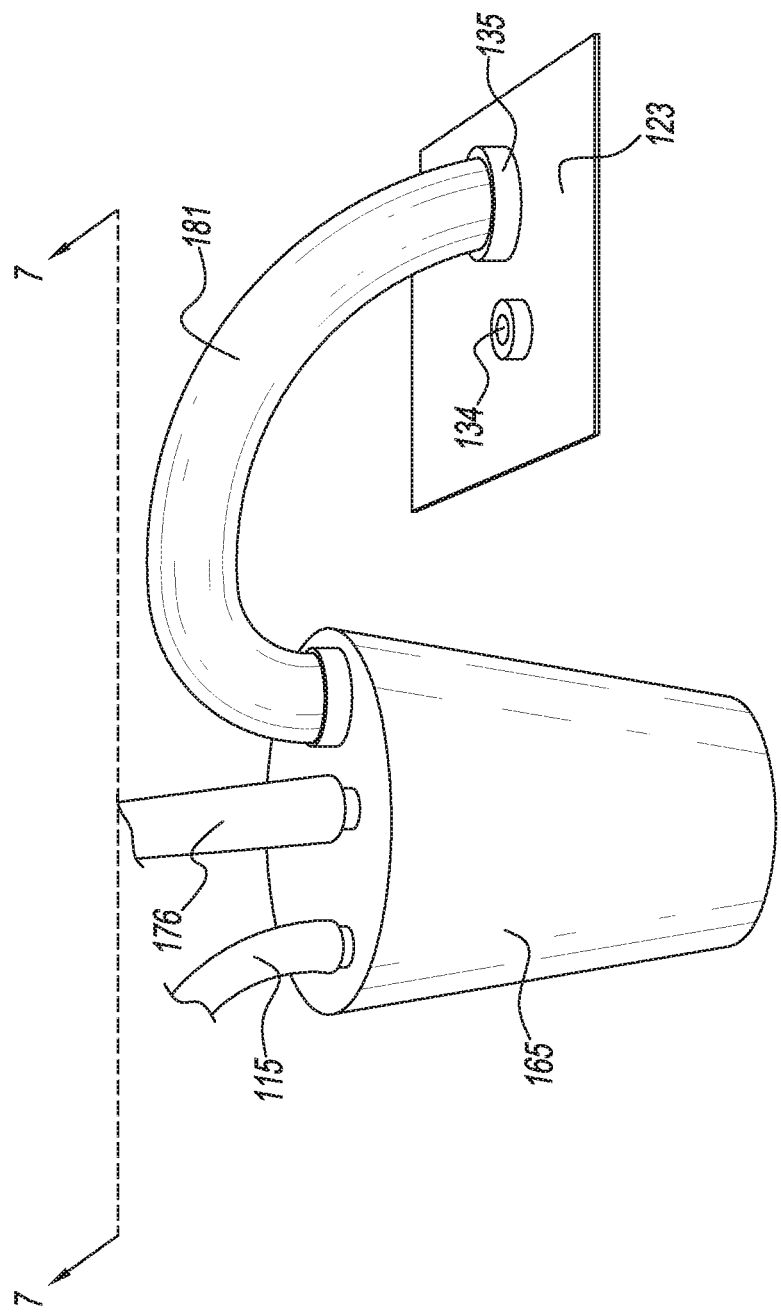
FIG. 6 shows a perspective view of a collection container, wound dressing, and associated tubing used in the negative pressure wound therapy system shown in FIGS. 1A-1C.

As shown in FIGS. 6-7, the suction port 135 of the wound dressing 123 may be pneumatically associated with the collection container 165. Further, the wound pressure sensor 173, solenoid 177, orifice restrictor 178, and adjustable restrictor 200 may be pneumatically associated with the wound dressing 123 by a patient tube set 181, typically in combination with one or more of a sensor tube 190 connecting the patient port 167 and the sensor port 169 of the collection container 165 and a tube 176 connected to the sensor port 169. The patient tube set 181 may include a fluid channel 189 that pneumatically associates wound dressing 123 with the internal chamber 166 of collection container 165 for applying suction to wound dressing 123, thereby providing a path for fluid to be moved from the wound 124 to the collection container 165. The patient tube set 181 may include a sensor channel 188 that pneumatically associates the wound dressing 123 with one or more of the wound pressure sensor 173, solenoid 177, orifice restrictor 178, and adjustable restrictor 200. The fluid channel 189 and sensor channel 188 may be formed from a plurality of tubes.

Figure 4:
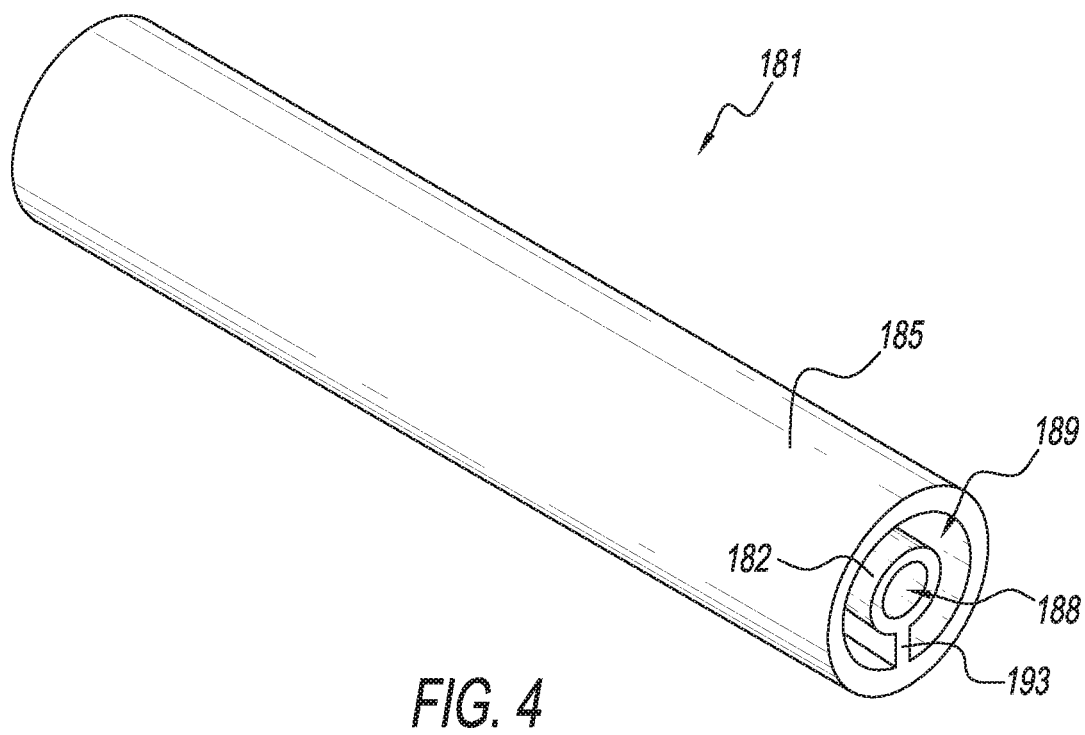
FIG. 4 shows a perspective view of a first embodiment of a patient tube set used in the negative pressure wound therapy system shown in FIGS. 1A-1C.

The patient tube set 181 may have a tube-within-a-tube design as shown in FIG. 4, including a first tube 185 and a second tube 182. Second tube 182 may be positioned inside the lumen of first tube 185 such that the second tube 182 becomes an inner tube and the first tube 185 becomes an outer tube. Second tube 182 has a patient end 183 and a device end 184. First tube 185 has a patient end 186 and a device end 187.

The second tube 182 and first tube 185 may have any cross-sectional shape, including a circle, oval, rectangle, square, or any other shape, although a substantially circular cross-sectional shape may be preferred. Preferably, the first tube 185 and the second tube 182 may have the same length. The overall length of the patient tube set 181 may vary. Patient tube sets 181 connected to the wound dressing 123 may be longer than patient tube sets 181 used to connect other components. For example, a patient tube set 181 used to connect the wound dressing 123 with a valve 500 may be longer than a patient tube set 181 used to connect the valve 500 with an adapter 300.

The patient tube set 181 may therefore include two channels. The lumen of the second tube 182 may be a sensor channel 188 which pneumatically associates the wound dressing 123 with one or more of the wound pressure sensor 173, solenoid 177, orifice restrictor 178, and adjustable restrictor 200. The space between the inner surface of the first tube 185 and the outer surface of the second tube 182 may form a fluid channel 189. The fluid channel 189 pneumatically associates wound dressing 123 with the internal chamber 166 of collection container 165.

During use, a patient tube set 181 may be connected to the suction port 135 of the wound dressing 123 and the patient port 167 of the collection container 165 as shown in FIGS. 6-7. One or both of the patient end 183 of the second tube 182 and the patient end 186 of the first tube 185 may be connected to the suction port 135 of the wound dressing 123. The device end 184 of the second tube 182 may be connected to the second attachment 194 of the patient port 167. The device end 187 of the first tube 185 may be connected to the first attachment 195 of the patient port 167. The fluid channel 189 of patient tube set 181 may be in communication with the internal chamber 166 of the collection container 165 via the fluid channel 172 of the patient port 167. The sensor channel 188 of patient tube set 181 may be in communication with sensor tube 190 via the sensor channel 171 of the patient port 167. Sensor tube 190 communicates with tube 176 via the sensor port 169 of collection container 165. Therefore, sensor channel 188 of patient tube set 181 communicates with tube 176, which communicates with one or more of the wound pressure sensor 173, solenoid 177, orifice restrictor 178, and adjustable restrictor 200. In the exemplary embodiment shown in FIG. 7, the sensor channel 188 of the patient tube set 181 does not open into the internal chamber 166 of the collection container 165; rather, the sensor channel 188 of the patient tube set 181 may be in communication with the sensor port 169 of the collection container 165 via sensor tube 190. However, other configurations are possible in which the sensor channel 188 opens into the internal chamber 166 of the collection container 165.

The patient tube set 181 may be manufactured using standard manufacturing techniques. In a preferred embodiment, the first tube 185 and the second tube 182 may be coextruded and joined by a web 193 extending between the inner surface of first tube 185 and the outer surface of second tube 182. Connecting second tube 182 and first tube 185 with a web 193 may facilitate the assembly process by ensuring that the second tube 182 and the first tube 185 remain connected. Although only one web 193 is shown in FIG. 4, a plurality of webs 193 may be used. Alternatively, first tube 185 and second tube 182 could be manufactured separately, and the second tube 182 could be inserted into the lumen of the first tube 185.

The patient tube set 181 may be made from polyvinylchloride (PVC), silicone, low density polyethylene (LDPE), polyurethane, or any other material that is flexible enough to allow the patient tube set 181 to bend, yet rigid enough that the first tube 185 and second tube 182 do not collapse if a vacuum is applied within the tubes. Preferably, the patient tube set 181 may be made from PVC. Likewise, the thicknesses of the walls of the first tube 185 and the second tube 182 may be selected such that the tubes are flexible and compliant while still providing enough structural integrity that the tubes do not collapse if a vacuum is applied within the tubes. Preferably, the thickness of the first tube 185 may be about 0.035 inches, and the thickness of the second tube 182 may be about 0.030 inches. The thickness of the web 193 may be about 0.030 inches.

Increasing the cross-sectional area of the sensor channel 188 compared to conventional designs may reduce the likelihood of fluid entering and occluding the sensor channel 188 due to capillary action. The cross-sectional area of the sensor channel 188 may be calculated based on the dimension of the inner surface of the second tube 182. For example, the cross-sectional area of a sensor channel formed by a cylindrical tube may be calculated as the area of a circle formed by the inner diameter of the tube. In some embodiments, the sensor channel 188 may have a cross-sectional area that is at least about 0.75 mm$^2$. In some embodiments, the sensor channel 188 may have a cross-sectional area in the range of between about 0.75 mm$^2$ and about 7 mm$^2$. In some embodiments, the sensor channel 188 may have a cross-sectional area of at least about 1.75 mm$^2$. In some embodiments, the sensor channel 188 may have a cross-sectional area in the range of between about 1.75 mm$^2$ and about 7 mm$^2$. In some embodiments, the sensor channel 188 may have a cross-sectional area of at least about 2.5 mm$^2$. In some embodiments, the sensor channel 188 may have a cross-sectional area in the range of about 2.5 mm$^2$ to about 7 mm$^2$. In some embodiments, the sensor channel 188 may have a cross-sectional area in the range of about 2.5 mm$^2$ to about 5 mm$^2$. In a preferred embodiment, the sensor channel 188 may have a cross-sectional area of about 3.25 mm$^2$.

However, the cross-sectional area of the sensor channel 188 could be increased until the patient tube set 181 becomes too bulky for customer acceptance.

The cross-sectional area of the fluid channel 189 of patient tube set 181 may be determined by calculating the cross-sectional area between the inner surface of first tube 185 and the outer surface of the second tube 182. For example, the cross sectional area of a fluid channel formed by the space between a cylindrical first tube and a cylindrical second tube may be determined by calculating the area of a circle formed by the inner diameter of the first tube, and subtracting the area of a circle formed by the outer diameter of the second tube. In some embodiments, the fluid channel 189 may have a cross-sectional area of at least about 10 mm$^2$. In some embodiments, the fluid channel 189 may have a cross-sectional area in the range of about 10 mm$^2$ to about 30 mm$^2$. In some embodiments, the fluid channel 189 may have a cross-sectional area of at least about 15 mm$^2$. In some embodiments, the fluid channel 189 may have a cross-sectional area in the range of about 15 mm$^2$ to about 20 mm$^2$. In a preferred embodiment, the fluid channel 189 may have a cross-sectional area of about 17.75 mm$^2$.

Generally, first tube 185 has a larger cross-sectional area compared to second tube 182 such that second tube 182 may fit inside the lumen of the first tube 185 while leaving sufficient space between the first tube 185 and the second tube 182 to create a fluid channel 189. In the case where both second tube 182 and first tube 185 are cylindrical, the inner diameter of first tube 185 may be larger than the outer diameter of the second tube 182. In some embodiments, the ratio of the cross-sectional area of the fluid channel 189 to the cross-sectional area of the sensor channel 188 may be in the range of about 4:1 to about 7:1. In some embodiments, the ratio of the cross-sectional area of the fluid channel 189 to the cross-sectional area of the sensor channel 188 may be in the range of about 5:1 to about 6:1. In a preferred embodiment, the ratio of the cross-sectional area of the fluid channel 189 to the cross-sectional area of the sensor channel 188 may be about 5.5:1.

Figure 5:
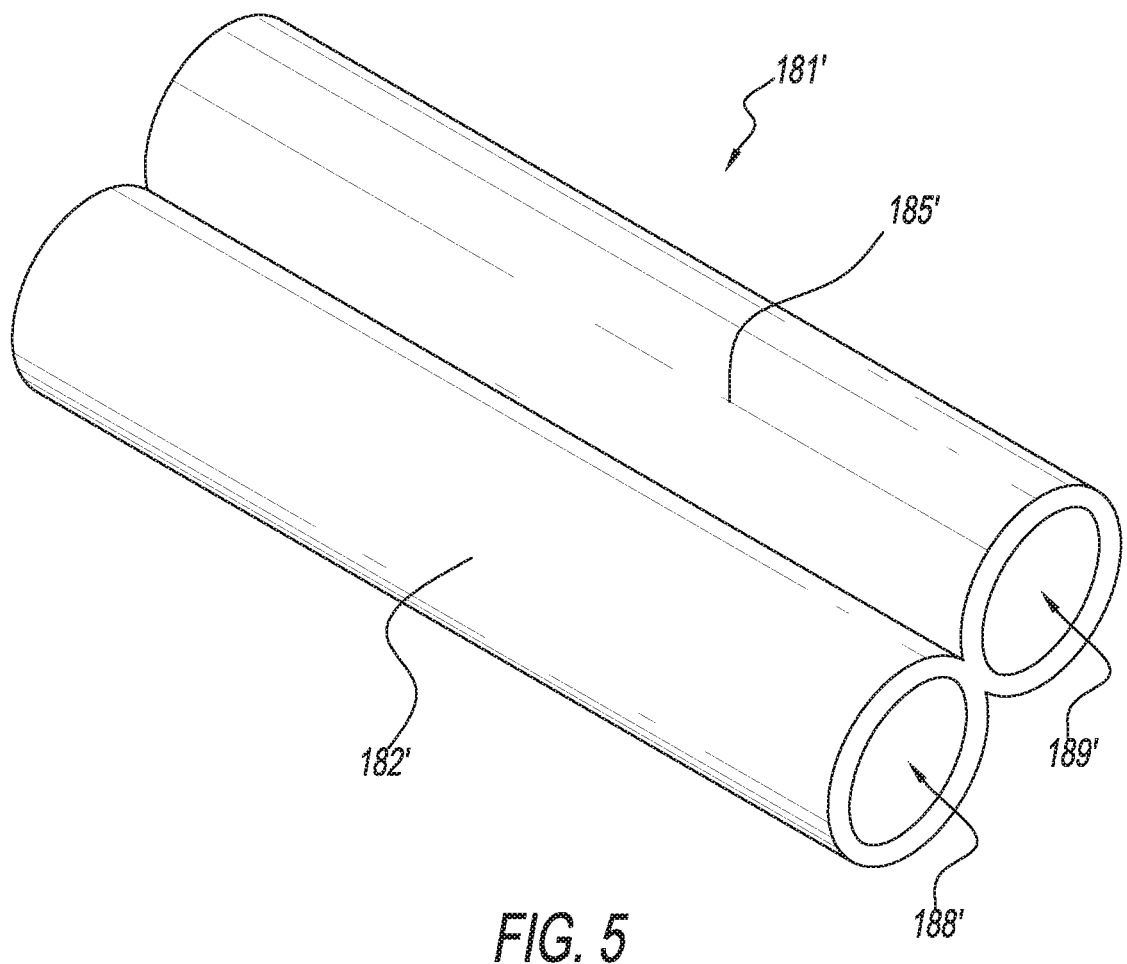
FIG. 5 shows a perspective view of a second embodiment of a patient tube set used in the negative pressure wound therapy system shown in FIGS. 1A-1C.

In an alternative embodiment of a patient tube set 181' as shown in FIG. 5, the second tube 182' and first tube 185' may be positioned side-by-side instead of positioning the second tube inside the lumen of the first tube. In patient tube set 181', the lumen of the second tube 182' would form the sensor channel 188', and the lumen of the first tube 185' would form the fluid channel 189'. In this embodiment, second tube 182' and first tube 185' may be co-extruded or second tube 182' and first tube 185' may be manufactured separately. The collection container 165 and wound dressing 123 may be modified to accommodate the different configurations of the first tube 185' and second tube 182' of patient tube set 181'. The patient port 167 of the collection container 165 and the suction port 135 of the wound dressing 123 may be modified to accommodate the side-by-side tubes. Furthermore, one or more of the second attachment 194 in the patient port 167, sensor tube 190, and the sensor port 169 of the collection container 165 may be eliminated, as the second tube 182' which forms the sensor channel 188' could connect to tube 176 without the need for to sensor tube 190 inside the collection container 165.

Although the first tube and second tube may be positioned side-by-side, the tube-within-a-tube design of the patient tube set 181 shown in FIG. 4 may be preferred because it may reduce kinking of the first tube 185 and/or the second tube 182. If the patient tube set 181 is accidentally bent, crushed, or otherwise deformed, the force may cause the first tube 185 to deform before the second tube 182 begins to deform, thereby reducing the changes of blocking the second tube 182. Furthermore, as the patient tube set 181 deforms, the second tube 182 may act as a support structure that prevents the first tube 185 from kinking and prevents the fluid channel 189 from becoming blocked. Therefore, air may flow through the fluid channel 189 and vacuum may be applied to the wound dressing 123 even if the patient tube set 181 is accidentally bent, crushed, or otherwise deformed.

The first and second tubes of the patient tube set are made of a semi-rigid material and are able to maintain their shape when a vacuum is applied by vacuum pumps 105 and 107. Therefore, the fluid channel 189 and the sensor channel 188 may be substantially unobstructed because the first and second tubes are able to resist collapsing when a vacuum is applied by vacuum pumps 105 and 107.

Patient tube set 181 may include any number of sensor channels 188. In some embodiments, patient tube set 181 may include only one sensor channel 188. In other embodiments, patient tube set 181 may include a plurality of sensor channels 188. The plurality of sensor channels 188 may be positioned inside the lumen of the first tube 185. The plurality of sensor channels 188 may be formed from a plurality of second tubes, or they may be formed from a single extrusion having multiple coaxial lumens. However, providing a plurality of sensor channels 188 may increase the overall size of the cross-section of patient tube set 181. Alternatively, if the overall size of the cross-section of patient tube set 181 is maintained and a plurality of sensor channels 188 are used, the cross-sectional area of each of the plurality of sensor channels 188 would decrease, making the sensor channels 188 more likely to occlude via capillary action. Therefore, it may be advantageous to use a patient tube set 181 with a single sensor channel 188 in order to prevent occlusions while minimizing the overall size of patient tube set 181. Using multiple sensor channels 188 requires the microcontroller 101 to determine which of the sensor channels 188 is free of occlusions and providing accurate data, and which of the sensor channels 188 is occluded and therefore providing inaccurate data. Therefore, if multiple sensor channels 188 are used, the microcontroller 101 may show an average measurement of the vacuum pressure applied across all sensor channels 188.

Standing fluid in any of the tubes connecting pumps 105 and/or 107 to the wound dressing 123 (for example, the fluid channel 189 of patient tube set 181) may create hydrostatic forces that cause a difference in the pressure experienced at the wound dressing 123 (also referred to as the therapeutic pressure) compared to the pressure being created by pumps 105 and/or 107. Depending on the position of pumps 105 and/or 107 relative to the wound, the therapeutic pressure may be increased or decreased compared to the pressure measured at pumps 105 and/or 107. However, the system 100 may be able to compensate for these variations in therapeutic pressure resulting from hydrostatic forces. The therapeutic pressure may be monitored by wound pressure sensor 173, and the activity of pumps 105 and/or 107 may be adjusted based on any pressure fluctuations. This monitoring may occur in real time, such that pumps 105 and/or 107 may be able to compensate quickly when the position of the wound changes relative to pumps 105 and/or 107.

If the vertical position of pumps 105 and/or 107 is higher than the wound, fluid in any of the tubes connecting pumps 105 and/or 107 to the wound dressing 123 (for example, the fluid channel 189 of patient tube set 181) may cause the absolute value of the therapeutic pressure applied to the wound to increase, such that a weaker vacuum is being applied to the wound. For example, if the pressure at vacuum pumps 105 and/or 107 is 70 mmHg below atmospheric pressure, the therapeutic pressure at the wound dressing 123 may be only 60 mmHg below atmospheric pressure. The increase in the absolute value of the therapeutic pressure may be detected by wound pressure sensor 173 and communicated to microprocessor 102. Control algorithm 150 contains instructions that will instruct pumps 105 and/or 107 to run, or continue to run, in order to compensate for the increase in the absolute value of the therapeutic pressure at the wound.

Conversely, if the vertical position of pumps 105 and/or 107 is lower than the wound, fluid in any of the tubes connecting pumps 105 and/or 107 to the wound dressing 123 (for example, the fluid channel 189 of patient tube set 181) may cause the absolute value of the therapeutic pressure applied to the wound to decrease, such that a stronger vacuum is being applied to the wound. For example, if the pressure at vacuum pumps 105 and/or 107 is 70 mmHg below atmospheric pressure, the therapeutic pressure at the wound dressing 123 may be 80 mmHg below atmospheric pressure. The decrease in the absolute value of the therapeutic pressure may be detected by wound pressure sensor 173. Control algorithm 150 contains instructions that will instruct pumps 105 and/or 107 to turn off, or run less frequently, in order to compensate for the decrease in the absolute value of the therapeutic pressure at the wound. Control algorithm 150 may also contain instructions to open the solenoid 177 to relieve pressure in order to compensate for the decrease in the absolute value of the therapeutic pressure at the wound, if necessary.

Adapter

Figure 12:
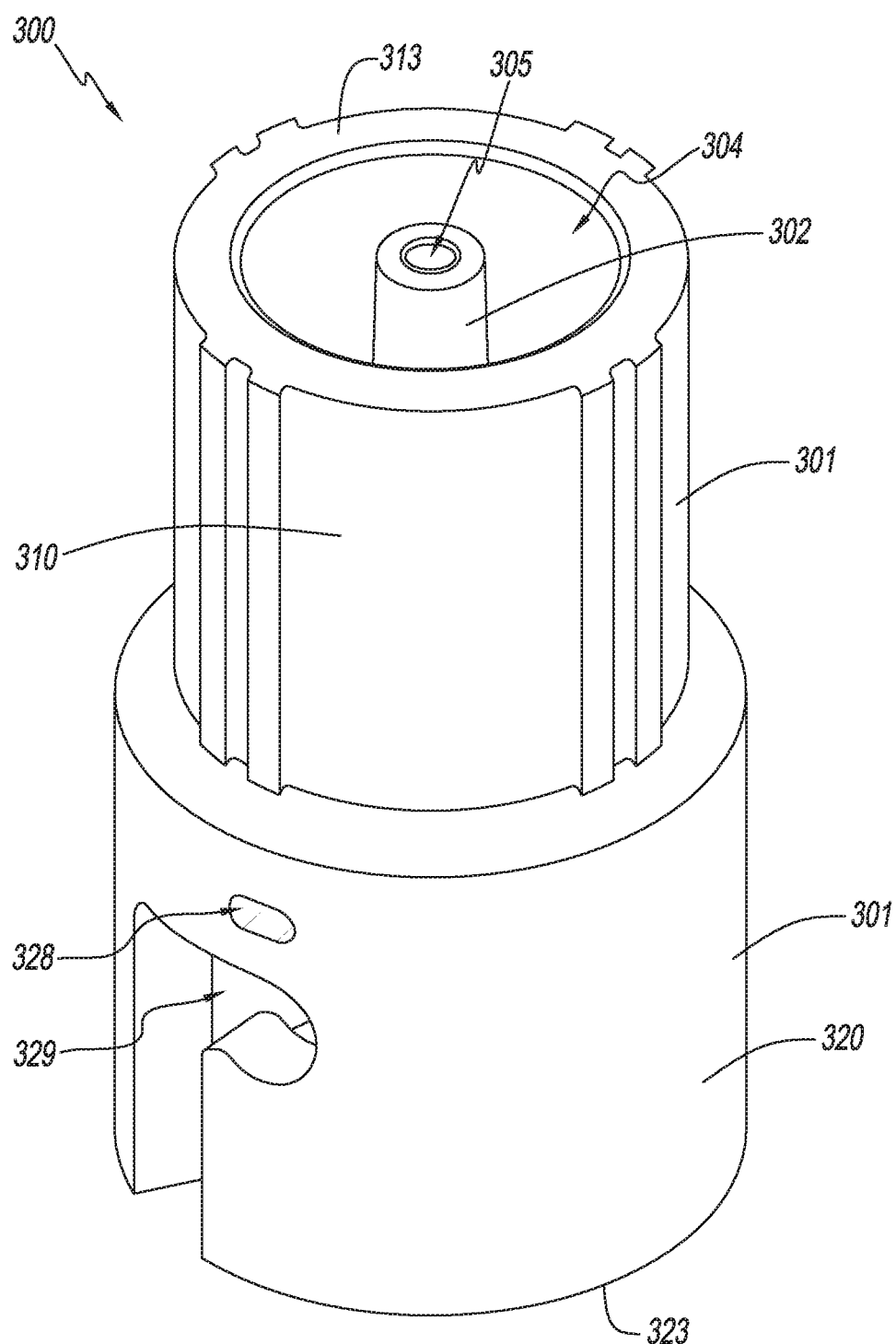
FIG. 12 shows a perspective view of an adapter used in the negative pressure wound therapy system shown in FIGS. 1B-1C.
Figure 13:
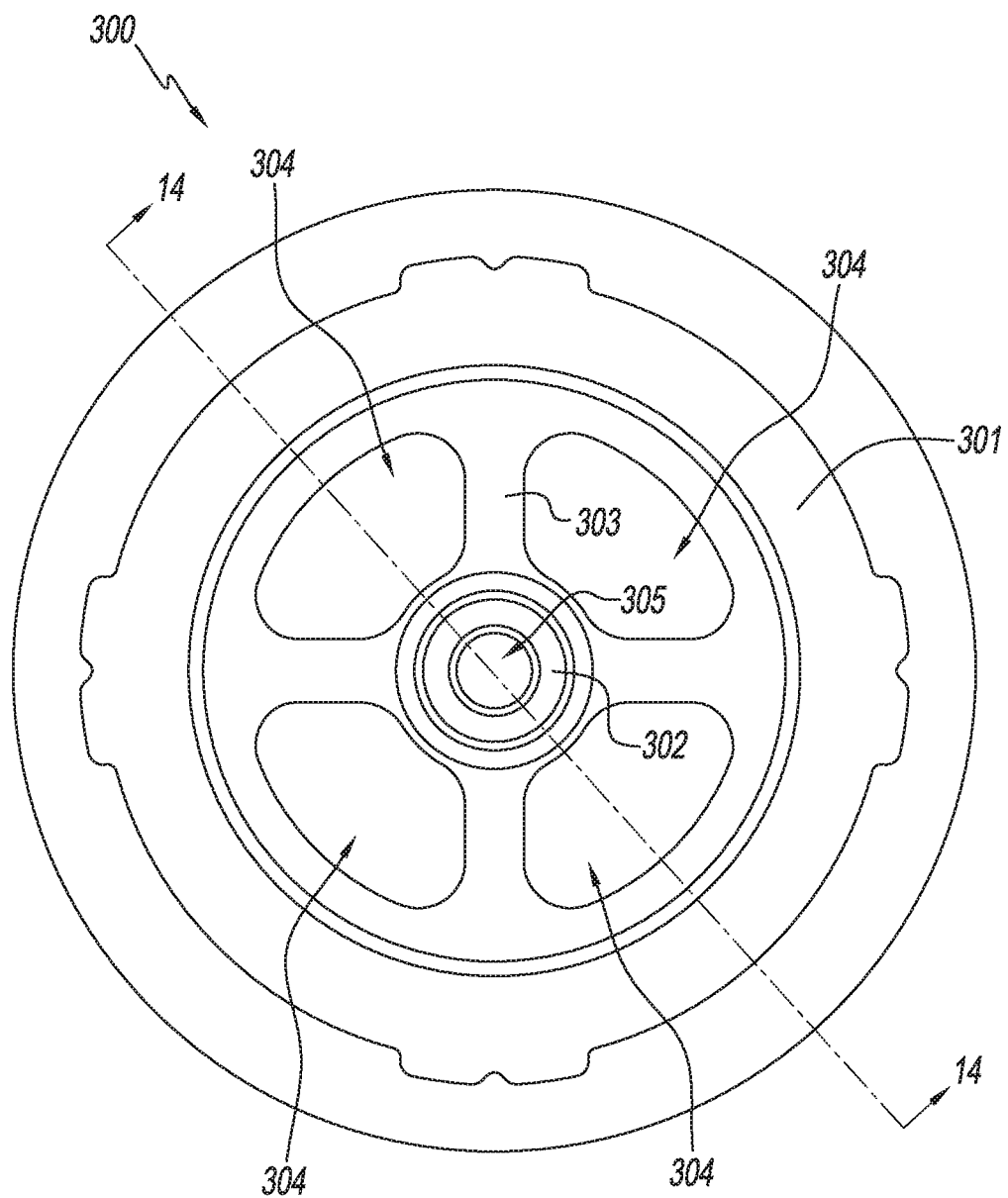
FIG. 13 shows a top view of the adapter shown in FIG. 12.
Figure 14:
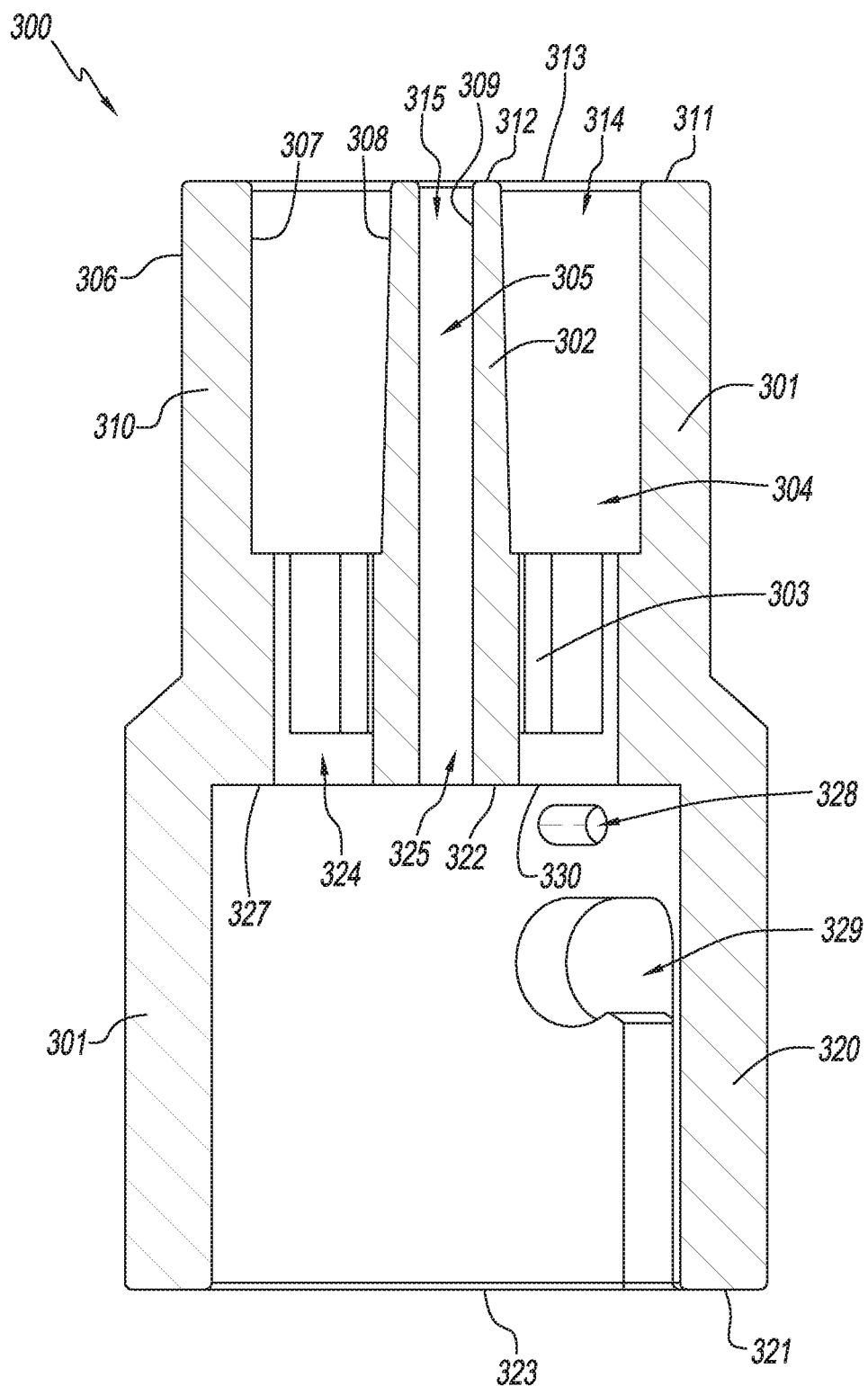
FIG. 14 shows a cross-sectional view of the adapter shown in FIGS. 12-13, taken along line 14.

An adapter 300, shown in FIGS. 12-14, may be provided on one or both ends of the patient tube set 181. Preferably, an adapter 300 may be provided on at least the device end of the patient tube set 181. The adapter 300 may have a first end 313 and a second end 323. The adapter 300 may have at least two ports: a first port 310 at the first end 313, configured to couple to a patient tube set 181, and a second port 320 at the second end 323, configured to couple to the patient port 167 of the collection container 165 and/or the second or third ports 420, 430 of a y-connector 400 (described below). The first port 310 and the second port 320 may meet at an interface 330. The second port 320, as described below, has a female fitting; however, the second port could also have a male fitting.

The adapter 300 may have an outer wall 301 and an inner wall 302 connected to the outer wall 301 by one or more webs 303. The outer wall 301 may have an outer surface 306 and an inner surface 307. The inner wall 302 may have an outer surface 308 and an inner surface 309. The outer wall 301 may extend along the first port 310 and the second port 320, having a first end 311 at the first port 310 and a second end 321 at the second port 320. The inner surface 307 of the outer wall 301 may have a larger diameter at the second port 320 and a smaller diameter at the first port 310. A horizontal ledge 327 may be formed in the outer wall 301 at the interface 330 between the first port 310 and the second port 320, where the inner surface 307 of the outer wall 301 transitions from the larger diameter at the second port 320 to the smaller diameter at the first port 310. The inner wall 302 may extend along the first port 310, having a first end 312 proximate the first end 313 of the adapter 300, and a second end 322 at the interface 330 between the first port 310 and the second port 320. The inner wall 302 does not necessarily extend into the second port 320, and preferably it may not extend into the second port 320. Preferably, the ledge 327 and the second end 322 of the inner wall 302 may be coplanar.

The inner surface 309 of the inner wall 302 may form a sensor channel 305. The sensor channel 305 may have a first opening 315 on the first end 313 of the adapter 300 and a second opening 325 at the interface 330 between the first port 310 and the second port 320. The space between the outer surface 308 of the inner wall 302 and the inner surface 307 of the outer wall 301 may form a fluid channel 304. The fluid channel 304 may have a first opening 314 on the first end 313 of the adapter 300 and a second opening 324 at the interface 330 between the first port 310 and the second port 320.

The cross-sections of the inner wall 302 and the outer wall 301 may be circular, elliptical, or various other shapes. However, in a preferred embodiment, the inner wall 302 and the outer wall 301 may both be substantially circular. More specifically, the inner surface 307 of the outer wall 301 and the outer surface 308 of the inner wall 302 may have a substantially circular cross-section. The inner surface 307 of the outer wall 301 and the outer surface 308 of the inner wall 302 may be substantially concentric.

One or more slots 329 may be provided in the outer wall 301 of the second port 320 to receive pins 167a on the first attachment 195 of the patient port 167. One or more notches 328 may also be provided in the outer wall 301 at the second port 320 to receive pins 390 on the gasket 380.

Figure 15A:
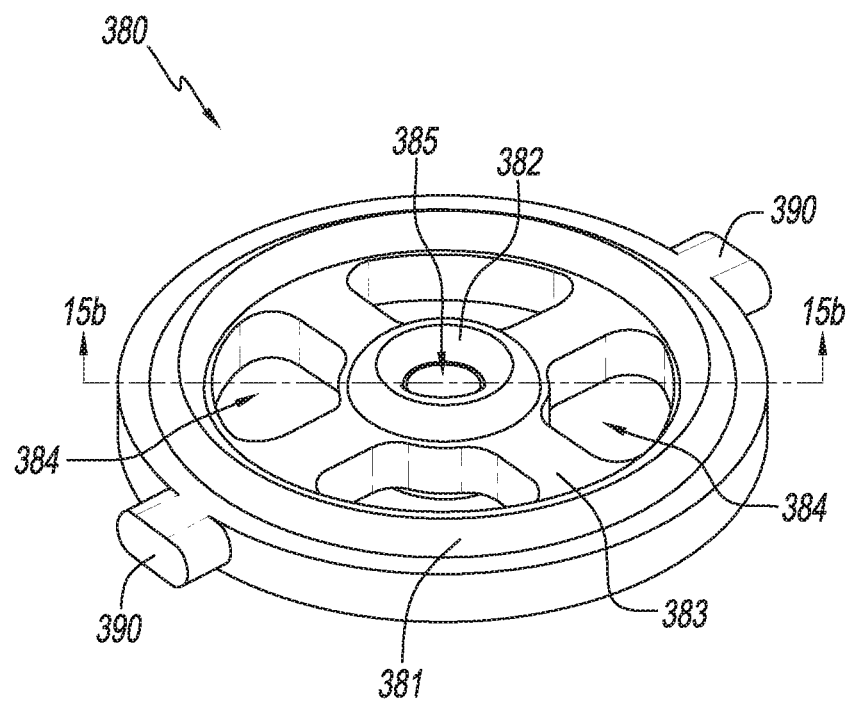
FIG. 15A shows a perspective view of a gasket used in the negative pressure wound therapy system shown in FIGS. 1B-1C.
Figure 15B:
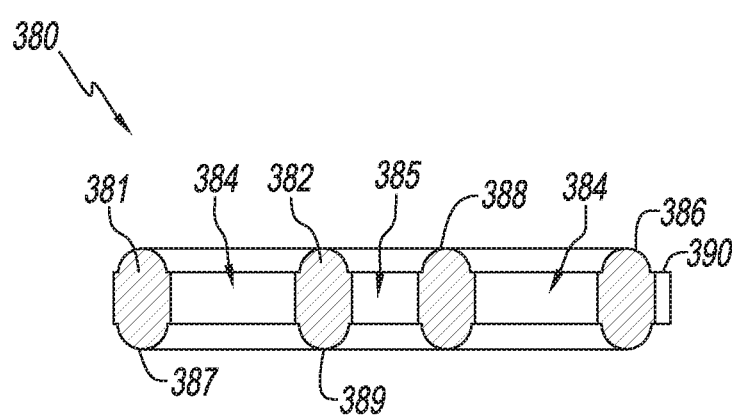
FIG. 15B shows a cross-sectional view of the gasket shown in FIG. 15A, taken along line 15b.

A gasket 380, shown in FIGS. 15A-15B, may be provided with the adapter 300. The gasket 380 may include an outer sealing rib 381 and an inner sealing rib 382 connected to the outer sealing rib 381 by one or more webs 383. The outer sealing rib 381 may have a cross-sectional shape similar to the cross-sectional shape of the ledge 327 on the outer wall 301 of the adapter 300. The inner sealing rib 382 may have a cross-sectional shape that is similar to the cross-sectional shape of the second end 322 of the inner wall 302 of the adapter 300. The inner diameter of the inner sealing rib 382 may form a sensor channel 385, and the space between the outer sealing rib 381 and the inner sealing rib 382 may form a fluid channel 384. Preferably, the cross-sections of the inner sealing rib 382 and the outer sealing rib 381 may be substantially circular, and even more preferably they may be substantially concentric.

The gasket 380 may have a first surface and a second surface opposite the first surface, such that the outer sealing rib 381 has a first surface 386 and a second surface 387, and the inner sealing rib 382 has a first surface 388 and a second surface 389. The gasket 380 may have one or more pins 390 extending outwardly from the outer sealing rib 381. Preferably, there may be the same number of pins 390 on the gasket 380 and notches 328 in the adapter 300. The gasket 380 may be made of any number of materials, including silicone, thermoplastic elastomers, natural rubber, or any other elastomeric, compressible, non-porous material. In a preferred embodiment, the gasket 380 may be made of silicone.

The gasket 380 may be inserted into the second port 320 of the adapter 300. The pins 390 on the gasket 380 may be inserted into the notches 328 in the adapter 300. The first surface 386 of the outer sealing rib 381 of the gasket 380 may be in contact with the ledge 327 on the outer wall 301 of the adapter 300. Likewise, the first surface 388 of the inner sealing rib 382 of the gasket 380 may be in contact with the second end 322 of the inner wall 302 of the adapter 300. The sensor channel 385 of the gasket 380 may be aligned with the sensor channel 305 of the adapter 300. Each second opening 324 of the fluid channel 304 of the adapter 300 may be aligned with a fluid channel 384 in the gasket 380. In order to provide a continuous path for fluids passing through the fluid channels 304, 384 of the adapter 300 and the gasket 380, the pins 390 may be positioned on the gasket 380 to allow the webs 383 on the gasket 380 to substantially overlie the webs 303 on the adapter 300.

A patient tube set 181 may be connected to the first port 310 of the adapter 300. The device end 187 of the first tube 185 may mate with the outer wall 301 of the adapter 300. Preferably, the outer surface of the first tube 185 may be in contact with the inner surface 307 of the outer wall 301. The device end 184 of the second tube 182 may mate with the inner wall 302 of the adapter 300. Preferably, the inner diameter of the second tube 182 may be in contact with the outer surface 308 of the inner wall 302. Thus, the fluid channel 304 of the adapter 300 may be in communication with the fluid channel 189 of the patient tube set 181. The sensor channel 305 of the adapter 300 and the sensor channel 385 of the gasket 380 may be in communication with the sensor channel 188 of the patient tube set 181.

Figure 16A:
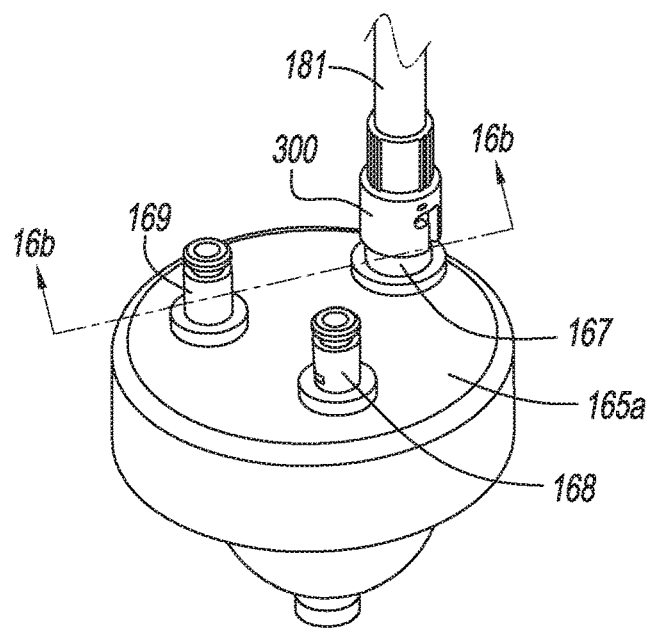
FIG. 16A shows a perspective view of the adapter shown in FIG. 12 connected to the lid shown in FIG. 3B.
Figure 16B:
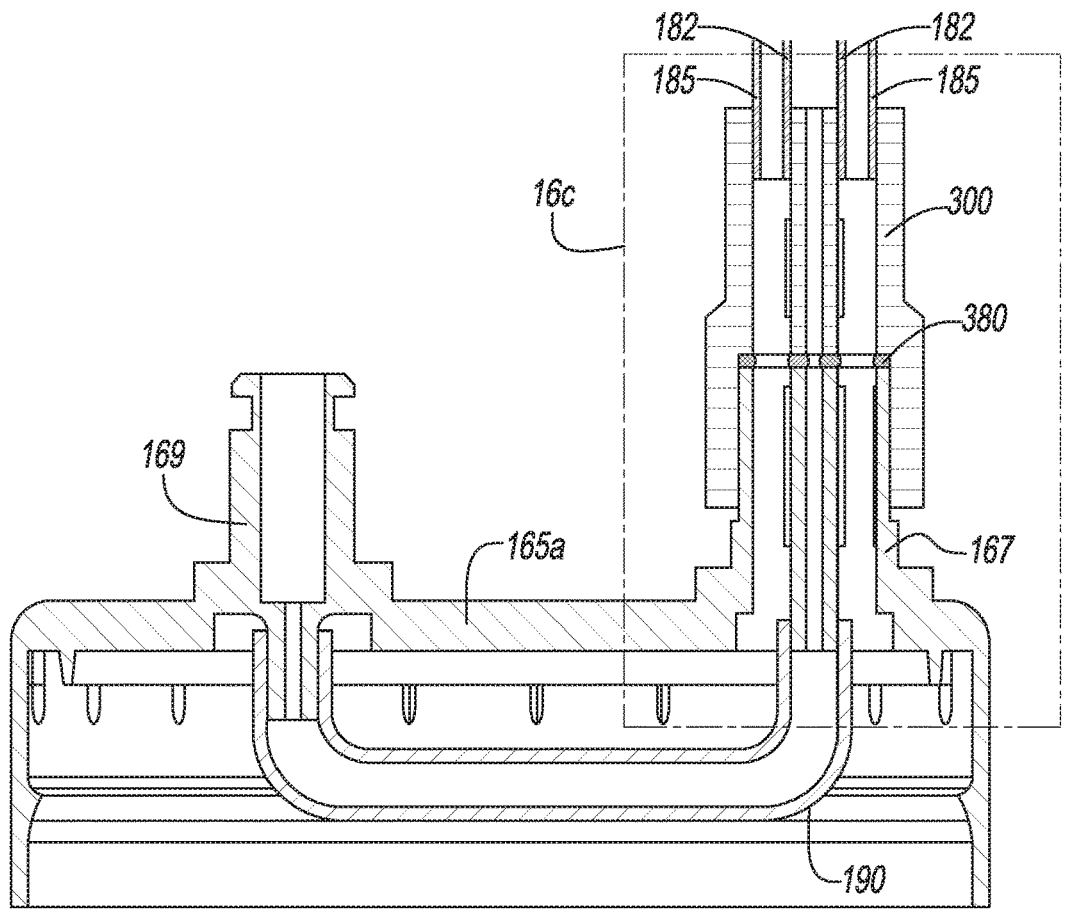
FIG. 16B shows a cross-sectional view of the lid and adapter shown in FIG. 16A, taken along line 16b, and further includes the gasket shown in FIG. 15A (which is not visible in FIG. 16A).
Figure 16C:
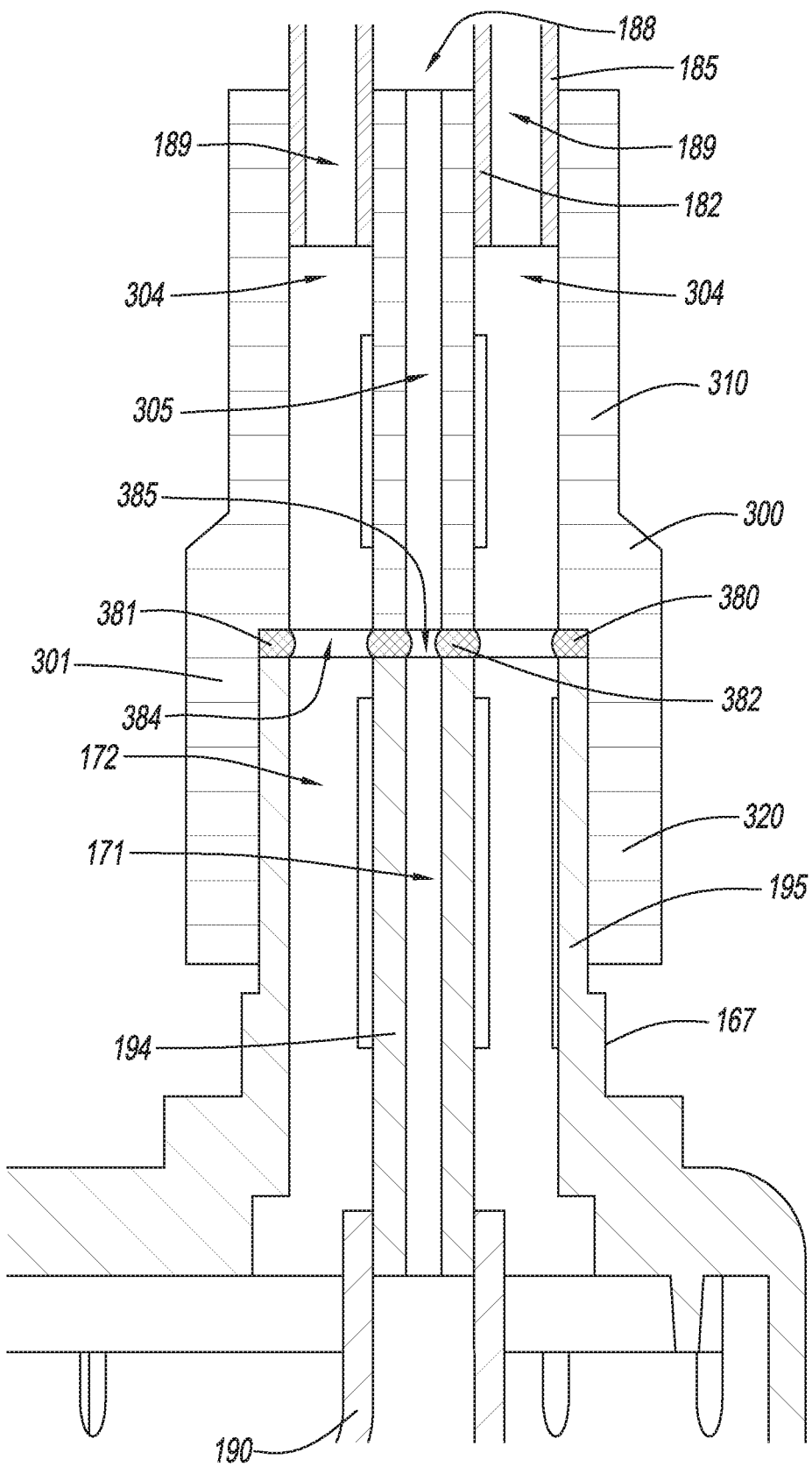
FIG. 16C shows a detailed cross-sectional view of the lid, adapter, and gasket shown in FIG. 16B.
Figure 17:
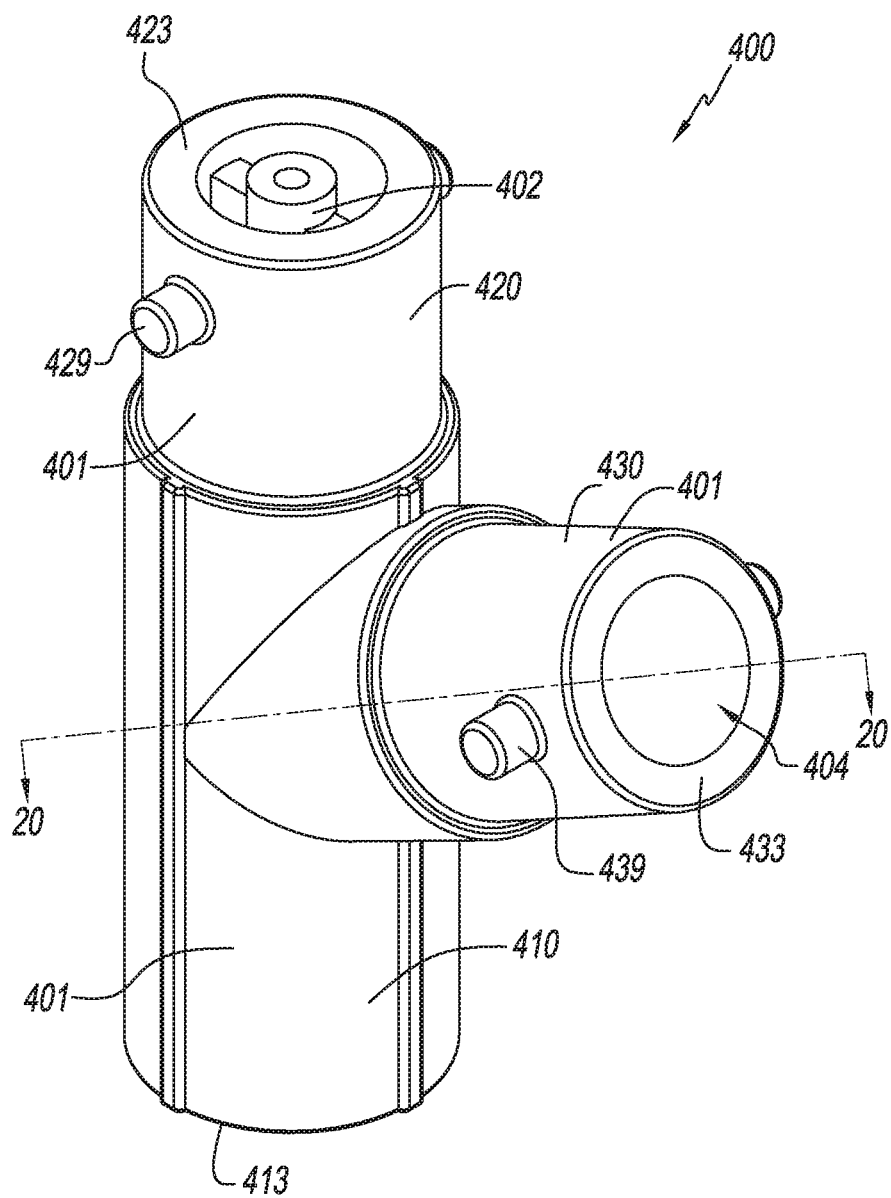
FIG. 17 shows a perspective view of a y-connector used in the negative pressure wound therapy system shown in FIG. 1C.
Figure 18:
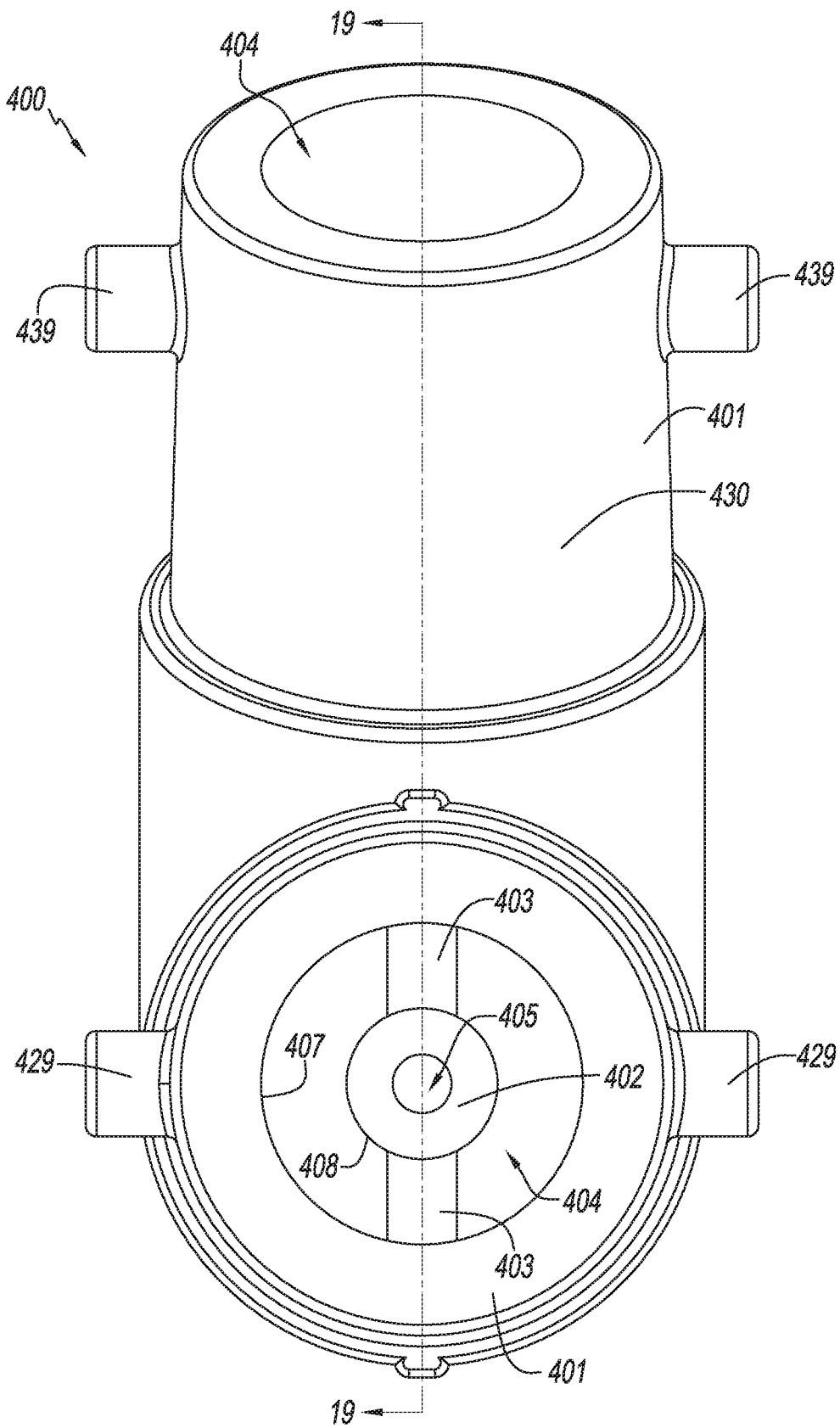
FIG. 18 shows a top view of the y-connector shown in FIG. 17.

The second port 320 of the adapter 300 may be connected to the patient port 167 of the collection container 165, as shown in FIGS. 16A-16C. The patient port 167 may be inserted into the outer wall 301 of the second port 320 of the adapter 300. The pins 167a on the patient port 167 may be inserted into the slots 329 in the outer wall 301 of the adapter 300. The gasket 380, positioned in the second port 320 of the adapter 300, may provide for sealing engagement between the second port 320 of the adapter 300 and the patient port 167 of the collection container 165. The ledge 327 on the outer wall 301 of the adapter 300 may be in sealing engagement with the first attachment 195 of the patient port 167 via the outer sealing rib 381 on the gasket 380. The second end 322 of the inner wall 302 of the adapter 300 may be in sealing engagement with the second attachment 194 of the patient port 167 via the inner sealing rib 382 on the gasket 380.

Thus, if the adapter 300 is connected to both a patient port 167 on a collection container 165 and a patient tube set 181, as shown in FIGS. 16A-16C, the sensor channel 188 of patient tube set 181 may be in communication with the sensor channel 171 of the patient port 167, and the fluid channel 189 of patient tube set 181 may be in communication with the fluid channel 172 of the patient port 167. Using an adapter may be preferred because it may simplify the user set-up process by allowing the user to connect the adapter 300 to the patient port 167 of the collection container 165, as shown in FIGS. 16A-16C, instead of individually connecting first tube 185 and second tube 182 to the patient port 167, as shown in FIG. 7.

Pump Pressure Sensor

Pump pressure sensor 109 may be pneumatically associated with first vacuum pump 105 and an optional second vacuum pump 107 as shown in FIGS. 1A-1C. Pump pressure sensor 109 may be electrically associated with microcontroller 101 through electrical cable 110. Pump pressure sensor 109 provides a vacuum-pressure signal to the microprocessor 102 enabling control algorithm 150 to monitor the vacuum pressure at the outlet of vacuum pumps 105 and/or 107.

Wound Pressure Sensor

A wound pressure sensor 173 may be pneumatically associated with the sensor port 169 of the collection container 165 through a tube 176 as shown in FIGS. 6-7. Tube 176 may be a single lumen tube as shown in FIG. 7. Because tube 176 is pneumatically associated with the wound dressing 123 via one or more of the sensor tube 190 and the sensor channel 188 in the patient tube set 181, the wound pressure sensor 173 is able to monitor the therapeutic pressure in the wound dressing 123 more accurately than the pump pressure sensor 109 can. Wound pressure sensor 173 may be electrically associated with microcontroller 101 through electrical cable 174 and provides a vacuum-pressure signal to microprocessor 102 enabling control algorithm 150 to monitor the therapeutic pressure at the wound site.

Solenoid/Valve

A solenoid 177 and optional orifice restrictor 178 may be pneumatically associated with the sensor port 169 of the collection container 165 through tube 176 as shown in FIGS. 1A-1C. If the orifice restrictor 178 is not provided, solenoid 177 may connected to tube 176 by "T" connector 175. If the orifice restrictor 178 is provided, the orifice restrictor 178 may be connected to tube 176 by a "T" connector 175, and vacuum-pressure relief solenoid 177 may be connected to the orifice restrictor 178. Together, the solenoid 177 and optional orifice restrictor 178 act to relieve pressure in the wound dressing 123 and in the collection container 165 in the event of an alarm condition, if the set pressure is decreased (during intermittent mode, for example), or if power is turned off. Solenoid 177 may be, for example, one available under the trademark Pneutronics®, or Air Logic®. Solenoid 177 is electrically associated with, and controlled by, microprocessor 102 through electrical cable 130. Solenoid 177 may be configured to vent vacuum to atmosphere when the power is turned off, for example. Orifice restrictor 178, if it is provided, is positioned in line with solenoid 177 and tube 176 to regulate the rate at which vacuum is relieved to atmospheric pressure when solenoid 177 is de-energized. Orifice restrictor 178 is, for example, available under the trademark Air Logic®.

Adjustable Restrictor

As shown in FIGS. 1A-1C, an optional adjustable restrictor 200 may be pneumatically associated with tube 176. Two embodiments of an adjustable restrictor 200 are shown in greater detail in FIGS. 8-11, and include a cap 210, a body 220, and a porous material 230. Cap 210 has a base 211 and a flange 213. The base 211 and/or flange 213 of cap 210 has at least one hole 212 that opens to the atmosphere to allow air to enter the body 220 and create a controlled air leak in the system 100. Flange 213 has a threaded portion 214 that engages the body 220. Body 220 includes at least one tube port 221 and a threaded port 223. The threaded port 223 on the body 220 engages the threaded portion 214 of the cap 210, thereby coupling the cap 210 and the body 220.

The porous material 230 may be positioned between the threaded port 223 on the body 220 and the base 211 of the cap 210. The porous material 230 may be compressible. The porous material 230 may have minimal water absorbency (i.e., hydrophobic), which may prevent the flow rate of the air leak from changing when the restrictor 200 is exposed to increased or decreased humidity. A number of common filter materials may be used, including plastic foams, or synthetic membrane materials such as those used in cigarette filters. The porous material 230 may be disc-shaped and may cover the hole 212 on cap 210.

Air enters the adjustable restrictor 200 at the hole 212 in the cap 210 to create the air leak. Air then travels through the porous material 230 before entering the body 220 of the adjustable restrictor 200 via the threaded port 223. The flow rate of the air leak may be controlled by compressing or decompressing the porous material 230. Compressing the porous material 230 by tightening the connection between the body 220 and the cap 210 decreases the flow rate of the air leak. Decompressing the porous material 230 by loosening the connection between the body 220 and the cap 210 increases the flow rate of the air leak.

Figure 8:
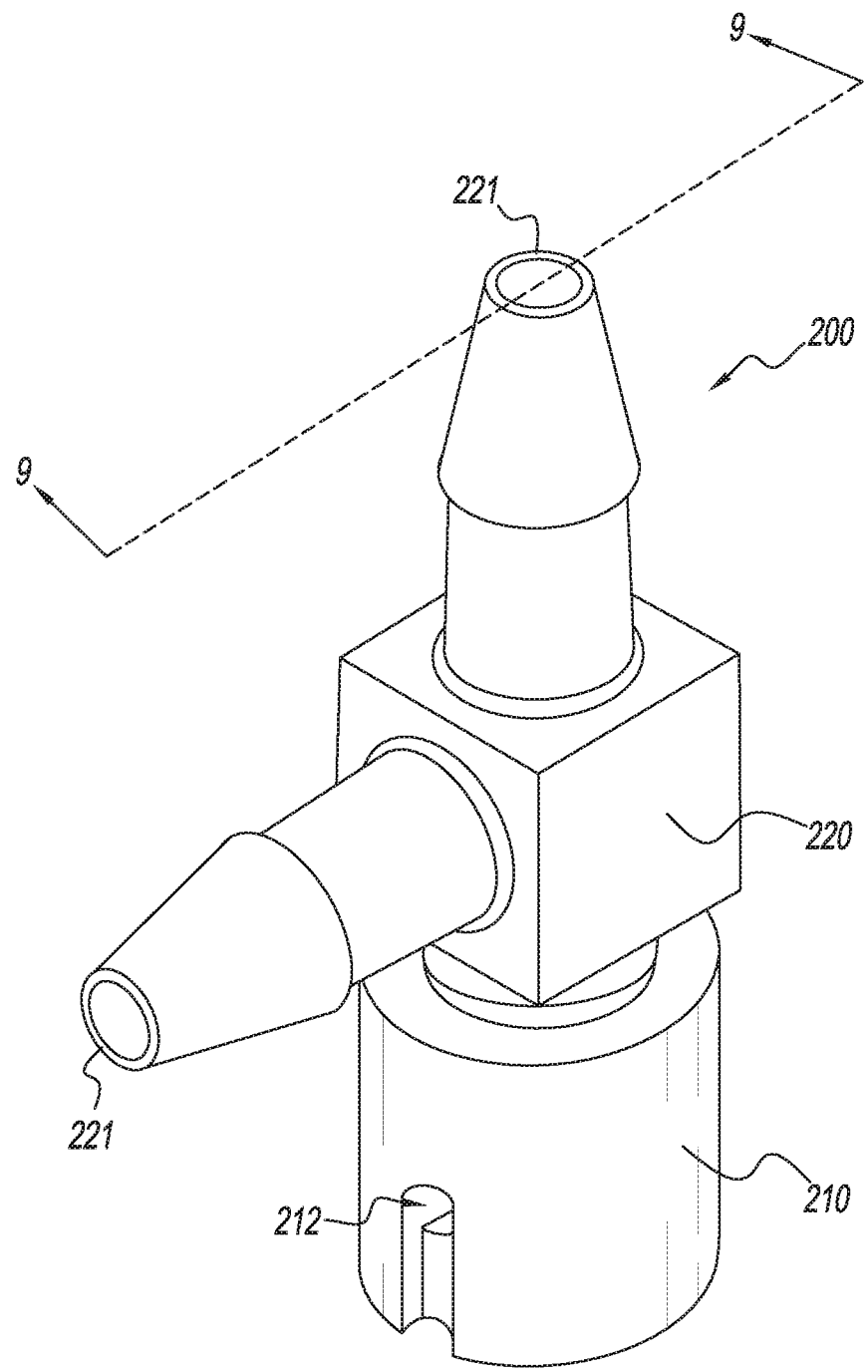
FIG. 8 shows a perspective view of a first embodiment of an adjustable restrictor used in the negative pressure wound therapy system shown in FIGS. 1A-1C.
Figure 9:
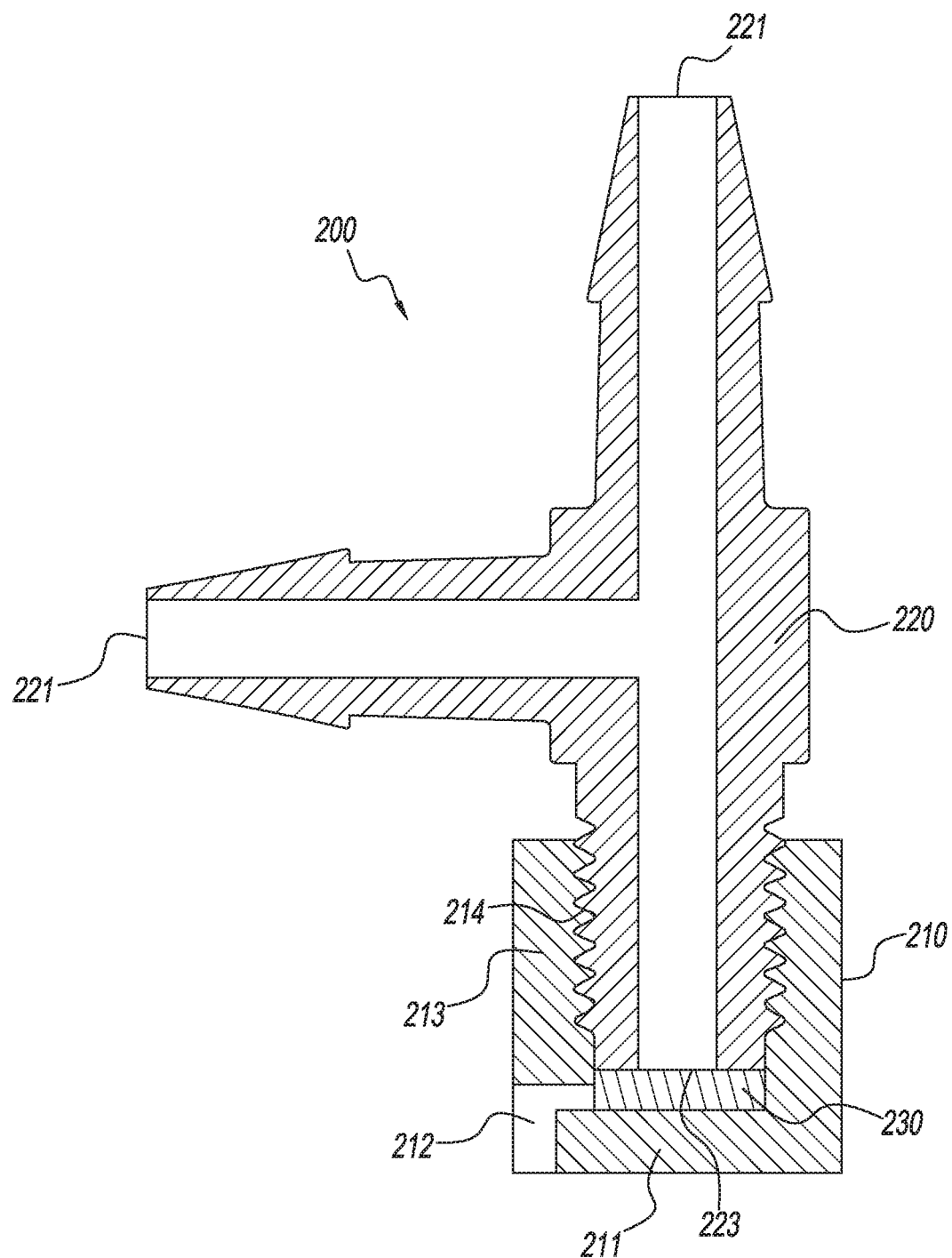
FIG. 9 shows a cross-sectional view of the adjustable restrictor shown in FIG. 8, taken along line 9.
Figure 10:
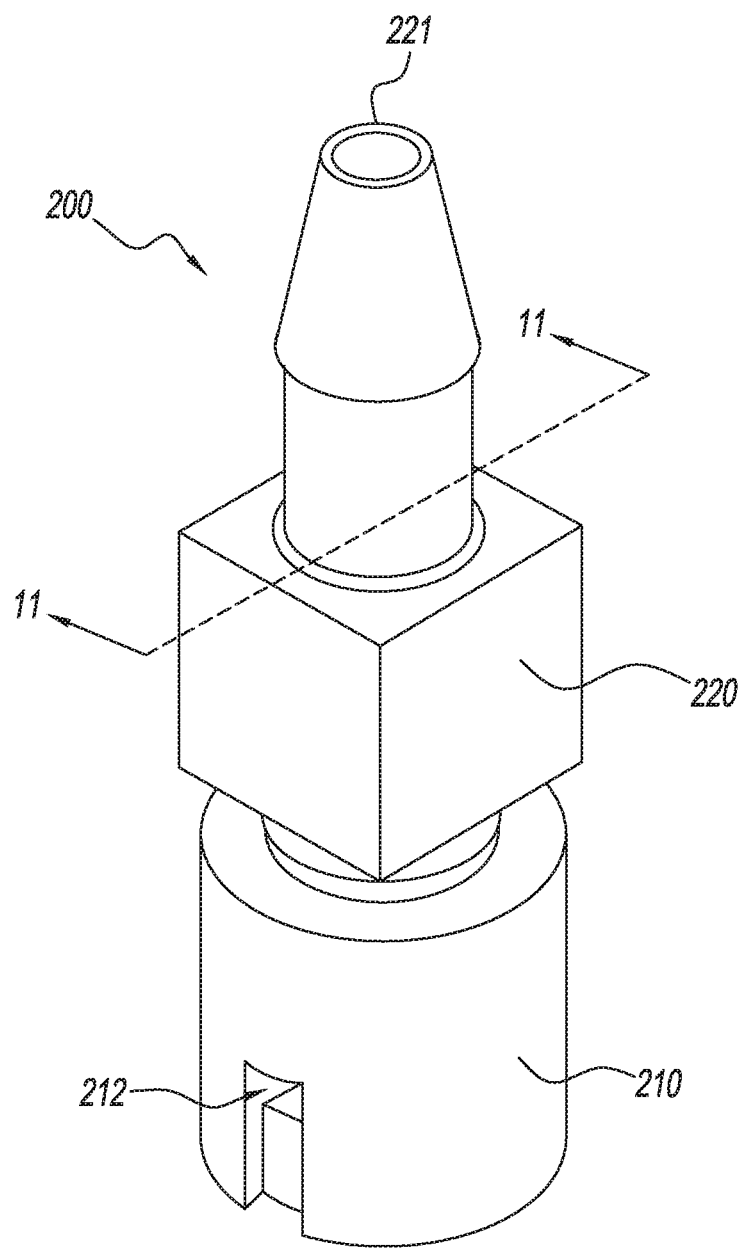
FIG. 10 shows a perspective view of a second embodiment of an adjustable restrictor used in the negative pressure wound therapy system shown in FIGS. 1A-1C.
Figure 11:
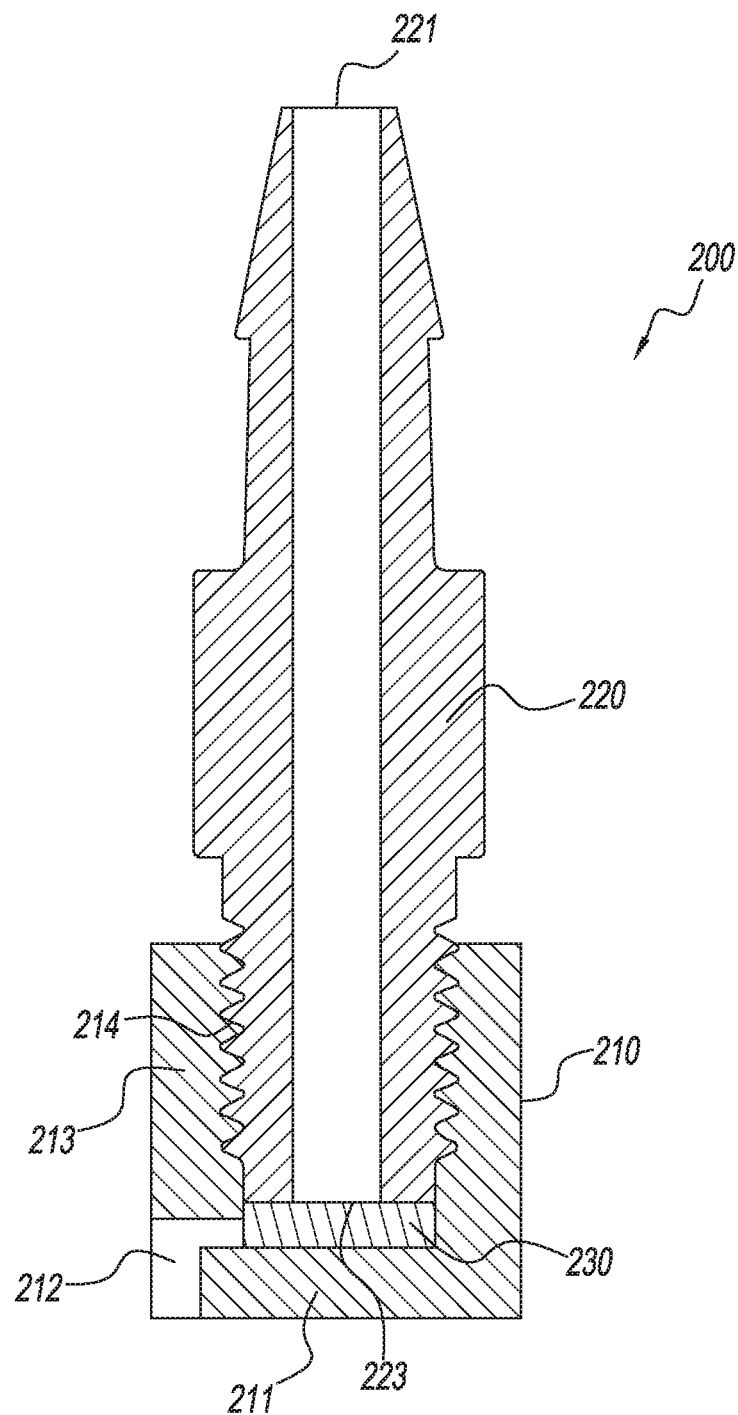
FIG. 11 shows a cross-sectional view of the adjustable restrictor shown in FIG. 10, taken along line 11.

In one embodiment shown in FIGS. 8-9, adjustable restrictor 200 may include two tube ports 221. If two tube ports 221 are provided, adjustable restrictor 200 may be positioned in line with tube 176, and a "T" connector may not be needed to connect adjustable restrictor 200 to tube 176. In another embodiment shown in FIGS. 10-11, adjustable restrictor may include only one tube port 221 which may be connected to tube 176 by a "T" connector 191 as shown in FIGS. 1A-1C.

Adjustable restrictor 200 may be designed to create an air leak that allows air to flow into tube 176. Because sensor channel 188 of the patient tube set 181 is pneumatically associated with tube 176, the air leak also allows air to flow into the sensor channel 188 towards wound dressing 123, thereby preventing occlusions in the sensor channel 188. Any fluid that may have entered the sensor channel 188 (through capillary action, for example) is pushed toward the wound dressing 123, and fluid from the wound dressing 123 is prevented from flowing into the sensor channel 188 due to the pressure gradient. Furthermore, the air leak in the sensor channel 188 may cause air to flow into the fluid channel 189 at the suction port 135 of the wound dressing 123. The air leak would therefore provide a force that is additive to the suction force being supplied by pumps 105 and/or 107 to ensure fluid does not enter sensor channel 188 or remove occlusions from sensor channel 188. In addition, air from the air leak may flow out of the patient end 183 of the second tube 182 and into the patient end 186 of the first tube 185, thereby providing a force that is additive to the suction force being supplied by pumps 105 and/or 107 to ensure that fluid in the fluid channel 189 would be forced toward the collection container 165. An advantage of using the adjustable restrictor 200 is that the air leak may be substantially uninterrupted when a vacuum is applied to collection container 165 and/or wound dressing 123, such that the air leak may continually prevent occlusions and help to clear otherwise stationary fluid from the sensor channel 188 and/or fluid channel 189, instead of only acting in a reactive manner after an occlusion has formed.

The flow rate of the air leak should be low enough such that the air leak does not substantially affect the therapeutic pressure being applied to the wound dressing 123, causing a leak alarm to be triggered. The flow rate of the air leak should be low enough that pumps 105 and/or 107 are able to compensate for the small increase in the absolute value of the pressure in system 100 resulting from the leak. Therefore, the therapeutic pressure applied to the wound dressing 123 may be substantially maintained despite the air leak. For example, the leak may have a flow rate ranging from 0.05-0.1 liters per minute.

Alternatively, instead of using the adjustable restrictor 200, an air leak may be created by sporadically opening the solenoid 177, thereby venting tube 176 to atmosphere such that air flows from solenoid 177 through tube 176, through one or more of sensor tube 190 and sensor channel 188 of patient tube set 181 toward wound dressing 123. Any occlusions in the sensor channel 188 of patient tube set 181 may be forced toward wound dressing 123, and any fluid in the fluid channel 189 of patient tube set 181 may be forced toward collection container 165. In this case, the solenoid 177 may function as a time-variable restrictor.

Y-Connector

A y-connector 400, shown in FIGS. 17-20, may be provided to allow two patient tube sets 181 connected to two separate wound dressings 123 to be connected to the same patient port 167 of the collection container 165. The y-connector 400 may have a first end 413, a second end 423, and a third end 433. The y-connector 400 may have at least three ports: a first port 410 at the first end 413, configured to connect to the collection container 165, and second and third ports 420, 430 at the second and third ends 423, 433, configured to connect to the two separate wound dressings 123. The second and third ports 420, 430, as described below, have male fittings; however they could also have female fittings.

Figure 19:
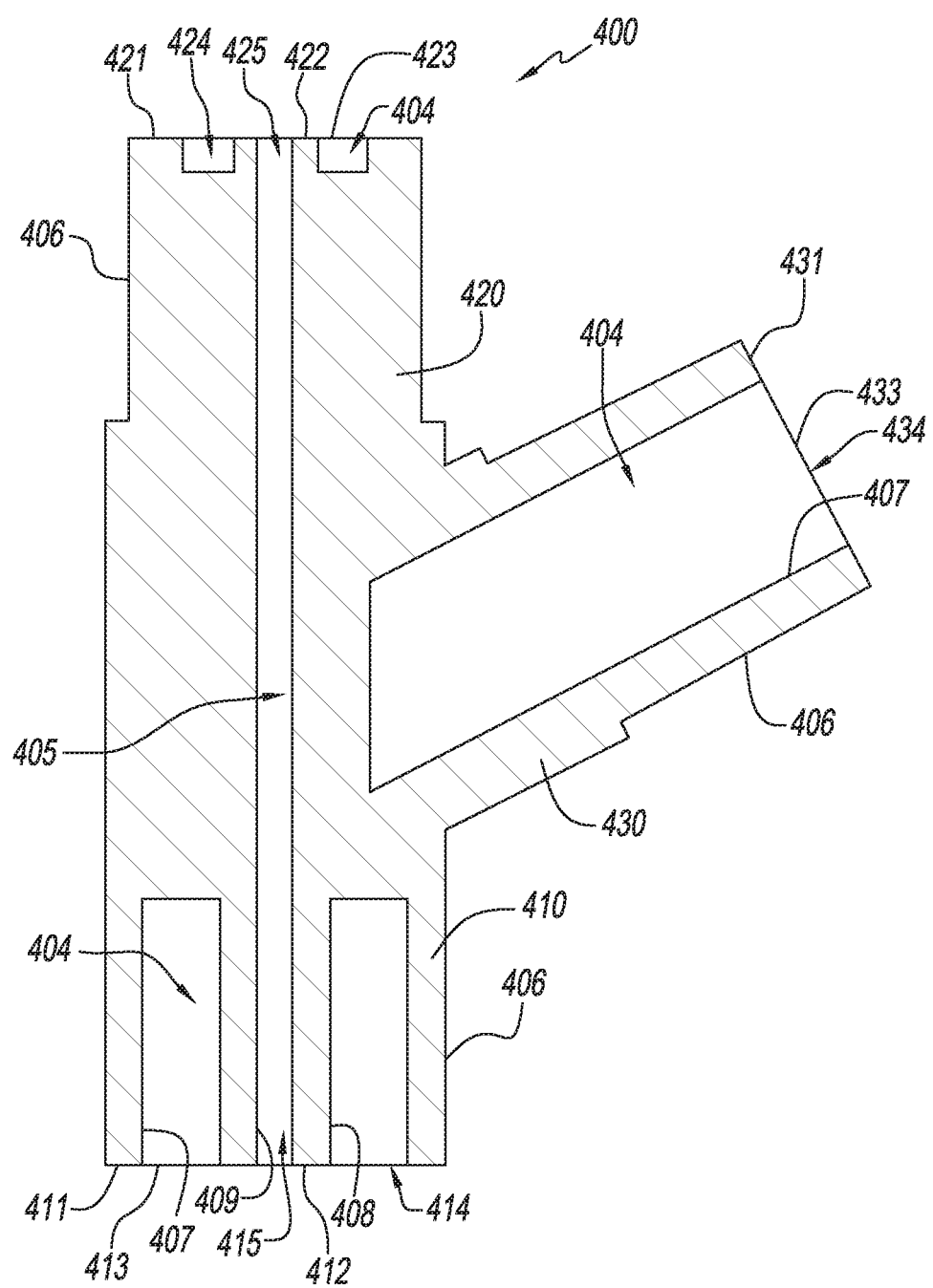
FIG. 19 shows a cross-sectional view of the y-connector shown in FIGS. 17-18, taken along line 19.
Figure 20:
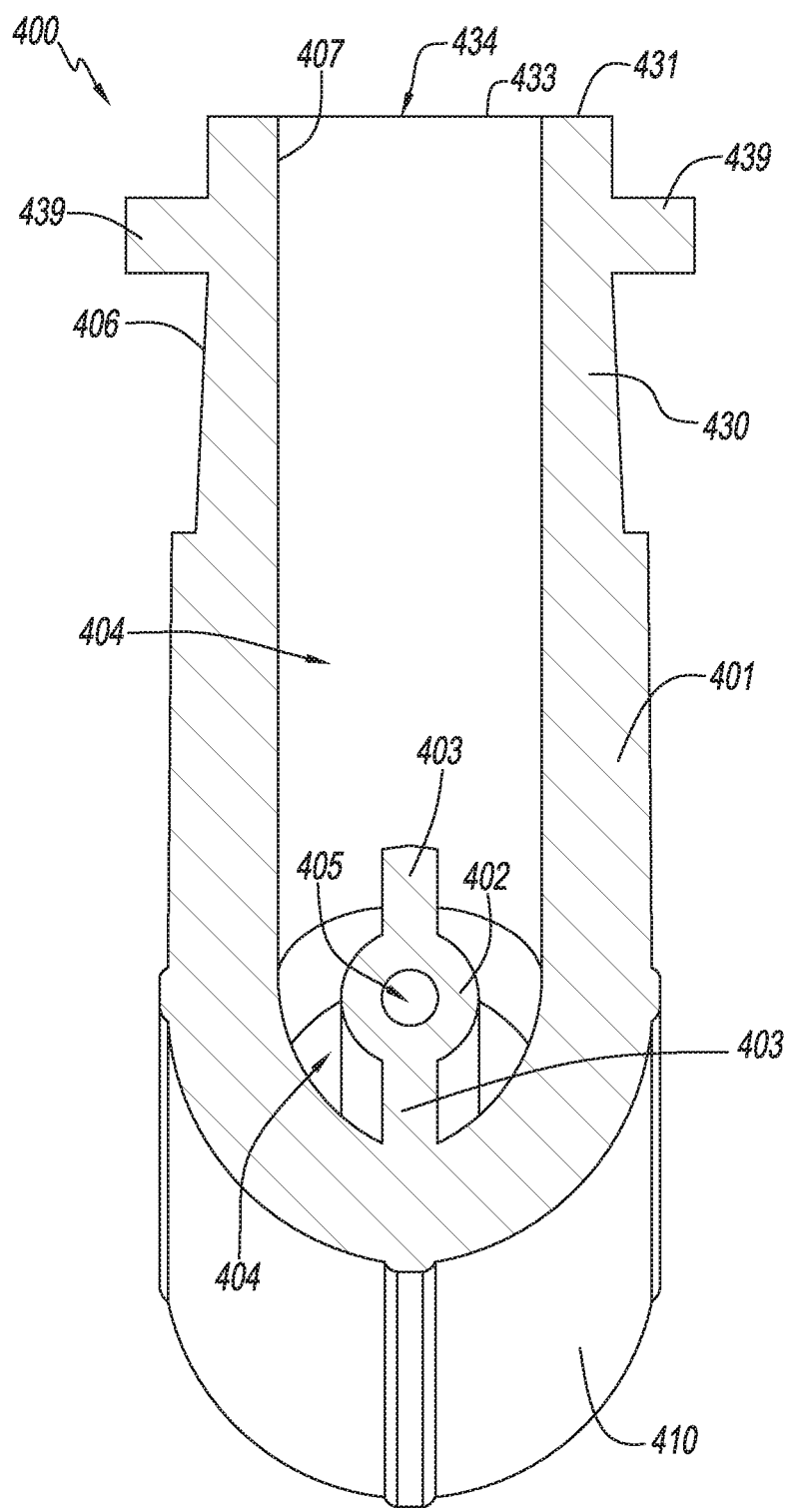
FIG. 20 shows a cross-sectional view of the y-connector shown in FIG. 17, taken along line 20.

The y-connector 400 may have an outer wall 401 and an inner wall 402 connected to the outer wall 401 by one or more webs 403. The outer wall 401 may have an outer surface 406 and an inner surface 407. The inner wall 402 may have an outer surface 408 and an inner surface 409. The outer wall 401 may extend along all three ports, having a first end 411 at the first end 413 of the y-connector 400, a second end 421 at the second end 423 of the y-connector 400, and a third end 431 at the third end 433 of the y-connector 400. The inner wall 402 may extend along two of the ports, having a first end 412 at the first end 413 of the y-connector 400 and a second end 422 at the second end 423 of the y-connector 400, as shown in FIG. 19.

The inner surface 409 of the inner wall 402 may form a sensor channel 405 that extends from a first opening 415 on the first port 410 to a second opening 425 on the second port 420. A fluid channel 404 may extend into all three ports, having a first opening 414 at the first port 410, a second opening 424 at the second port 420, and a third opening 434 at the third port 430. The fluid channel 404 in the first port 410 and the second port 420 may be formed by the space between the outer surface 408 of the inner wall 402 and the inner surface 407 of the outer wall 401. The fluid channel 404 in the third port 430 may be formed by the inner surface 407 of the outer wall 401.

The cross-sections of the inner wall 402 and the outer wall 401 may be circular, elliptical, or various other shapes. However, in a preferred embodiment, the inner wall 402 and the outer wall 401 may both be substantially circular. More specifically, the inner surface 407 of the outer wall 401 and the outer surface 408 of the inner wall 402 may have a substantially circular cross-section. The inner surface 407 of the outer wall 401 and the outer surface 408 of the inner wall 402 may be substantially concentric.

Any of the first port 410, second port 420, and third port 430 may be designed to connect to a patient tube set 181 directly, or indirectly using an adapter 300. In a preferred embodiment, the y-connector 400 may be designed such that the first port 410 directly connects with a patient tube set 181, while the second port 420 and third port 430 each connect with a patient tube set 181 via an adapter 300.

A patient tube set 181 may be connected to the first port 410 of the y-connector 400. The patient end 186 of the first tube 185 may mate with the outer wall 401 of the y-connector 400. Preferably, the outer surface of the first tube 185 may be in contact with the inner surface 407 of the outer wall 401. The patient end 183 of the second tube 182 may mate with the inner wall 402 of the y-connector 400. Preferably, the inner surface of the second tube 182 may be in contact with the outer surface 408 of the inner wall 402. Thus, the fluid channel 404 of the y-connector 400 may be in communication with the fluid channel 189 of the patient tube set 181. The sensor channel 405 of the y-connector 400 may be in communication with the sensor channel 188 of the patient tube set 181.

In some embodiments, the second port 420 and third port 430 of the y-connector 400 interface with an adapter 300 connected to a patient tube set 181. The second port 320 of the adapter 300 may be connected to the second port 420 or the third port 430 of the y-connector 400. The second or third port 420, 430 of the y-connector 400 may be inserted into the outer wall 301 of the second port 320 of the adapter 300. The second and third ports 420, 430 of the y-connector 400 may each have one or more pins 429, 439 on the outer wall 401 that may be inserted into the slots 329 in the adapter 300. The gasket 380, positioned in the second port 320 of the adapter 300, may provide for sealing engagement between the second port 320 of the adapter 300 and the second or third port 420, 430 of the y-connector 400.

If the adapter 300 is being connected to the second port 420 of the y-connector 400 (which includes an outer wall 401 and an inner wall 402), the ledge 327 on the outer wall 301 of the adapter 300 may be in sealing engagement with the second end 421 of the outer wall 401 of the y-connector 400 via the outer sealing rib 381 on the gasket 380. The second end 322 of the inner wall 302 of the adapter 300 may be in sealing engagement with the second end 422 of the inner wall 402 of the y-connector 400 via the inner sealing rib 382 on the gasket 380.

If the adapter 300 is being connected to the third port 430 of the y-connector 400 (which may include an outer wall 401 but not in inner wall 402), the ledge 327 on the outer wall 301 of the adapter 300 may be in sealing engagement with the second end 431 of the outer wall 401 of the y-connector 400 via the outer sealing rib 381 on the gasket 380. The second end 322 of the inner wall 302 of the adapter 300 may not be in sealing engagement with the y-connector 400.

When patient tube sets 181 are connected to each of the first, second, and third ports 410, 420, 430 of the y-connector 400, the fluid channels 189 of the patient tube sets 181 connected to the second and third ports 420, 430 communicate with the fluid channel 404 of the y-connector 400. The sensor channel 188 of the patient tube set 181 connected to the second port 420 of the y-connector 400 (into which the inner wall 402 extends) communicates with the sensor channel 405 of the y-connector 400. However, the sensor channel 188 of the patient tube set 181 connected to the third port 430 of the y-connector 400 (into which the inner wall 402 does not extend) communicates with the fluid channel 404 of the y-connector 400.

When using a y-connector 400, it is preferable that the sensor channel 405 extends from the first port 410 to only one of the second port 420 or the third port 430. As described above and shown in FIGS. 17-20, the sensor channel 405 may extend from the first port 410 to the second port 420, but not to the third port 430. If the sensor channel 405 of the y-connector 400 also extended into the third port 430, the wound pressure sensor 173 may only detect a blockage when the patient tube sets 181 connected to the second and third ports 420, 430 of the y-connector 400 were both occluded. If a blockage or occlusion occurred in only one of the patient tube sets 181 connected to the second and third ports 420, 430 of the y-connector 400, the wound pressure sensor 173 would still detect the vacuum from the unoccluded patient tube set 181, and the blockage alarm would not be triggered. Therefore, it may be advantageous for the y-connector 400 to have a sensor channel 405 extending between only the first port 410 and the second port 420. In this configuration, the wound pressure sensor 173 may detect a blockage if the patient tube set 181 connected to the second port 420 of the y-connector 400 was occluded and the patient tube set 181 connected to the third port 430 of the y-connector 400 was not occluded, or if the patient tube sets 181 connected to the second and third ports 420, 430 of the y-connector 400 were both occluded.

Alternatively, instead of providing the y-connector 400 and the adapter 300 as separate components, they may be formed as a single component. In this case, patient tube sets 181 may be connected to the second and third ports 420, 430, and the first port 410 may be integrated with the second port 320 of the adapter 300. The outer wall 301 of the second port 320 of the adapter 300 may be continuous with the outer wall 401 of the first port 410 of the y-connector 400, and the inner wall 302 of the second port 320 of the adapter 300 may be continuous with the inner wall 402 of the first port 410 of the y-connector 400. Potential methods for manufacturing a combined y-connector 400 and adapter 300 may include 3D printing or molding.

Valve

At certain points during use, it may be desirable to close the fluid channel 189 and/or the sensor channel 188 of the patient tube set 181, thereby preventing vacuum pressures from being transmitted along the channel. For example, it may be desirable to close the fluid channel 189 and sensor channel 188 when replacing a collection container 165 while maintaining the wound dressing 123 over the wound, or when troubleshooting leaks and blockages in the system 100. As discussed above, the patient tube set 181 may be resistant to kinking, which may beneficially prevent the fluid channel 189 from becoming occluded if the patient tube set 181 is accidentally bent, crushed, or otherwise deformed. However, as a result, the user may not be able to close the fluid channel 189 using conventional means such as a clamp.

Therefore, in order to close the fluid channel 189 and/or the sensor channel 188, a valve 500 may be connected in-line with the patient tube set 181 to allow the user to occlude the fluid channel 189 and/or the sensor channel 188 when desired. The valve 500 may include a valve housing 510, a slide switch 550, a valve seat 570, a first indicator band 501, and a second indicator band 502.

The valve housing 510 may have a longitudinal axis 516 and a transverse axis 515 substantially perpendicular to the longitudinal axis 516. The valve housing 510 may have a first longitudinal end 512, a second longitudinal end 513, a first transverse end 517, and a second transverse end 518. A channel 514 may extend from the first longitudinal end 512 toward the second longitudinal end 513 along the longitudinal axis 516. One or more grooves 519 may extend longitudinally along the inner surface of the channel 514, starting at the second longitudinal end 513. Preferably, the one or more grooves 519 do not extend all the way to the first longitudinal end 512 of the housing 510.

A first port 520 and a second port 530 may be included on the valve housing 510. The first port 520 and second port 530 may be provided at the first transverse end 517 and second transverse end 518 of the valve housing 510, respectively. The first and second ports 520, 530 may each include an outer wall 521, 531 and an inner wall 522, 532 connected to the outer wall 521, 531 by a web 523, 533. A web 523, 533 may extend between the inner wall 522, 532 and the outer wall 521, 531 along a line substantially parallel to the longitudinal axis 516 of the valve housing 510. The inner surface of the inner wall 522, 532 may form a sensor channel 525, 535. A fluid channel 524, 534 may be formed by the space between the outer surface of the inner wall 522, 532 and the inner surface of the outer wall 521, 531. Preferably, the first and second ports 520, 530 may both be substantially parallel with the transverse axis 515.

The first and second ports 520, 530 may be connected to patient tube sets 181 by mating the outer wall 521, 531 with the first tube 185 and the inner wall 522, 532 with the second tube 182.

The valve housing 510 may alternatively be formed together with an adapter 300 to form a single component. In this case, a patient tube set 181 may be connected to the first port 520, and the second port 530 of the valve housing 510 may be connected with the second port 320 of the adapter 300. The outer wall 301 of the second port 320 of the adapter 300 may be continuous with the outer wall 531 of the second port 530 of the valve housing 510, and the inner wall 302 of the second port 320 of the adapter 300 may be continuous with the inner wall 532 of the second port 530 of the valve housing 510. Potential manufacturing techniques may include 3D printing or molding.

Figure 32:
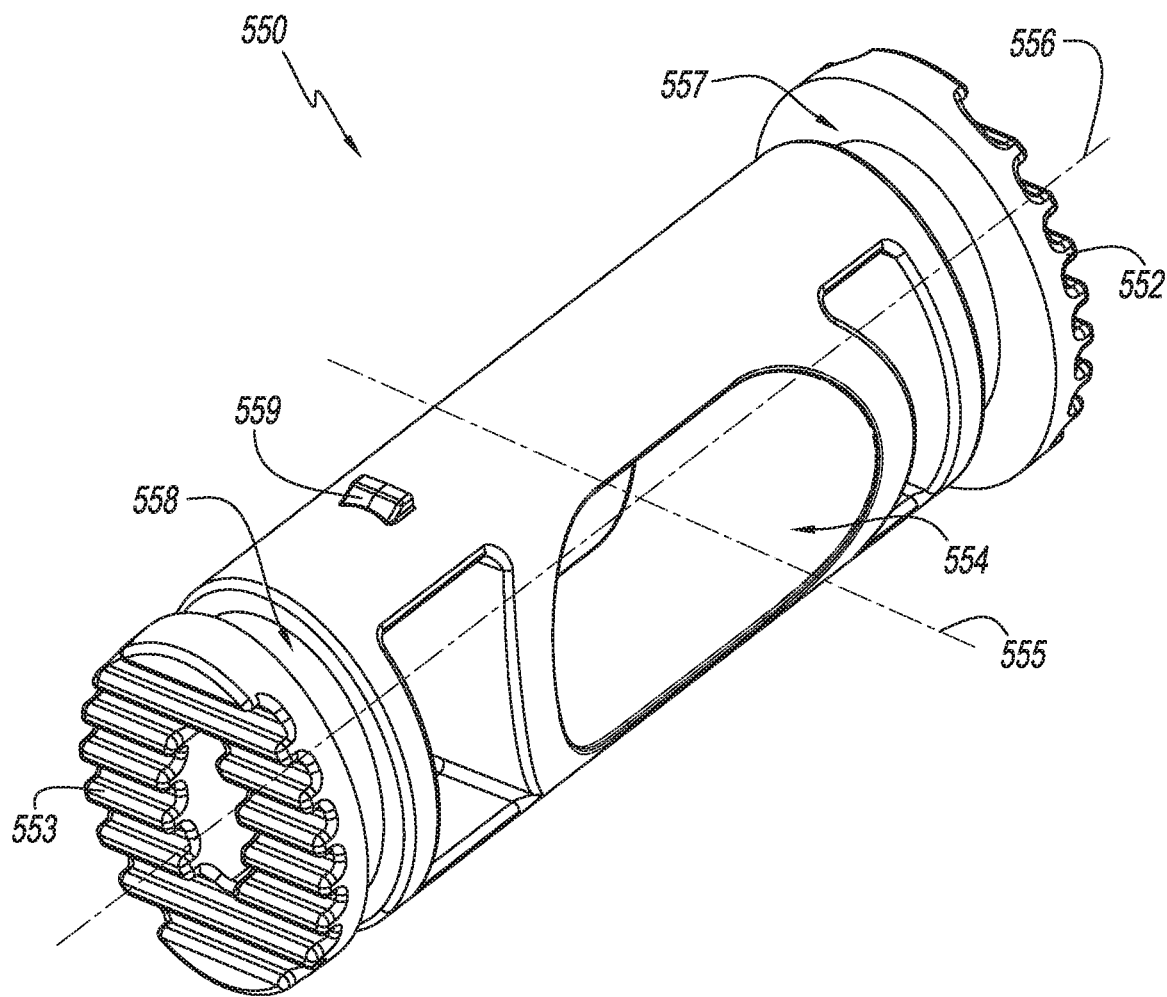
FIG. 32 shows a perspective view of a slide switch used in the valve of FIGS. 21-28.
Figure 33:
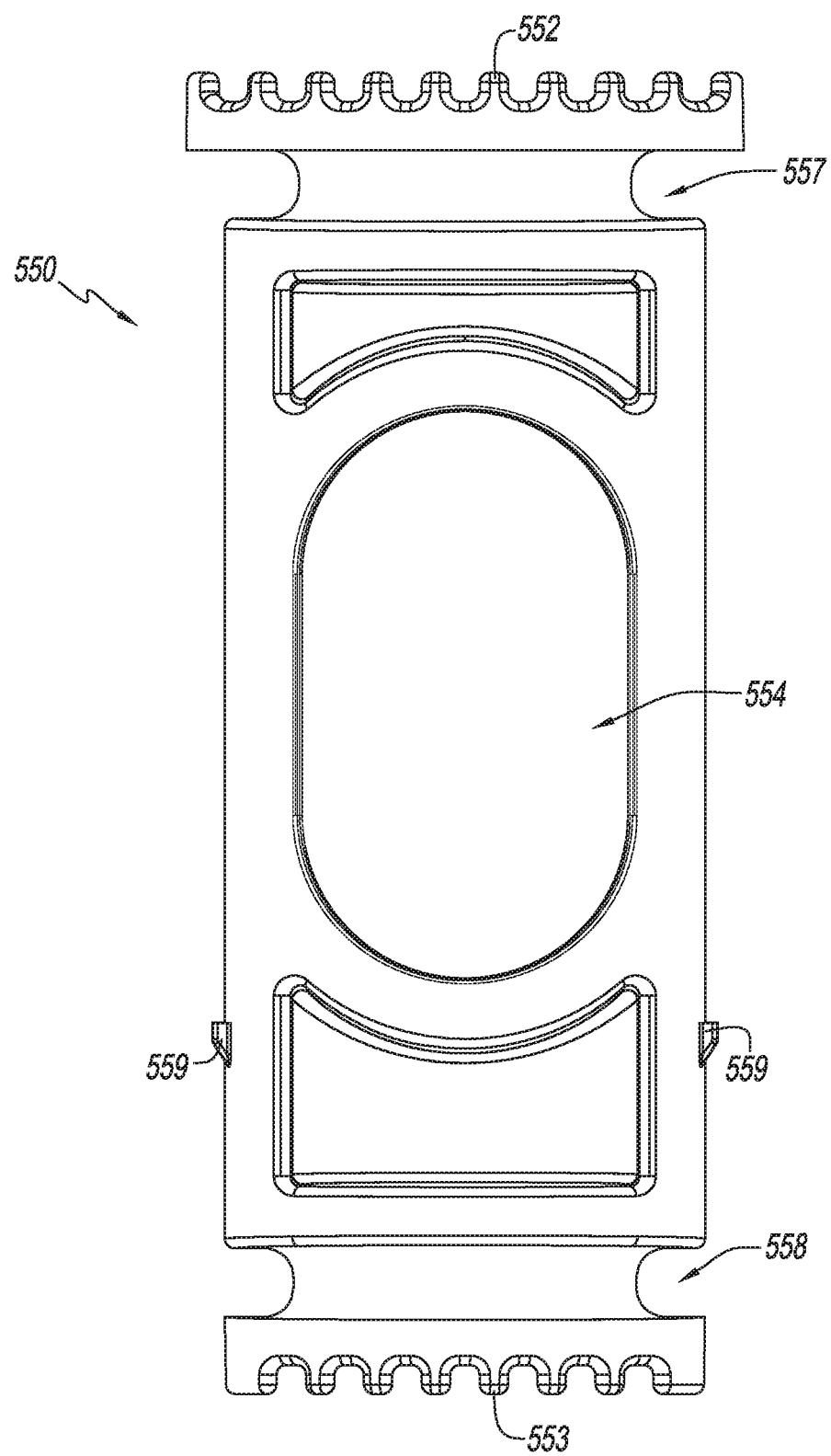
FIG. 33 shows a side view of the slide switch shown in FIG. 32.
Figure 34:
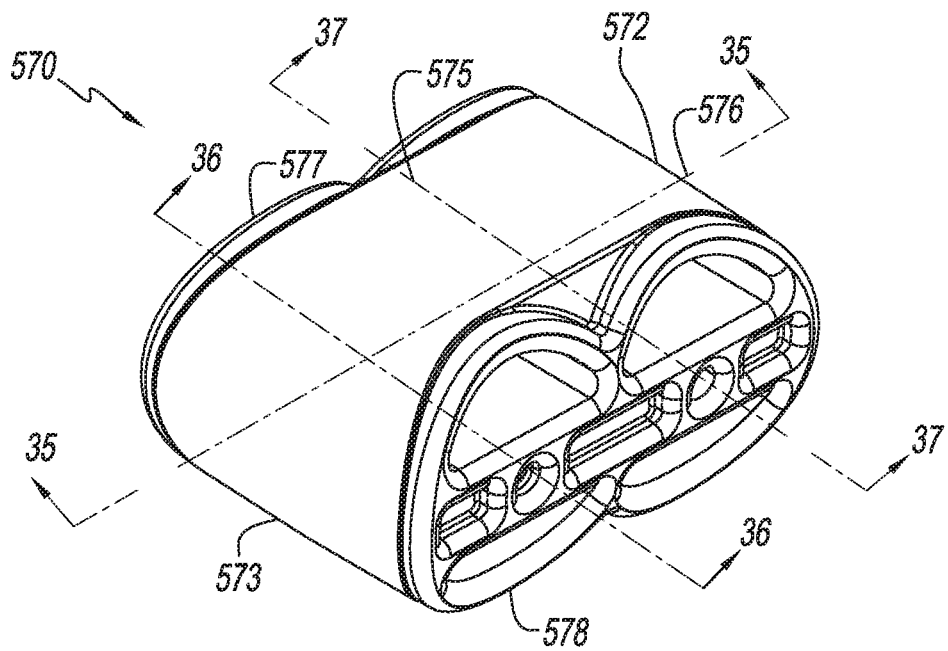
FIG. 34 shows a perspective view of a valve seat used in the valve of FIGS. 21-28.
Figure 35:
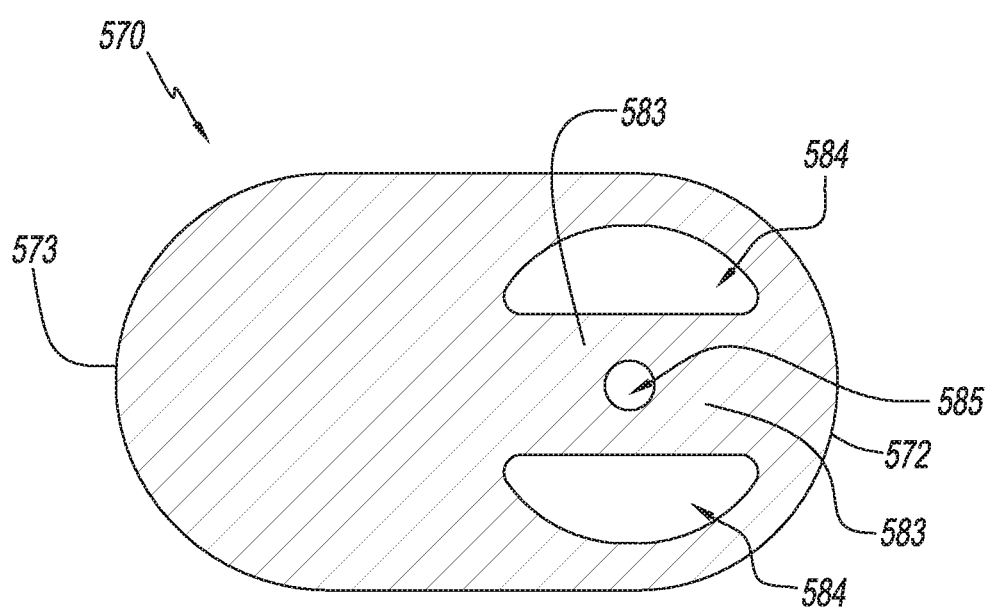
FIG. 35 shows a cross-sectional view of the valve seat shown in FIG. 34, taken along line 35.
Figure 36:
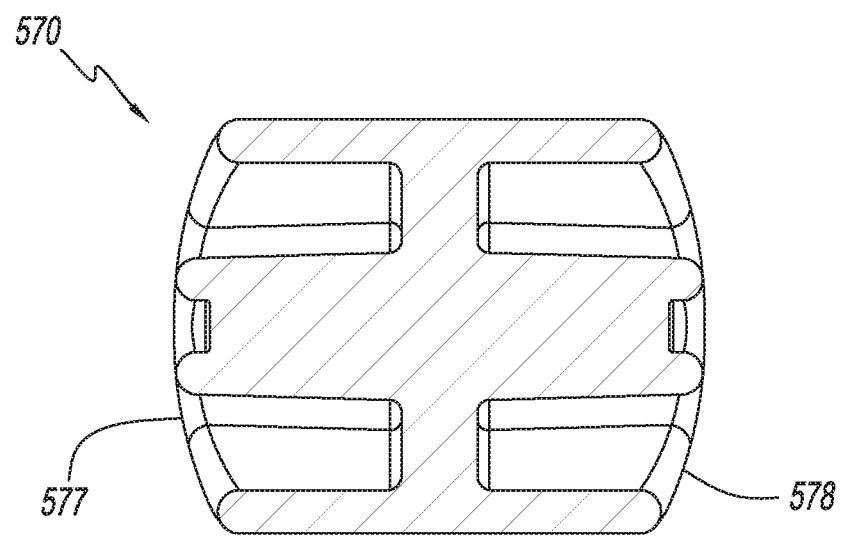
FIG. 36 shows a cross-sectional view of the valve seat shown in FIG. 34, taken along line 36.
Figure 37:
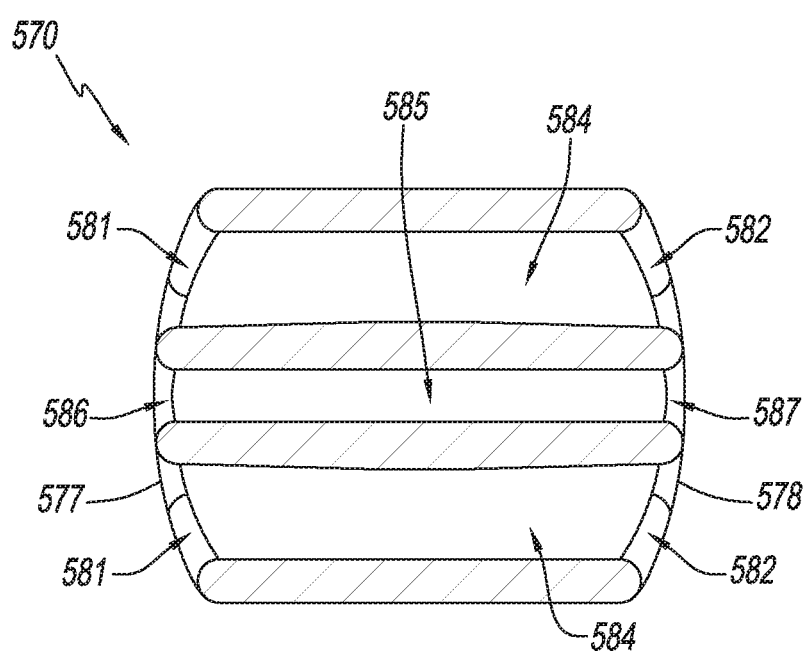
FIG. 37 shows a cross-sectional view of the valve seat shown in FIG. 34, taken along line 37.

The valve 500 may include a slide switch 550, shown in FIGS. 32-33. The slide switch 550 may have a longitudinal axis 556 and a transverse axis 555 substantially perpendicular to the longitudinal axis 556. The slide switch 550 may be elongated along the longitudinal axis 556, having a first end 552 and a second end 553. A channel 554 may extend through the slide switch 550 along the transverse axis 555. A first annular groove 557 may be included on the slide switch 550 proximate the first end 552, and a second annular groove 558 may be included on the slide switch 550 proximate the second end 553. One or more pins 559 may be included proximate the second end 553 of the slide switch 550.

The valve 500 may also include a valve seat 570, shown in FIGS. 34-37. The valve seat 570 may have a longitudinal axis 576 and a transverse axis 575 substantially perpendicular to the longitudinal axis 576. The valve seat 570 may be elongated along the longitudinal axis 576, having a first longitudinal end 572 and a second longitudinal end 573. The valve seat 570 may also be elongated along the transverse axis 575, having a first transverse end 577 and a second transverse end 578. The valve seat 570 may be made of any number of materials, including silicone, thermoplastic elastomers, natural rubber, or any other elastomeric, compressible, non-porous material. In a preferred embodiment, the valve seat 570 may be made of silicone. Additionally, although the valve seat 570 and the slide switch 550 are described as separate components, they may also be manufactured as a single part (for example, by overmolding the valve seat 570 onto the slide switch 550).

A sensor channel 585 may extend through the valve seat 570 from the first transverse end 577 to the second transverse end 578. Preferably, the sensor channel 585 may extend through the valve seat 570 in a direction substantially parallel to the transverse axis 575. The sensor channel 585 may have a first opening 586 on the first transverse end 577 of the valve seat 570 and a second opening 587 on the second transverse end 578 of the valve seat 570. A preferred embodiment of a valve seat 570 is shown in FIGS. 34-37, and includes one sensor channel 585; however, one or more sensor channels 585 may be included.

One or more fluid channels 584 may extend through the valve seat 570 from the first transverse end 577 to the second transverse end 578. Preferably, the one or more fluid channels 584 may extend through the valve seat 570 in a direction substantially parallel to the transverse axis 575. The fluid channel 584 may have a first opening 581 on the first transverse end 577 of the valve seat 570 and a second opening 582 on the second transverse end 578 of the valve seat 570. A preferred embodiment of a valve seat 570, shown in FIGS. 34-37, includes two fluid channels 584; however, one or more fluid channels 584 may be included.

Figure 21:
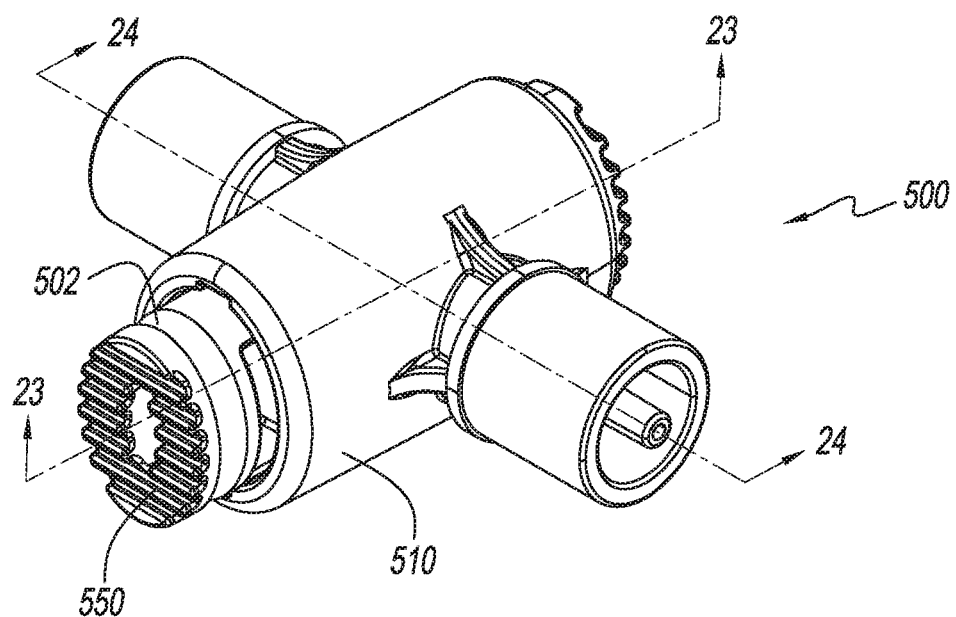
FIG. 21 shows a perspective view of a valve (in an open position) used in the configurations of the negative pressure wound therapy system shown in FIGS. 1B-1C.
Figure 22:
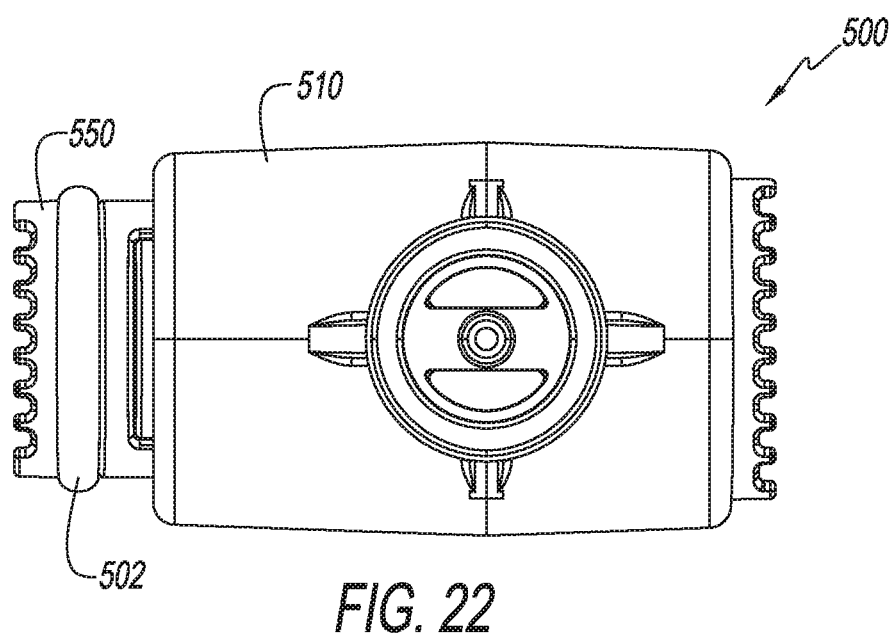
FIG. 22 shows a side view of the valve (in an open position) shown in FIG. 21.
Figure 23:
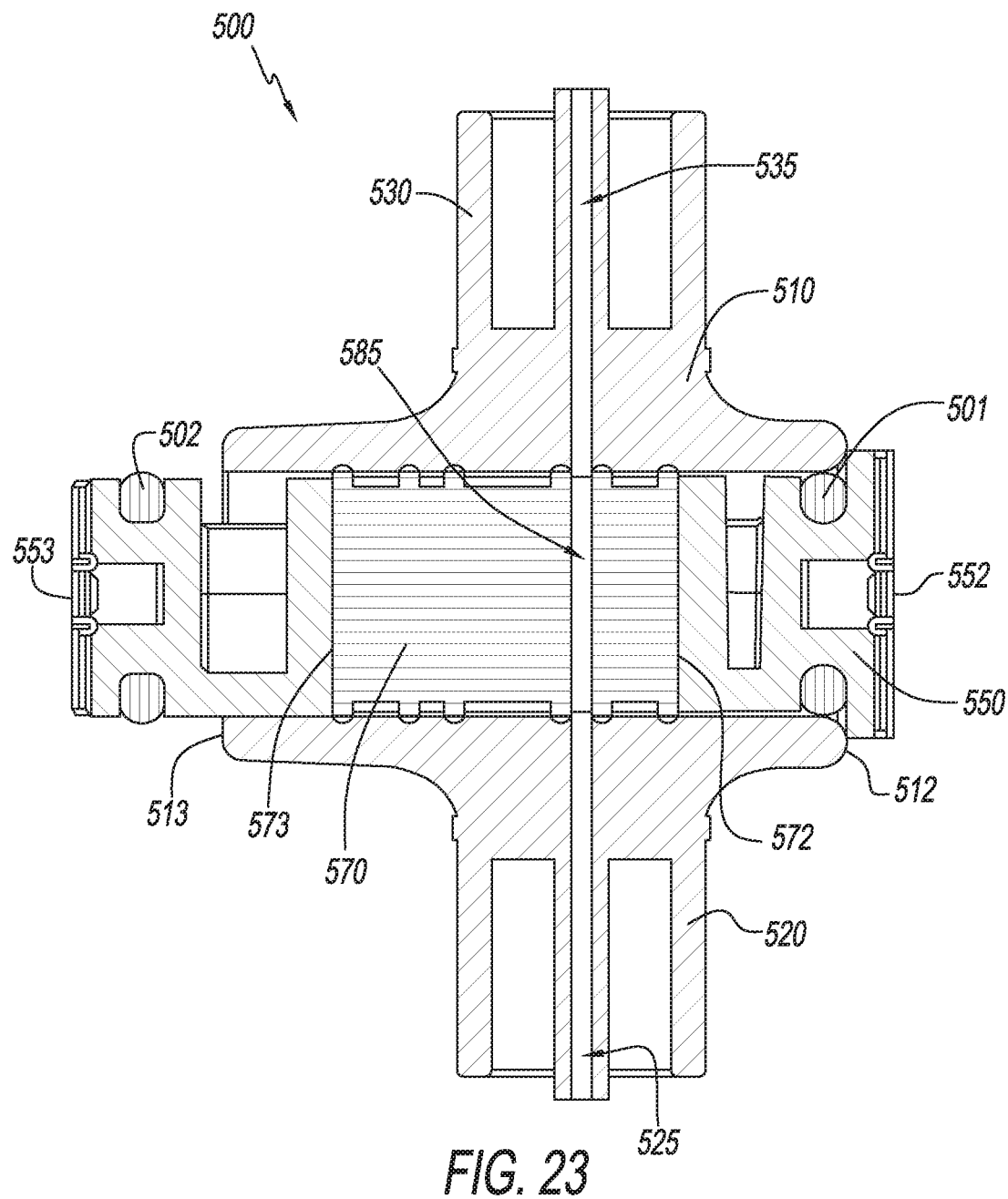
FIG. 23 shows a cross-sectional view of the valve (in an open position) shown in FIG. 21, taken along line 23.
Figure 24:
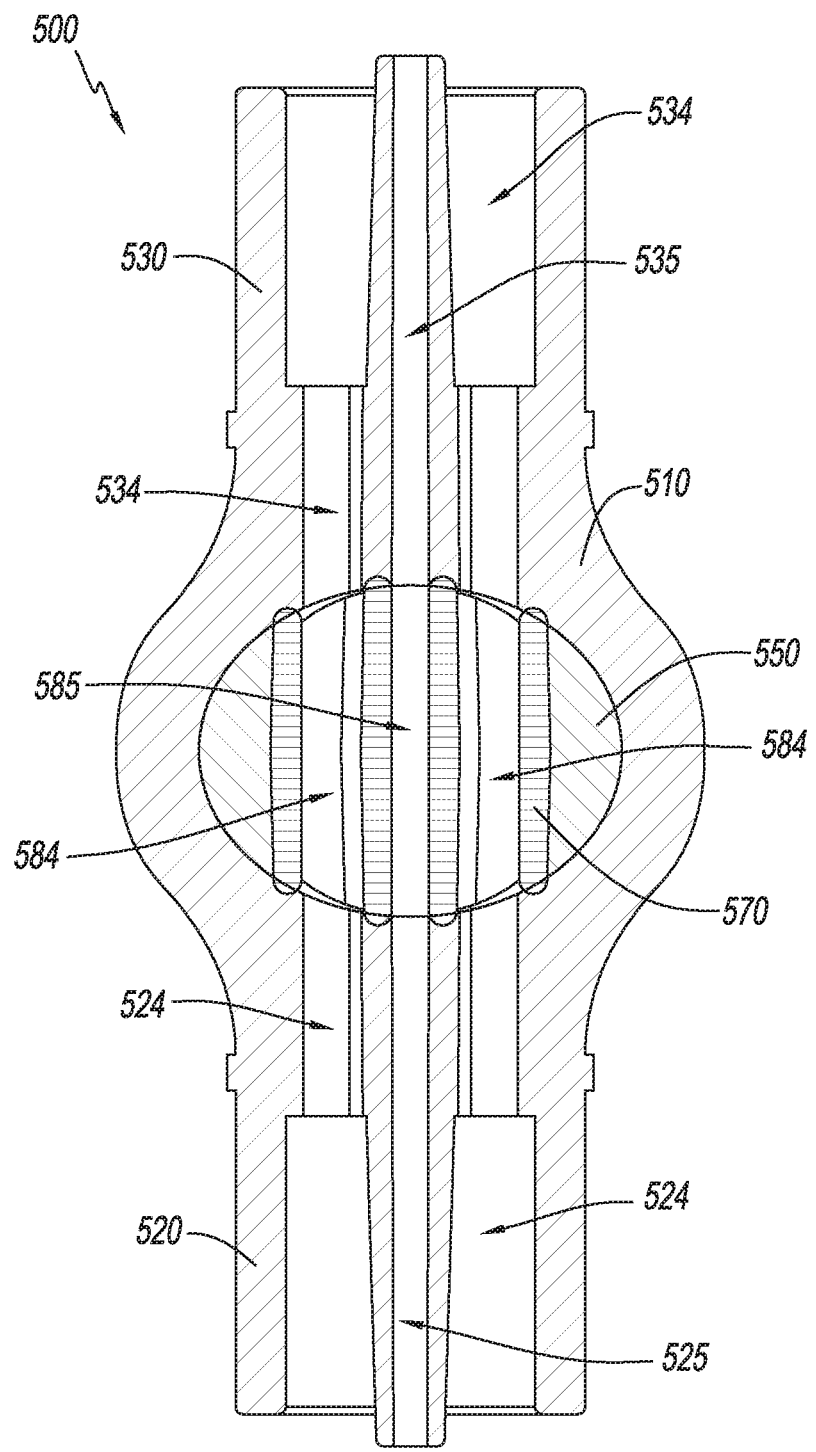
FIG. 24 shows a cross-sectional view of the valve (in an open position) shown in FIG. 21, taken along line 24.
Figure 25:
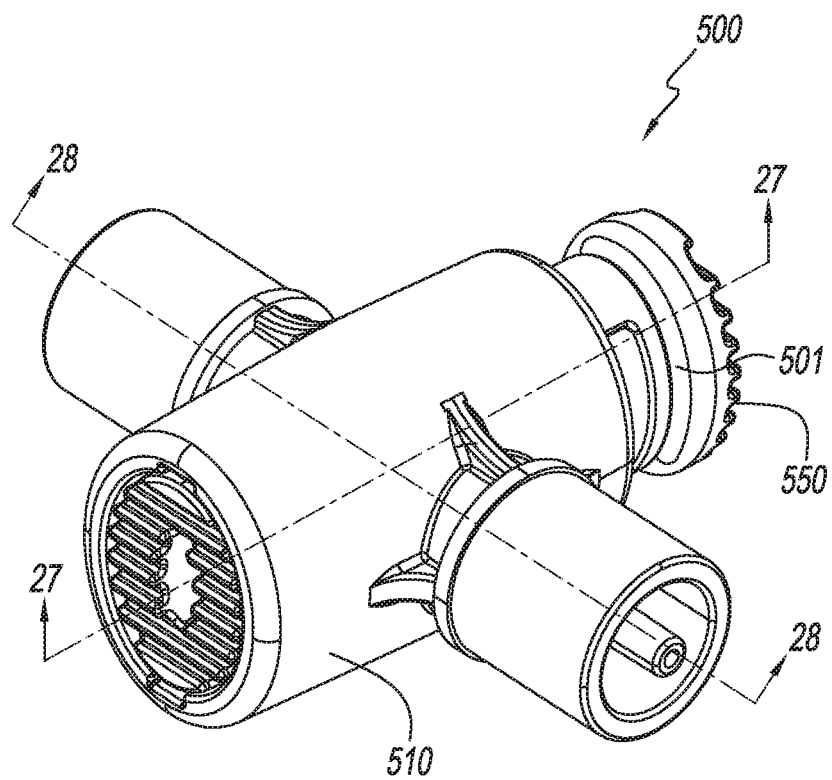
FIG. 25 shows a perspective view of the valve of FIGS. 21-24, now shown in a closed position.
Figure 26:
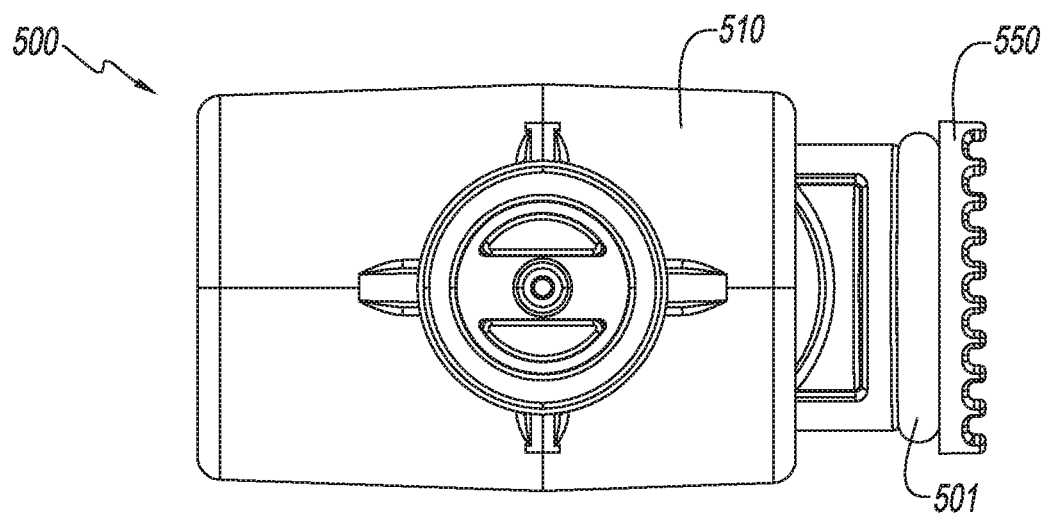
FIG. 26 shows a side view of the valve (in a closed position) shown in FIG. 25.
Figure 27:
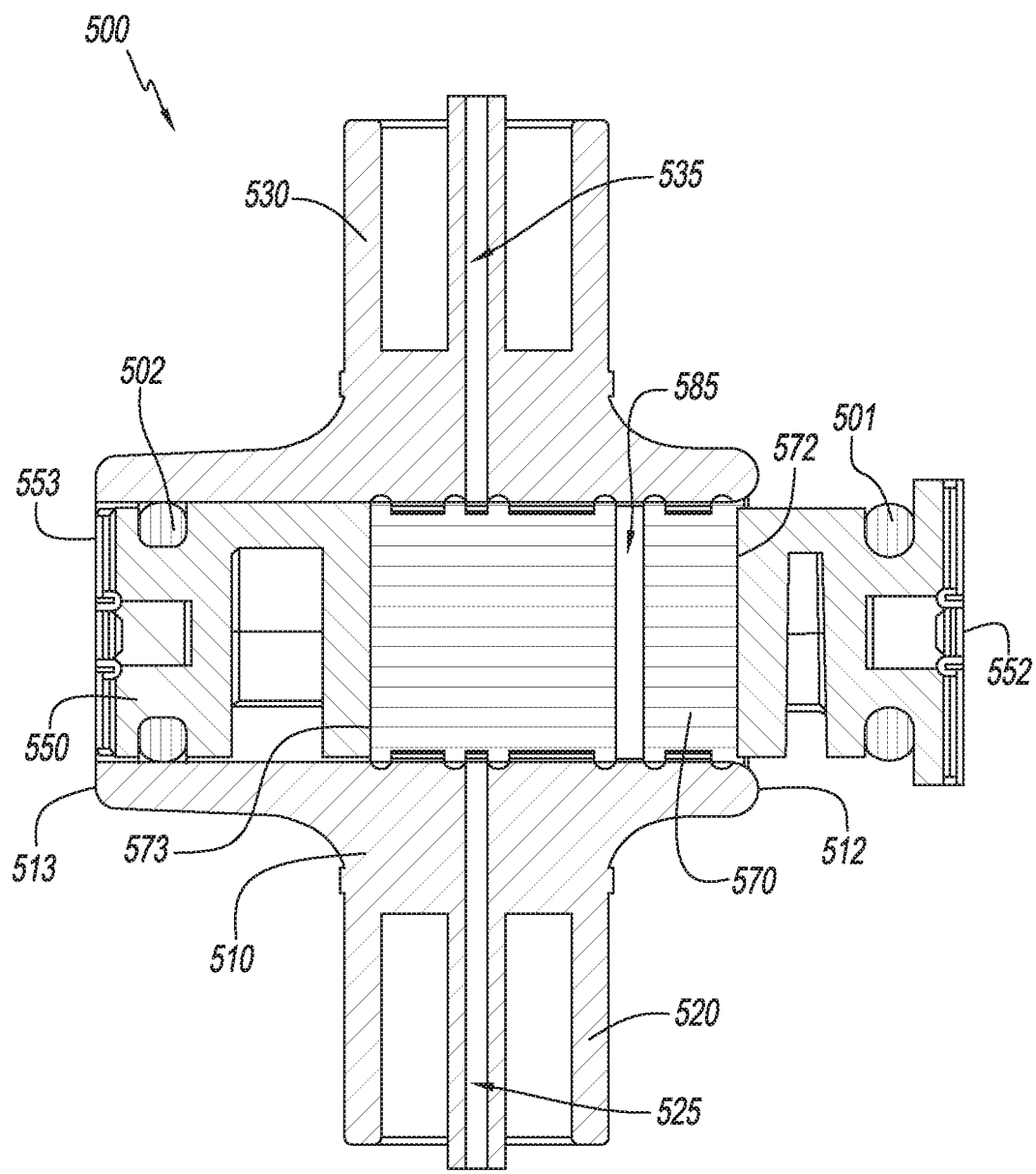
FIG. 27 shows a cross-sectional view of the valve (in a closed position) shown in FIG. 25, taken along line 27.
Figure 28:
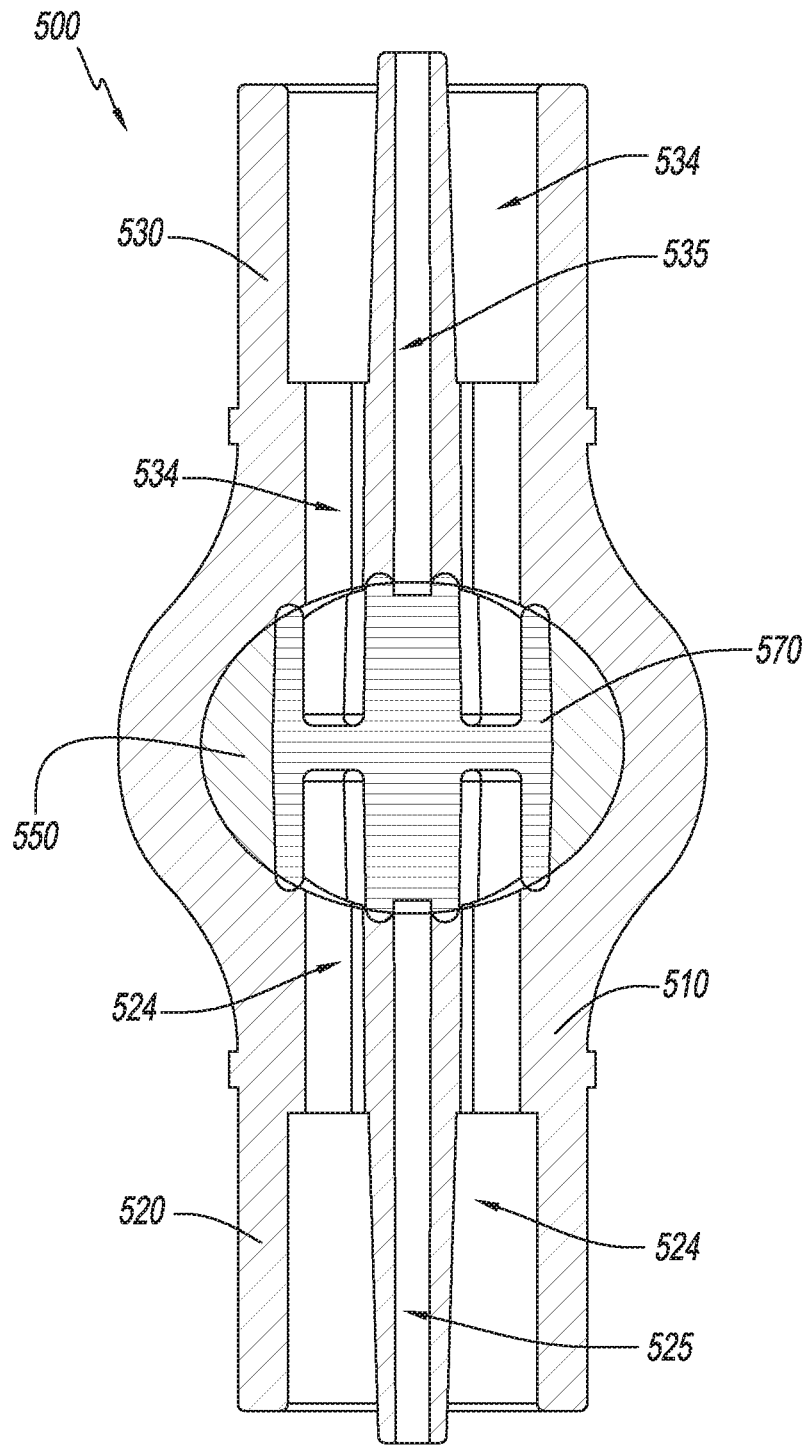
FIG. 28 shows a cross-sectional view of the valve (in a closed position) shown in FIG. 25, taken along line 28.
Figure 29:
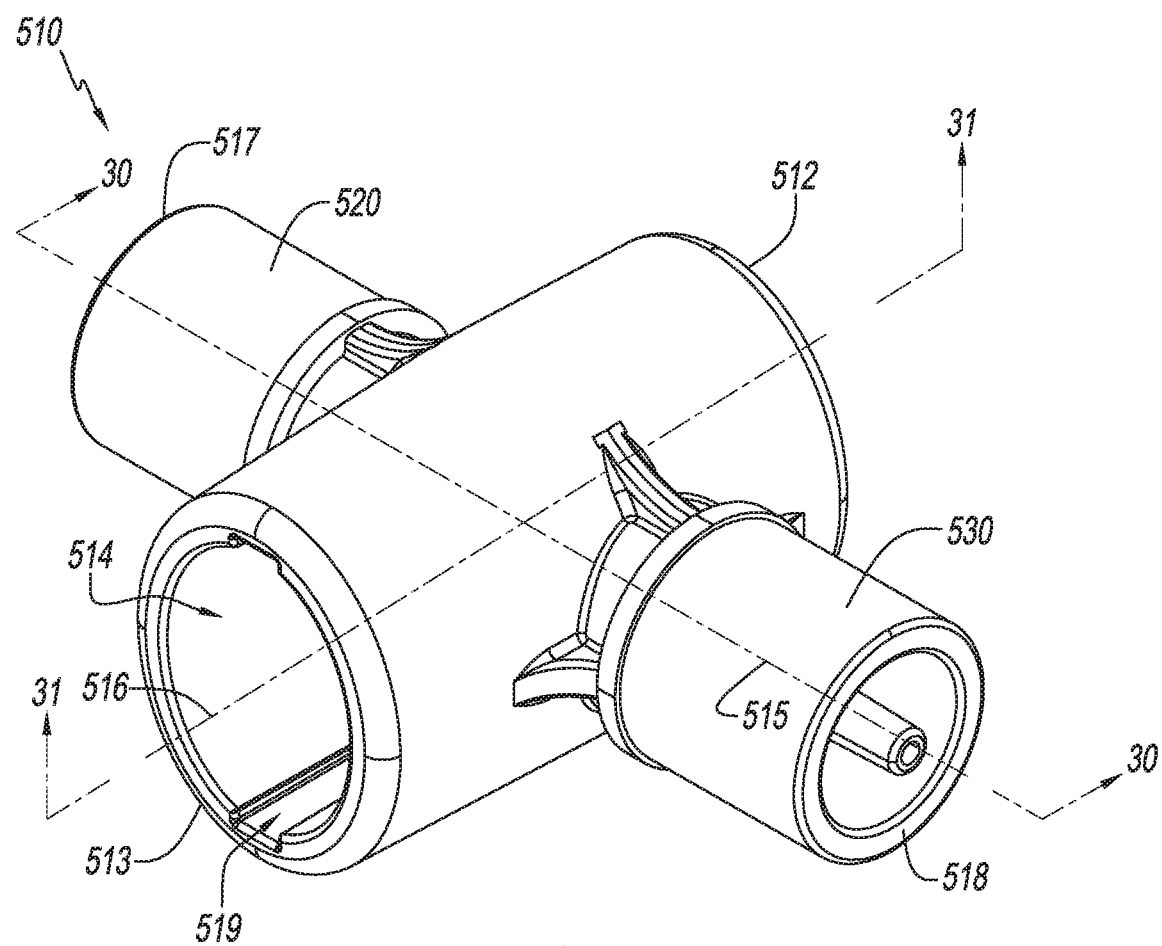
FIG. 29 shows a perspective view of a housing used in the valve of FIGS. 21-28.
Figure 30:
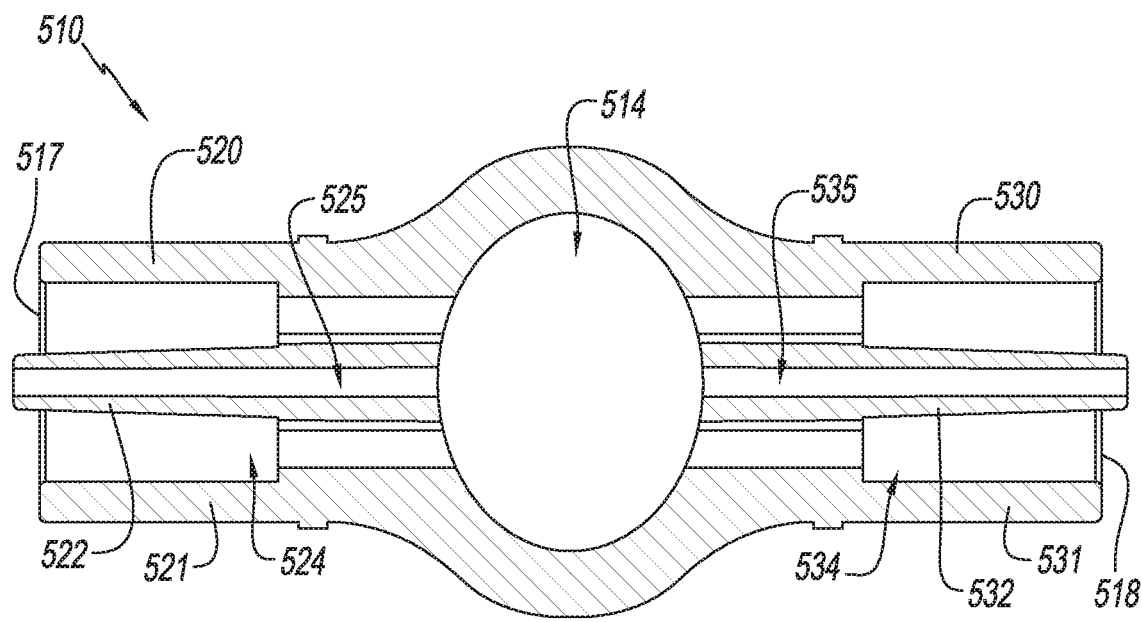
FIG. 30 shows a cross-sectional view of the housing shown in FIG. 29, taken along line 30.
Figure 31:
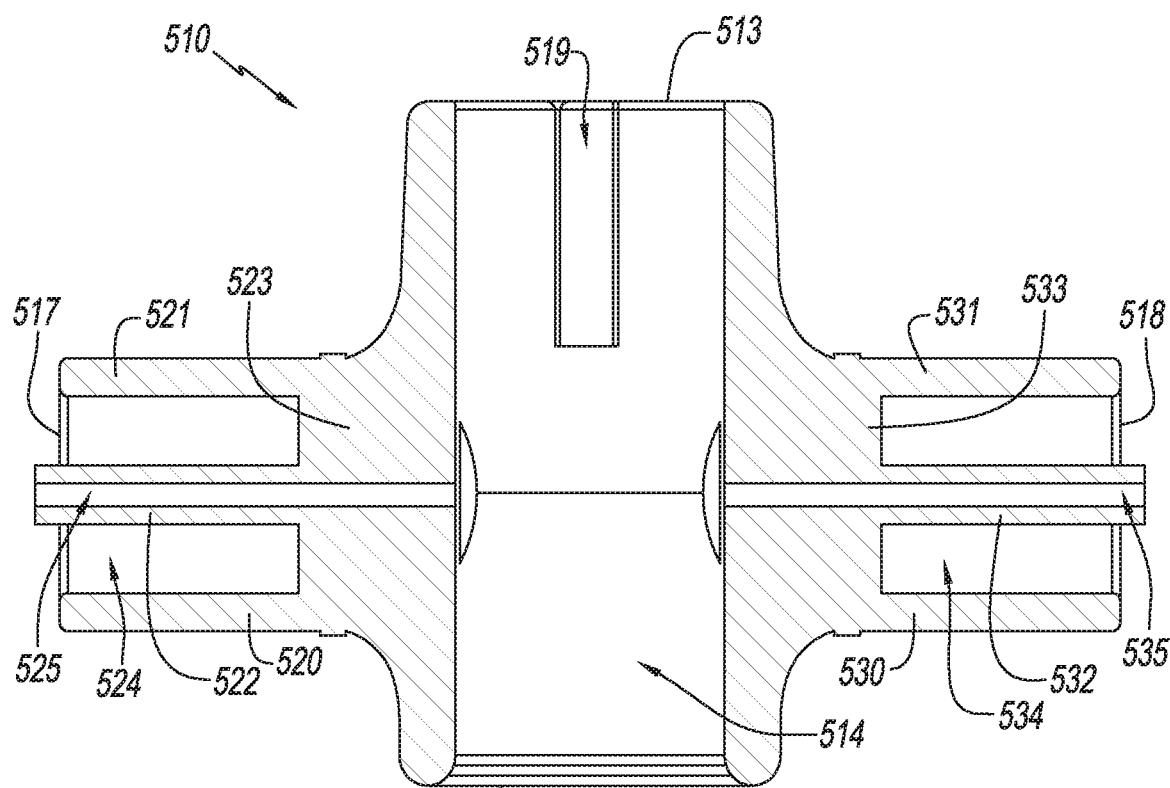
FIG. 31 shows a cross-sectional view of the housing shown in FIG. 29, taken along line 31.

Two indicator bands 501, 502 may be included in the valve 500. These indicator bands 501, 502 provide a visual indication of when the valve 500 is open, and when the valve 500 is closed. As shown in FIGS. 21-23 and 25-27, the indicator bands 501, 502 may be separate components (for example, o-rings) inserted into the annular grooves 557, 558 on the slide switch 550. However, the indicator bands do not need to be separate components from the slide switch 550. For example, the indicator bands 501, 502 could be strips that are painted on appropriate sections of the slide switch 550. As shown in FIGS. 21-23, when the valve 500 is in the open position, the second indicator band 502 may be visible to the user. Optionally, the second indicator band 502 may be green in color to indicate that the valve 500 is open. As shown in FIGS. 25-27, when the valve 500 is in the closed position, the first indicator band 501 may be visible to the user. Optionally, the first indicator band 501 may be red in color to indicate that the valve 500 is closed.

To assemble the valve 500, the valve seat 570 may be inserted into the channel 554 of the slide switch 550. The transverse axis 575 of the valve seat 570 may be substantially parallel with the transverse axis 555 of the slide switch 550. A first indicator band 501 may be positioned in the first annular groove 557, and a second indicator band 502 may be positioned in the second annular groove 558. The slide switch 550 may then be inserted into channel 514 of the valve housing 510. The longitudinal axis 516 of the valve housing 510 may be substantially parallel with the longitudinal axis 556 of the slide switch 550 and the longitudinal axis 576 of the valve seat 570. The transverse axis 515 of the valve housing 510 may be substantially parallel with the transverse axis 555 of the slide switch 550 and the transverse axis 575 of the valve seat 570

In operation, the valve 500 may have two positions: an open position and a closed position. The valve 500 may be moved between the open position and the closed position by moving the valve seat 570 longitudinally relative to the valve housing 510. The valve 500 may be moved to the open position by moving the valve seat 570 longitudinally toward the first longitudinal end 512 of the valve housing 510. When the valve 500 is in the open position, the second indicator band 502 may be located outside the channel 514 on the valve housing 510 such that it is visible to the user. The valve 500 may be moved to the closed position by moving the valve seat 570 longitudinally toward the second longitudinal end 513 of the valve housing 510. When the valve 500 is in the closed position, the first indicator band 501 may be located outside the channel 514 on the valve housing 510 such that it is visible to the user.

When the valve 500 is in the open position, as shown in FIGS. 21-24, the sensor channel 585 of the valve seat 570 may be in communication with the sensor channel 525 of the first port 520 and the sensor channel 535 of the second port 530 of the valve housing 510. Therefore, a vacuum applied to the sensor channel 525 of the first port 520 may be transmitted to the sensor channel 535 of the second port 530, and vice versa. Likewise, the fluid channel 584 of the valve seat 570 may be in communication with the fluid channel 524 of the first port 520 and the fluid channel 534 of the second port 530. Therefore, a vacuum applied to the fluid channel 524 of the first port 520 may be transmitted to the fluid channel 534 of the second port 530, and vice versa.

When the valve 500 is in the closed position, as shown in FIGS. 25-28, the sensor channel 585 of the valve seat 570 is not in communication with at least one of the sensor channel 525 of the first port 520 and the sensor channel 535 of the second port 530 of the valve housing 510. Therefore, the valve seat 570 may block a vacuum applied to the sensor channel 525 of the first port 520 from being transmitted to the sensor channel 535 of the second port 530, and vice versa. Likewise, the fluid channel 584 of the valve seat 570 is not in communication with at least one of the fluid channel 524 of the first port 520 and the fluid channel 534 of the second port 530. Therefore, the valve seat 570 may block a vacuum applied to the fluid channel 524 of the first port 520 from being transmitted to the fluid channel 534 of the second port 530, and vice versa.

Preferably, the valve 500 may be designed to allow the fluid channels 524, 534 to communicate with one another, and the sensor channels 525, 535 to communicate with one another, while preventing cross-communication between the fluid channels 524, 534 and the sensor channels 525, 535. In order to prevent cross-communication, the openings 586, 587 of the sensor channel 585 and the openings 581, 582 of the fluid channel 584 may be carefully positioned on the valve seat 570. A line starting at any point on the first opening 586 of the sensor channel 585 and extending substantially parallel to the longitudinal axis 576 should not pass through or over the first opening 581 of a fluid channel 584, and a line starting at any point on the first opening 581 of a fluid channel 584 and extending substantially parallel to the longitudinal axis 576 should not pass through or over the first opening 586 of the sensor channel 585. Similarly, a line starting at any point on the second opening 587 of the sensor channel 585 and extending substantially parallel to the longitudinal axis 576 should not pass through or over the second opening 582 of a fluid channel 584, and a line starting at any point on the second opening 582 of a fluid channel 584 and extending substantially parallel to the longitudinal axis 576 should not pass through or over the second opening 587 of the sensor channel 585. When the valve 500 is moved between the open position and the closed position by moving the valve seat 570 along its longitudinal axis 576 relative to the valve housing 510, the fluid channels 524, 534 and the sensor channels 525, 535 may be prevented from cross-communicating.

The valve 500 may be designed with features that prevent the valve seat 570 and slide switch 550 from being inadvertently removed from the channel 514 of the housing, and also provide tactile feedback to the user. The first end 552 of the slide switch 550 may be larger than the opening of the channel 514 on the first longitudinal end 512 of the housing 510. As the slide switch 550 and valve seat 570 are moved toward the second longitudinal end 513 of the housing 510, the first end 552 of the slide switch 550 hits the first longitudinal end 512 of the housing 510, which prevents the valve seat 570 and slide switch 550 from being removed from the second longitudinal end 513 of the housing 510. Additionally, each pin 559 on the slide switch 550 is inserted into a groove 519 in the channel 514 of the housing 510. As the slide switch 550 and valve seat 570 are moved toward the first longitudinal end 512 of the housing 510, the pin 559 hits the end of the groove 519, which prevents the slide switch 550 and valve seat 570 from being removed from the first longitudinal end 512 of the housing 510.

Assembly

Figure 38:
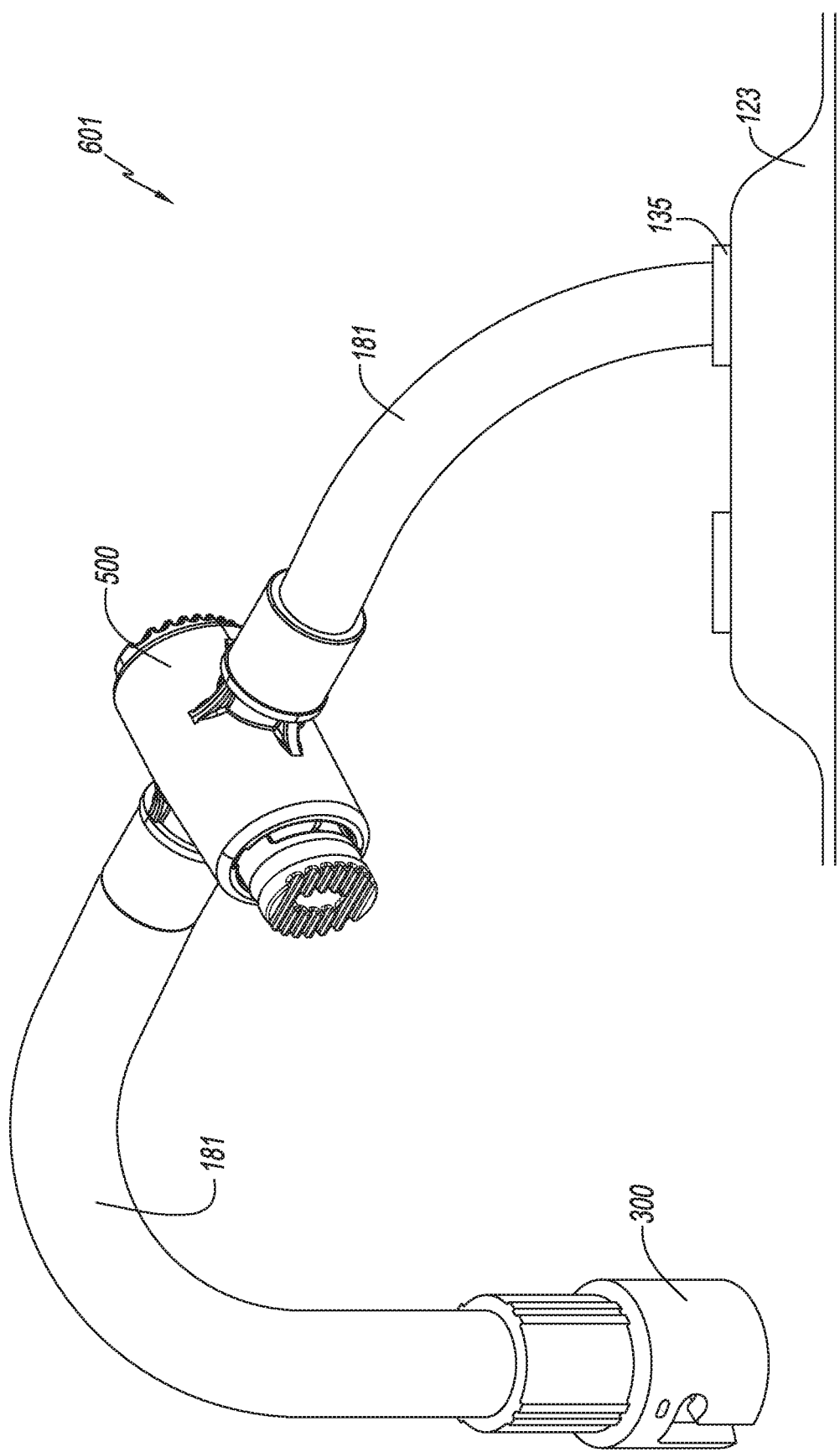
FIG. 38 shows a perspective view of a wound dressing subassembly used in the negative pressure wound therapy system shown in FIGS. 1B-1C.

A wound dressing subassembly 601, shown in FIG. 38, may be provided. The wound dressing subassembly 601 may include a wound dressing 123, a valve 500, an adapter 300, and two patient tube sets 181. One patient tube set 181 may be connected to the fluid port 135 of the wound dressing 123 at one end and the first port 520 of the housing 510 of the valve 500 at the other end. Another patient tube set 181 may be connected to the second port 530 of the housing 510 of the valve 500 at one end and the first port 310 of the adapter 300 at the other end. The valve 500 and one patient tube set 181 may be omitted from the wound dressing subassembly 601 if desired, in which case a single patient tube set 181 may connect the fluid port 135 of the wound dressing 123 to the first port 310 of the adapter 300. The fluid channel 304 in the adapter 300, the fluid channel 189 in the patient tube set 181, and optionally the fluid channels 524, 534, 584 in the valve 500 may form one continuous fluid channel (when the valve 500, if included, is in the open position). The sensor channel 305 in the adapter 300, the sensor channel 188 in the patient tube set 181, and optionally the sensor channels 525, 535, 585 in the valve 500 may form one continuous fluid channel (when the valve 500, if included, is in the open position). If only one wound dressing 123 is being connected to the patient port 167 of the collection container 165, the second port 320 of the adapter 300 of the wound dressing subassembly 601 may be connected to the patient port 167 of the collection container 165.

Figure 39:
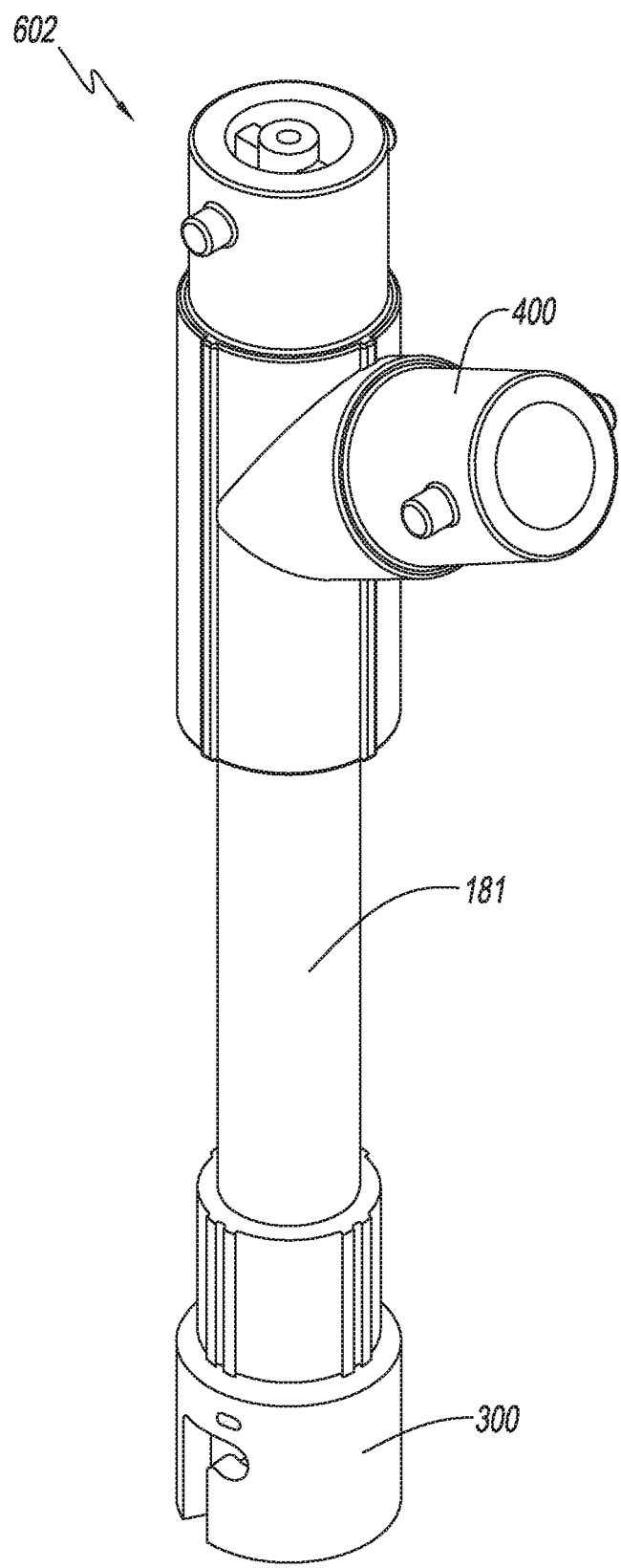
FIG. 39 shows a perspective view of a y-connector subassembly used in the negative pressure wound therapy system shown in FIG. 1C.

Alternatively, if a plurality of wound dressings 123 are being connected to the patient port 167 of the collection container 165, a y-connector subassembly 602, shown in FIG. 39, may be provided. The y-connector subassembly 602 may include a y-connector 400, an adapter 300, and a patient tube set 181. One end of the patient tube set 181 may be connected to the first port 410 of the y-connector 400. Another end of the patient tube set 181 may be connected to the first port 310 of the adapter 300. The fluid channel 304 in the adapter 300, the fluid channel 189 in the patient tube set 181, and the fluid channel 404 in the y-connector 400 may form one continuous fluid channel. The sensor channel 305 in the adapter 300, the sensor channel 188 in the patient tube set 181, and the sensor channel 405 in the y-connector 400 may form one continuous sensor channel. Optionally, a valve 500 could be placed in-line with the patient tube set 181; however, it may be preferred to place the valve 500 on the wound dressing subassembly 601 instead.

The y-connector subassembly 602 may be connected to two wound dressing subassemblies 601 during use. Each of the second and/or third ports 420, 430 of the y-connector 400 may be connected to the second port 320 of the adapter 300 on each wound dressing subassembly 601. The second port 320 of the adapter 300 on the y-connector subassembly 602 may be connected to the patient port 167 on the collection container 165. The sensor channel of the wound dressing subassembly 601 connected to the second port 420 of the y-connector 400 may be in communication with the sensor channel 171 on the patient port 167 of the collection container 165, while the fluid channel may be in communication with the fluid channel 172 on the patient port 167 of the collection container 165. Both the fluid channel and the sensor channel of the wound dressing assembly 601 connected to the third port 430 of the y-connector 400 may be in communication with the fluid channel 172 on the patient port 167 of the collection container 165.

There may be two pneumatic pathways leading away from the wound dressing 123. A first pneumatic pathway pneumatically may associate the wound dressing 123 with one or more of the wound pressure sensor 173, the adjustable restrictor 200, the solenoid 177, and the optional orifice restrictor 178 via a series of tubes (for example, the second tube 182 of the patient tube set 181, sensor tube 190, and tube 176.) In an exemplary embodiment, the wound dressing 123 may be in fluid communication with the sensor channel 171 on the patient port 167 of the collection container 165 via the sensor channel 188 of the patient tube set 181. The sensor channel 171 on the patient port 167 may be in fluid communication with the sensor port 169 via sensor tube 190. The sensor port 169 of collection container 165 may be in fluid communication with one or more of the wound pressure sensor 173, the adjustable restrictor 200, the solenoid 177, and the optional orifice restrictor 178 via tube 176. Although the second tube 182 of the patient tube set 181, sensor tube 190, and tube 176 are described as separate components, one or more of these tubes may be formed as a single tube. In the exemplary embodiments, vacuum is not applied to the cavity of the wound dressing 123 through the sensor channel 188 of the patient tube set 181, so fluid does not flow from the wound dressing 123 into the sensor channel 188.

A second pneumatic pathway allows vacuum to be applied to the wound dressing by pneumatically associating the wound dressing 123 with the internal chamber 166 of the collection container 165 and ultimately with the vacuum pumps 105 and/or 107 and the pump pressure sensor 109. The wound dressing 123 may be in fluid communication with the internal chamber 166 of the collection container 165 via the fluid channel 189 of the patient tube set 181 and the fluid channel 172 of the patient port 167 of collection container 165. The internal chamber 166 of the collection container 165 may be in fluid communication with the vacuum pumps 105 and/or 107 via tube 115 which is connected to the vacuum port 168 of the collection container 165.

The first pneumatic pathway and the second pneumatic pathway may be in fluid communication at the suction port 135 of the wound dressing 123. Therefore, a suction force may be applied to the sensor channel 188 at the suction port 135 of the wound dressing 123 which helps to draw any fluid in the sensor channel 188 back toward the wound dressing 123, and eventually through the fluid channel 189. As such, the vacuum is applied to the cavity of the wound dressing 123 through the fluid channel 189 of the patient tube set 181, causing fluid in the wound dressing 123 to preferentially flow into the fluid channel 189 instead of flowing into the sensor channel 188. The air leak, optionally created by the adjustable restrictor 200, provides a force that is additive to the vacuum. While fluid is being drawn away from the wound dressing 123 by the vacuum in the fluid channel 189 of the patient tube set 181, the air leak in the sensor channel 188 prevents fluid from entering the sensor channel 188, pushes any fluid that may enter the sensor channel 188 back towards the wound dressing 123, and pushes fluid in the wound dressing 123 into fluid channel 189. The additive forces generated by the air leak and the vacuum help to keep the sensor channel 188 clear of fluid, which ensures that the pressure measured by the wound pressure sensor 173 accurately reflects the therapeutic pressure applied at the wound dressing 123. The additive forces also advantageously prevent standing fluid and occlusions from occurring in the fluid channel 189, which may affect the therapeutic pressure provided at the wound dressing 123.

Operation

When a user is ready to use the system 100, a wound dressing 123 may be applied to the wound site. The wound dressing 123 may be connected to the collection container 165 via patient tube set 181. The internal chamber 166 of the collection container 165 may be pneumatically associated with vacuum pumps 105 and/or 107 via tube 115. A vacuum pressure may be created by vacuum pumps 105 and/or 107. This vacuum pressure may be applied to the internal chamber 166 of the collection container 165 via tube 115. The fluid channel 189 of patient tube set 181 may pneumatically associate the internal chamber 166 of the collection container 165 with the suction port 135 of the wound dressing 123. Thus, the fluid channel 189 of patient tube set 181 may be pneumatically associated with vacuum pumps 105 and/or 107, thereby allowing vacuum pressure created by vacuum pumps 105 and/or 107 to be applied in the cavity of the wound dressing 123.

During use, it may be desirable to monitor the pressure being applied at various points in the system 100. The pump pressure sensor 109 may measure the vacuum pressure created by vacuum pumps 105 and/or 107. However, the pressure measured by the pump pressure sensor 109 may not be equal to the therapeutic pressure applied to the cavity of the wound dressing 123 for several reasons. Standing fluid in the fluid channel 189 of the patient tube set 181 may create hydrostatic forces that increase or decrease the therapeutic pressure of the vacuum being applied to the cavity of the wound dressing 123, depending on the position of the wound relative to vacuum pumps 105 and/or 107. The patient tube set 181 may become kinked, crushed, or otherwise deformed, which may decrease the therapeutic pressure. The patient tube set 181 may become completely blocked with viscous fluids and/or wound exudate, which may decrease the therapeutic pressure. Therefore, the pump pressure sensor 109 may not necessarily be an accurate indication of the therapeutic pressure applied to the wound dressing 123. A pressure sensor pneumatically associated with the internal chamber 166 of the collection container 165 may have the same disadvantage, because the pressure in the internal chamber 166 of the collection container 165 may not be equal to the therapeutic pressure applied to the cavity of the wound dressing 123.

However, the system 100 may measure the therapeutic pressure applied at the wound dressing 123 using a wound pressure sensor 173 pneumatically associated with the cavity of the wound dressing 123 through at least one of tube 176, sensor tube 190, and the sensor channel 188 of the patient tube set 181. Fluid is not intended to travel inside the sensor channel 188, and therefore pressure differentials between the wound pressure sensor 173 and the cavity of the wound dressing 123 may be avoided because there is no standing fluid (or minimal amounts of standing fluid) in sensor channel 188 to create hydrostatic forces.

One advantage of the system 100 is that it enables the microcontroller 101 to detect standing fluid and occlusions in the patient tube set 181. The microcontroller 101 may compare the pressures measured by the wound pressure sensor 173 and the pump pressure sensor 109. If there is a discrepancy between the two measurements, control algorithm 150 may contain instructions that alert the user and/or cause the system 100 make adjustments to ensure that the intended therapeutic pressure is being applied at the wound dressing 123.

If the absolute pressure measured by the wound pressure sensor 173 is greater than the absolute pressure measured by the pump pressure sensor 109, the control algorithm 150 may contain instructions that instruct pumps 105 and/or 107 to run, or continue to run, in order to compensate for the increase in the absolute value of the therapeutic pressure at the wound.

If the absolute pressure measured by the wound pressure sensor 173 is less than the absolute pressure measured by the pump pressure sensor 109, control algorithm 150 may contain instructions that will instruct pumps 105 and/or 107 to turn off, or run less frequently, in order to compensate for the decrease in the absolute value of the therapeutic pressure at the wound. Control algorithm 150 may also contain instructions to open the solenoid 177 to relieve pressure in order to compensate for the decrease in the absolute value of the therapeutic pressure at the wound, if necessary.

The system 100 may use the above steps to try to resolve differences between the pressure measured by the wound pressure sensor 173 and the pressure measured by the pump pressure sensor 109. However, if these steps are unable to resolve the difference, the control algorithm 150 may contain instructions to active a blockage alarm (optionally, via the display 160). The user would then know to inspect the patient tube set 181 for kinking, crushing, standing fluid, or other blockages.

In addition to being able to detect occlusions and standing fluid and take reactive measures to correct the therapeutic pressure at the wound dressing 123, the system 100 also prevents kinking and crushing of the patient tube set 181, and prevents blockages and standing fluid from occurring in the patient tube set 181 in the first place. As discussed above, the tube-within-a-tube design for the patient tube set 181 may reduce the likelihood that crushing or bending the patient tube set 181 will cause the tube to kink and become occluded. Furthermore, the air leak, optionally created by the adjustable restrictor 200 and/or solenoid 177, may provide a force that is additive to the vacuum pressures, helping to move fluid along the fluid channel 189 of the patient tube set 181. Standing fluid and occlusions in the patient tube set 181 are not only unsightly, but they may cause the user to think that the system is not working.

Generally speaking, the patient port 167 of the collection container 165, the second port 320 of the adapter 300, and the second and third ports 420, 430 of the y-connector 400 may each have either a male fitting or a female fitting. Preferably, the patient port 167 of the collection container 165 and the second and third ports 420, 430 of the y-connector 400 may have a male fitting, and the second port 320 of the adapter 300 may have a female fitting. Alternatively, the patient port 167 of the collection container 165 and the second and third ports 420, 430 of the y-connector 400 may have a female fitting, and the second port 320 of the adapter 300 may have a male fitting.

EXAMPLES

Figure 42:
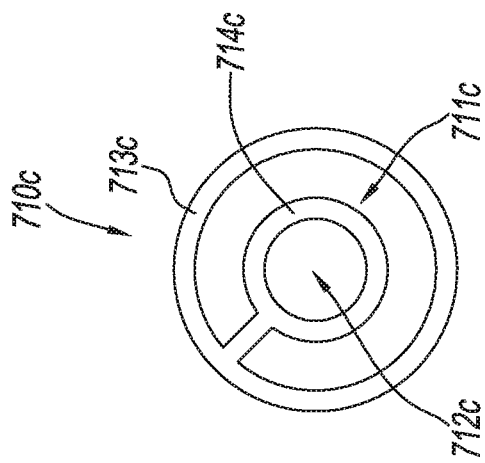
FIG. 42 shows a side view of an Example 1 tube set.

Samples: Three types of tube sets (Example 1, Comparison A, and Comparison B) were tested to determine the crushing force required to occlude the fluid channel of each tube set. As shown in FIG. 42, Example 1 tube sets 710c were dual-lumen tube sets having a tube-within-a-tube design according to certain embodiments described in the present disclosure. The tube sets of Example 1 had a first tube 713c and a second tube 714c, and the second tube was positioned in the lumen of the first tube. The lumen of the second tube formed the sensor channel 712c, and the space between the inner surface of the first tube and the outer surface of the second tube formed the fluid channel 711c.

Figure 41:
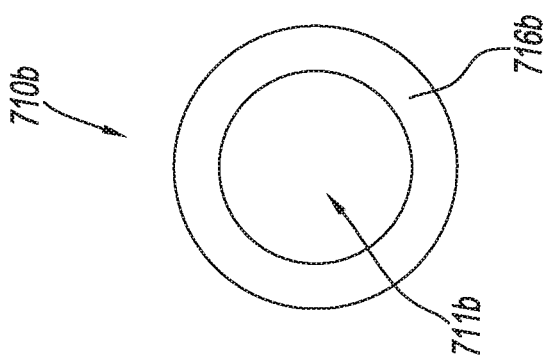
FIG. 41 shows a side view of a Comparison B tube set.
Figure 40:
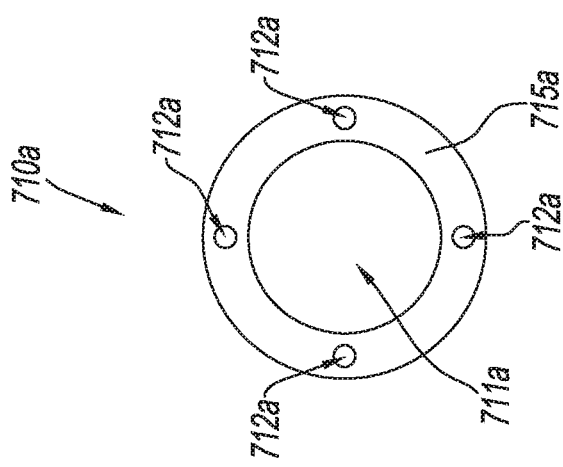
FIG. 40 shows a side view of a Comparison A tube set.

Unlike Example 1, neither Comparison A tube sets nor Comparison B tube sets included a first tube and a second tube, where the second tube was positioned in the lumen of the first tube. As shown in FIG. 40, Comparison A tube sets 710a were multi-lumen tube sets manufactured by KCI®. Comparison A tube sets had one fluid channel 711a and four sensor channels 712a parallel to, but located entirely outside of, the fluid channel. Comparison A tube sets included one tube 715a—the fluid channel was the lumen of the tube, and the sensor channels extended inside the tube wall, along the length of the tube. As shown in FIG. 41, Comparison B tube sets 710b were single-lumen tube sets manufactured by Cardinal Health®. Comparison B tube sets had a single tube 716b, and the lumen of the tube formed a fluid channel 711b. Comparison B tube sets did not include a sensor channel.

Test Set-up: In order to determine the crushing force required to occlude the fluid channel of each sample tube set, test equipment was configured to a) apply and measure a crushing force to the sample tube set, and b) objectively determine whether the fluid channel was occluded at any given point in time. The test configurations described below and shown in FIGS. 43-46 were used in these Examples; however, various test configurations with additional, fewer, or different components may be used to achieve the same results.

Figure 44:
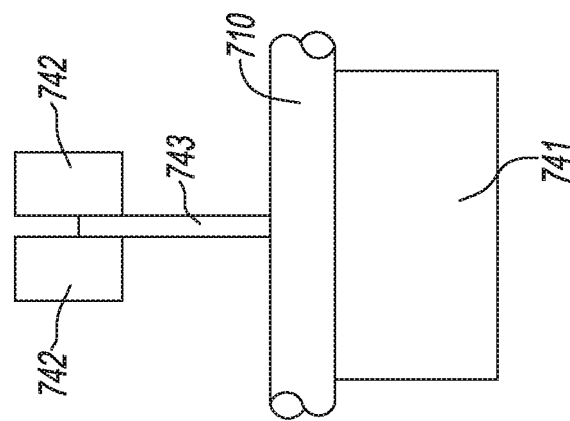
FIG. 44 shows a front view of the test set-up of FIG. 43.
Figure 43:
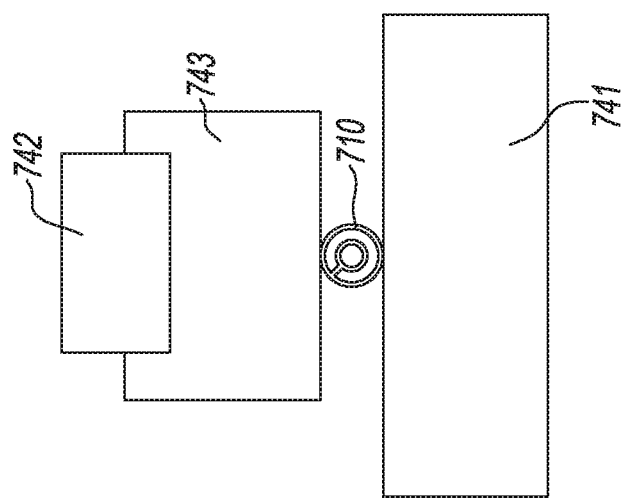
FIG. 43 shows a side view of test set-up including a mechanical test system and a sample tube set.

A mechanical testing machine 740 was used to apply and measure a crushing force to the sample tube set 710 as shown in FIGS. 43-44. The mechanical testing machine used in these experiments was a Zwick Z005 testing machine, but any device capable of applying and measuring compression forces could be used instead. FIGS. 43-44 refer to a sample tube set 710 which could represent any one of Comparison A tube set 710a, Comparison B tube set 710b, or Example 1 tube set 710c depending on the sample being tested.

As shown in FIGS. 43-44, the mechanical testing machine 740 had a sample platform 741 and two jaws 742 that were moveably connected to the sample platform 741 by a support structure (not shown in FIGS. 43-44). A driving feature (also not shown in FIGS. 43-44) causes the jaws 742 to travel in a direction perpendicular to the sample platform 741. A thin plate 743 having a thickness of 1.27 mm was clamped between the jaws 742. The thin plate 743 was substantially perpendicular to the sample platform 741 of the mechanical testing machine. The sample tube set 710 was positioned on the sample platform 741 such that the thin plate 743 was substantially perpendicular to the length of the sample tube set 710, as shown in FIGS. 43-44. A load cell (not shown in FIGS. 43-44) on the mechanical testing machine measured the crushing force generated as the jaws 742 traveled toward the sample platform 741, causing the thin plate 743 to crush the sample tube set 710.

Figure 45:
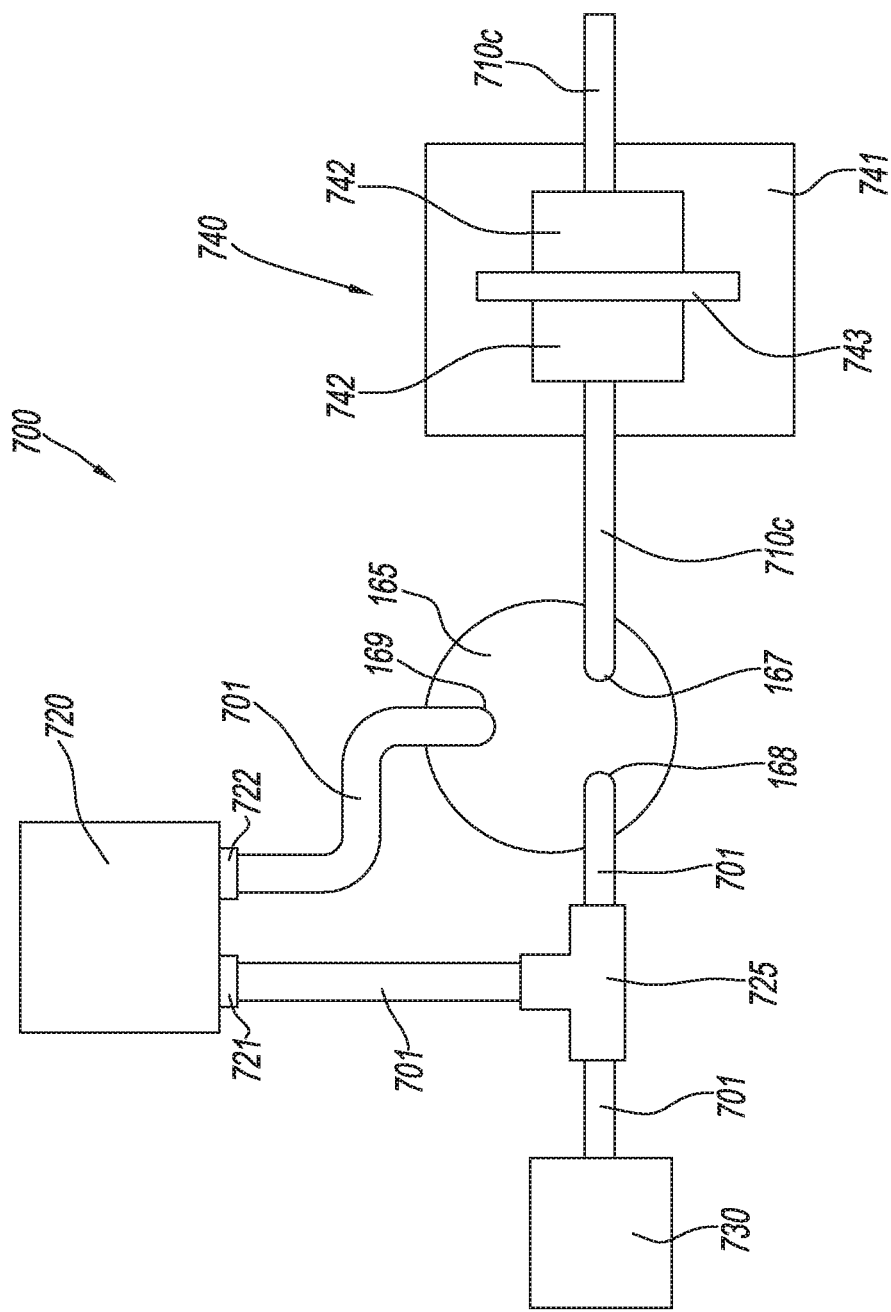
FIGS. 45-46 shows two test configurations used to test the sample tube sets in the EXAMPLE section.
Figure 46:
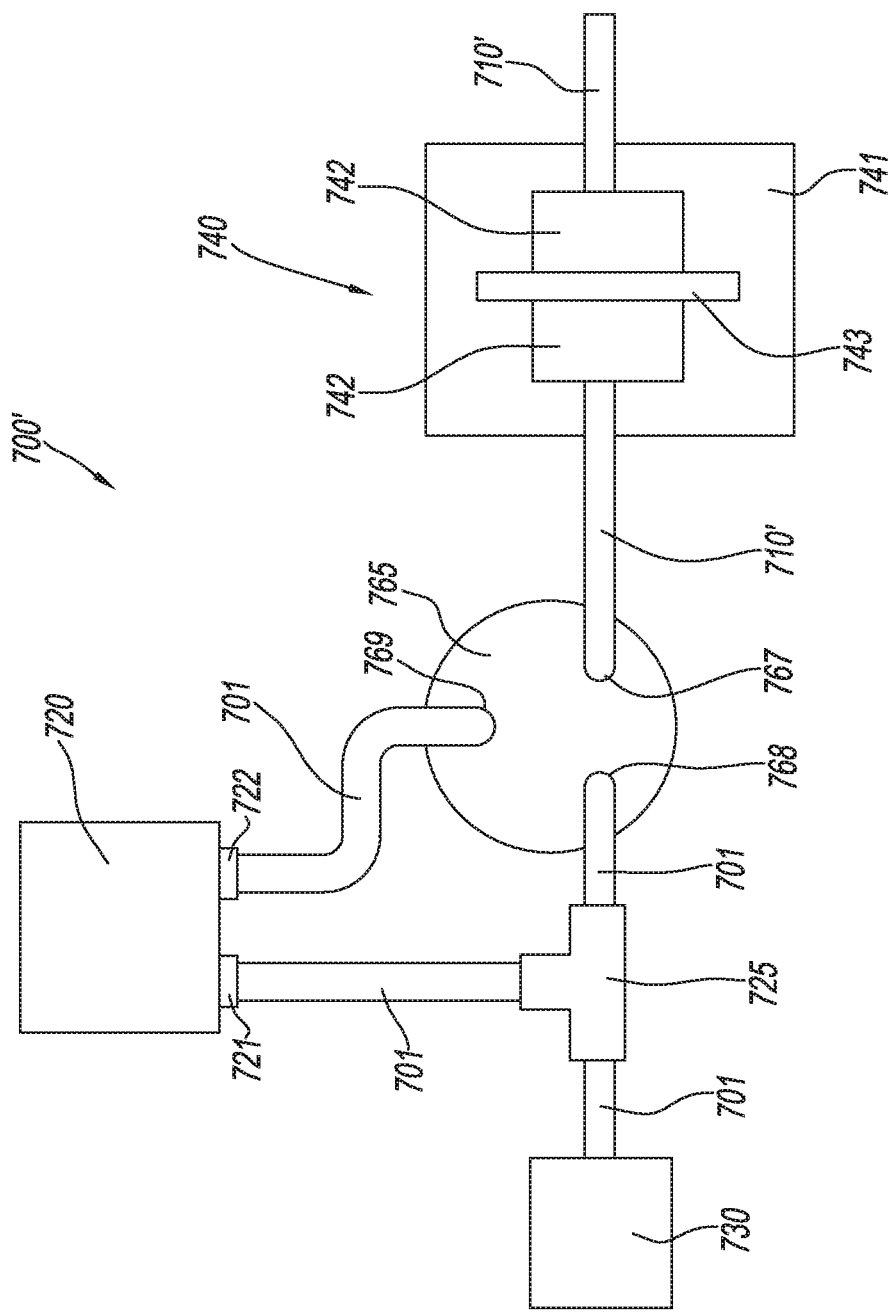

The test configurations 700, 700' shown in FIGS. 45-46 allowed the user to objectively determine whether the fluid channel in the sample tube set was occluded. In each test configuration 700, 700', a pump unit 720 applied a vacuum to the device end of the fluid channel of the sample tube set, and the patient end of the fluid channel was open to atmosphere. A pressure sensor 730 was used to monitor the pressure in the fluid channel. When the fluid channel was not occluded, the pressure along the entire fluid channel was equal to atmospheric pressure. However, when the fluid channel was crushed to the point of occlusion, the absolute pressure in the device end of the fluid channel decreased, signaling to the user that the fluid channel was occluded.

Test configuration 700 (shown in FIG. 45) was used to test Example 1 tube sets, and included a pump unit 720, a pressure sensor 730, a collection container 165, a sample tube set 710c, a T-connector 725, and pneumatic tubing 701. The pump unit 720 was a Cardinal Health™ NPWT PRO pump unit, but the test configuration could be modified to use any vacuum source. The pressure sensor 730 was a digital manometer, but any device capable of measuring vacuum pressures could be used instead. The collection container 165 was discussed above and is shown in FIGS. 3A-3E.

In test configuration 700, the sample tube set 710c was connected to the patient port 167 of the collection container 165, allowing the fluid channel 711c of the sample tube set 710c to communicate with the internal chamber 166 of the collection container 165. The sensor port 169 of the collection container 165 was connected to a sensor port 722 on the pump unit 720. The vacuum port 168 of the collection container 165 was connected to a T-connector 725, and the T-connector 725 was connected to a vacuum port 721 on the pump unit 720 and the pressure sensor 730. Therefore, the pressure sensor 730 was in pneumatic communication with the internal chamber 166 of the collection container 165 and the fluid channel of sample tube set 710c.

Test configuration 700' (shown in FIG. 46) was used to test Comparison A tube sets and Comparison B tube sets (collectively shown in FIG. 46 as 710'). Test configuration 700' included a pump unit 720, a pressure sensor 730, a collection container 765, a sample tube set 710', a T-connector 725, and pneumatic tubing 701. The pump unit 720 and pressure sensor 730 were the same as those used in test configuration 700. The collection container 765 used in test configuration 700' was similar to collection container 165. Collection container 765 also included a patient port 767, a vacuum port 768, and a sensor port 769. The vacuum port 768 and sensor port 769 of collection container 765 were similar to the vacuum port 168 and sensor port 169 of collection container 165. However, there were two differences between collection container 165 and collection container 765: 1) the patient port 167 of collection container 165 was a dual-lumen port having a fluid channel and a sensor channel, whereas the patient port 767 of collection container 765 was a single-lumen port having only a fluid channel, and 2) the collection container 165 included a sensor tube 190 that connected the sensor port 169 to the sensor channel of the patient port 167, whereas collection container 765 did not include a sensor tube, and the sensor port 769 was instead open to the internal chamber of the collection container 765.

In test configuration 700', the fluid channel of the sample tube set 710' was connected to the patient port 767 of the collection container 765, allowing the fluid channel of the sample tube set 710' to communicate with the internal chamber of the collection container 765. The sensor port 769 of the collection container 765 was connected to a sensor port 722 on the pump unit 720. The vacuum port 768 of the collection container 765 was connected to a T-connector 725, and the T-connector 725 was connected to a vacuum port 721 on the pump unit 720 and the pressure sensor 730. Therefore, the pressure sensor 730 was in pneumatic communication with the internal chamber of the collection container 765 and the fluid channel of sample tube set 710'.

Based on the set-up described above, when testing Comparison A tube sets and Example 1 tube sets, the vacuum source and the pressure sensor were pneumatically associated with the fluid channel, and were not pneumatically associated with the sensor channels. When testing Comparison B tube sets, the vacuum source and the pressure sensor were pneumatically associated with the fluid channel. Therefore, the pressure sensor 730 measured the pressure in the fluid channel 711a, 711b, 711c of the sample tube set 710a, 710b, 710c for all samples.

Test procedure: The pressure sensor was calibrated to produce a reading of 0 mmHg when exposed to standard atmospheric pressure (which corresponds to an absolute pressure of 760 mmHg). Vacuum pressures (which have an absolute pressure less than 760 mmHg) resulted in a negative reading on the pressure sensor. For example, when exposed to an absolute pressure of 610 mmHg, the pressure sensor would produce a reading of −150 mmHg. For the purposes of this discussion, pressures will be described as absolute pressures.

The vacuum source was turned on and set to generate a vacuum having an absolute pressure of 610 mmHg. When the vacuum source was running but no load was placed on the tube set (crushing force=0 N), the pressure sensor would measure an absolute pressure in the fluid channel that was approximately equal to atmospheric pressure (760 mmHg) because the patient end of the tube set was open to atmosphere.

The thin plate was moved toward the sample platform at a rate of 0.03 mm/second, thereby applying a crushing force to the tube set. As the crushing force increased, the fluid channel began to close, and the absolute pressure in the fluid channel decreased from atmospheric pressure to a value that was less than atmospheric pressure. The test was stopped when the absolute pressure in the fluid channel was equal to or less than 625 mmHg (indicating that the fluid channel had been occluded), and the peak crushing force was recorded. Three sample tube sets of each of Comparison A, Comparison B, and Example 1 were tested, and each sample was tested at three locations along the length of the tube set. The results are shown in Table 1.

TABLE 1

Crushing force required to occlude fluid channel of sample tube sets

| Sample No. | Location No. | Crushing Force (N) required to occlude fluid channel | | |
| --- | --- | --- | --- | --- |
| | | Comparison A | Comparison B | Example 1 |
| 1 | 1 | 40.36 | 24.22 | 120.00 |
| | 2 | 39.80 | 25.55 | 119.39 |
| | 3 | 40.01 | 26.70 | 128.10 |
| | Sample Average | 40.06 | 25.49 | 122.50 |
| 2 | 1 | 40.46 | 25.12 | 128.79 |
| | 2 | 38.02 | 25.85 | 105.16 |
| | 3 | 44.43 | 25.16 | 121.91 |
| | Sample Average | 40.97 | 25.38 | 118.62 |
| 3 | 1 | 49.40 | 24.49 | 141.32 |
| | 2 | 47.05 | 25.93 | 122.41 |
| | 3 | 47.06 | 22.64 | 125.42 |
| | Sample Average | 47.84 | 24.35 | 129.72 |
| OVERALL AVERAGE | | 42.95 | 25.07 | 123.61 |

As shown in Table 1, the average crushing force required to occlude the fluid channel of Example 1 tube sets (123.61 N) was significantly higher than the average crushing force required to occlude the fluid channel of Comparison A tube sets (42.95 N) and the average crushing force required to occlude the fluid channel of Comparison B tube sets (25.07 N). A two sample unpaired student's t-test at a 95% confidence level ($\alpha=0.05$) was used to individually compare Example 1 tube sets to Comparison A tube sets, and Example 1 tube sets to Comparison B tube sets. The force measurements measured at the three locations on the same sample were averaged, and this sample average was treated as one data point (n=3 for each of Comparison A, Comparison B, and Example 1). These t-tests showed that the crushing forces required to occlude the fluid channels of Example 1 tube sets was statistically significantly higher than the crushing forces required to occlude the fluid channels of Comparison A tube sets and Comparison B tube sets (the p-value for each comparison was less than 0.0001).

The foregoing description is provided to enable any person skilled in the art to practice the various example implementations described herein. Various modifications to these variations will be readily apparent to those skilled in the art, and the generic principles defined herein may be applied to other implementations. All structural and functional equivalents to the elements of the various illustrious examples described throughout this disclosure that are known or later come to be known to those of ordinary skill in the art are expressly incorporated herein by reference.

What is claimed is:

1. A wound therapy system comprising:
a wound dressing;
a pressure sensor;
a container having an internal chamber;
a vacuum source pneumatically associated with the internal chamber of the container; and
a tube set comprising a first tube and a second tube, wherein the first tube forms a fluid channel, and wherein the second tube forms a sensor channel in the tube set;
wherein the wound dressing is pneumatically associated with the internal chamber of the container by the fluid channel of the tube set;
wherein the wound dressing is pneumatically associated with the pressure sensor by the sensor channel of the tube set; and
wherein the container has a first port comprising a first attachment and a second attachment;
wherein a first end of the first tube is coupled to the wound dressing and a second end of the first tube is coupled to the first attachment of the first port; and
wherein a first end of the second tube connects to the wound dressing and a second end of the second tube connects to the second attachment of the first port.

2. The wound therapy system of claim 1, wherein the second tube is formed within the first tube,
wherein the sensor channel is a lumen of the second tube, and
wherein the fluid channel is a space between the first tube and second tube.

3. The wound therapy system of claim 2, wherein a crushing force required to occlude the fluid channel is greater than a crushing force required to occlude a fluid channel of a comparison tube set that does not include a second tube positioned inside a lumen of the first tube.

4. The wound therapy system of claim 1, wherein the container further comprises a second port and a sensor tube, wherein a first end of the sensor tube is connected to the second attachment of the first port and the second end of the sensor tube is connected to the second port, and wherein the pressure sensor is pneumatically associated with the second port on the container.

5. The wound therapy system of claim 1, further comprising an adapter that couples the second end of the first tube to the first attachment of the first port and the second end of the second tube to the second attachment of the first port.

6. The wound therapy system of claim 1, wherein the wound dressing is a first wound dressing, and wherein the wound therapy system further comprises a second wound dressing and a y-connector,
wherein a first port of the y-connector is pneumatically associated with the first port of the container, wherein a second port of the y-connector is pneumatically associated with the first wound dressing, and wherein a third port of the y-connector is pneumatically associated with the second wound dressing.

7. The wound therapy system of claim 1, wherein the fluid channel and the sensor channel are pneumatically associated with one another at the wound dressing.

8. The wound therapy system of claim 1, further comprising a pressure sensor pneumatically associated with the vacuum source.

9. A wound therapy system comprising:
a wound dressing;
a pressure sensor;
a first tube configured to form a fluid channel, and a second tube configured to form a sensor channel; and
a restrictor pneumatically associated with the wound dressing by the sensor channel of the first tube, wherein the restrictor has a hole that is configured to allow air to leak into the wound therapy system;
wherein the wound dressing is pneumatically associated with a vacuum source by the fluid channel; and
wherein the wound dressing is pneumatically associated with the pressure sensor by the sensor channel.

10. The wound therapy system of claim 9, wherein the restrictor comprises:
a body having a first port and a second port;
a cap coupled to the first port of the body, the cap having a hole; and
a porous material positioned between the cap and the first port of the body;
wherein air is configured to enter the device through the hole in the cap and pass through the porous material before entering the first port of the body.

11. The wound therapy system of claim 10, wherein the restrictor is adjustable, and wherein tightening a connection between the cap and the body compresses the porous material and decreases a rate of airflow across the porous material.

12. The wound therapy system of claim 9, wherein the restrictor leaks air into the system at a rate of about 0.05-0.1 liters per minute when the vacuum source applies a vacuum to the system.

13. The wound therapy system of claim 9, wherein vacuum source is configured to compensate for air leaking into the system such that the pressure at the wound dressing is not substantially altered.

14. The wound therapy system of claim 1, wherein the sensor channel has a cross-sectional area of at least 0.75 mm$^2$.

15. The wound therapy system of claim 1, wherein the tube set comprises exactly one sensor channel.

16. The wound therapy system of claim 1, wherein the tube set comprises a plurality of sensor channels.

17. A wound therapy system comprising:
a wound dressing;
a pressure sensor;
a container having an internal chamber;
a vacuum source pneumatically associated with the internal chamber of the container; and
a tube set comprising a first tube configured to form a fluid channel and a second tube configured to form a sensor channel in the tube set;
wherein the wound dressing is pneumatically associated with the internal chamber of the container by the fluid channel of the tube set;
wherein the wound dressing is pneumatically associated with the pressure sensor by the sensor channel of the tube set; and
wherein the tube set is a first tube set, and wherein the wound therapy system further comprises a second tube set having a fluid channel and a sensor channel, and a valve positioned in-line between the first tube set and the second tube set.

18. The wound therapy system of claim 17, wherein the valve has an open position and a closed position;
wherein the valve, when in the open position, allows communication between the fluid channel of the first tube set and the fluid channel of the second tube set, and also allows communication between the sensor channel of the first tube set and the sensor channel of the second tube set; and
wherein the valve, when in the closed position, blocks communication between the fluid channel of the first tube set and the fluid channel of the second tube set, and also blocks communication between the sensor channel of the first tube set and the sensor channel of the second tube set.

19. The wound therapy system of claim 1, wherein the first tube and the second tube are able to maintain their shape when a vacuum is applied by the vacuum source.

20. The wound therapy system of claim 1, wherein the fluid channel is substantially unobstructed.

21. A method of wound therapy comprising:
applying a dressing to a wound, wherein the dressing is coupled to a tube set comprising a fluid channel and a sensor channel;
applying a vacuum to the fluid channel, wherein the vacuum draws exudate from the wound into the fluid channel; and
providing a restrictor pneumatically associated with the wound dressing by the sensor channel, the restrictor having a hole through which air can leak into the sensor channel, wherein the air pushes fluids from the wound dressing into the fluid channel of the tube set.

22. The method of claim 21, wherein the step of applying the vacuum to the fluid channel allows air to continuously leak from the restrictor into the sensor channel.

23. The method of claim 21, further comprising a step of opening the restrictor intermittently to allow air to leak into the sensor channel when the restrictor is open.

24. The method of claim 23, wherein the restrictor is a solenoid.

25. The method of claim 21, further comprising:
measuring a therapeutic pressure at the dressing using a pressure sensor connected to the sensor channel; and
adjusting the pressure of the vacuum applied to the fluid channel based on the therapeutic pressure measured by the pressure sensor.

26. The method of claim 21, further comprising a step of forming the tube set such that the tube set comprises an inner tube and an outer tube, wherein the sensor channel is a lumen of the inner tube, and wherein the fluid channel is a space between the outer tube and inner tube.

27. The method of claim 21, further comprising a step of adjusting the restrictor to change the rate at which air leaks into the system.

28. A device for creating an air leak, the device comprising:
a body having a first port in communication with a second port;
a cap coupled to the first port of the body, the cap having a hole; and
a porous material positioned between the cap and the first port of the body;
wherein air is configured to enter the device through the hole in the cap and pass through the porous material before entering the body via the first port.

29. The device of claim 28, wherein tightening a connection between the cap and the body compresses the porous material and decreases a rate of airflow across the porous material.

30. The device of claim 28, wherein the device is configured to allow air to flow out of the second port at a rate of 0.05-0.1 liters per minute.

31. The wound therapy system of claim 9, further comprising a container having an internal chamber, wherein the vacuum source pneumatically associated with the internal chamber of the container, and the container is positioned between the wound dressing and the vacuum source.

* * * * *